(12) United States Patent
Borodina et al.

(10) Patent No.: US 11,345,922 B2
(45) Date of Patent: May 31, 2022

(54) METHODS FOR PRODUCING FATTY ALCOHOLS AND DERIVATIVES THEREOF IN YEAST

(71) Applicant: Danmarks Tekniske Universitet, Kgs. Lyngby (DK)

(72) Inventors: Irina Borodina, Nivå (DK); Carina Holkenbrink, Kongens Lyngby (DK); Marie Inger Dam, Birkerød (DK); Christer Löfstedt, Lund (SE)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 16/470,024

(22) PCT Filed: Dec. 15, 2017

(86) PCT No.: PCT/EP2017/083021
§ 371 (c)(1),
(2) Date: Jun. 14, 2019

(87) PCT Pub. No.: WO2018/109163
PCT Pub. Date: Jun. 21, 2018

(65) Prior Publication Data
US 2019/0330646 A1    Oct. 31, 2019

(30) Foreign Application Priority Data
Dec. 16, 2016 (EP) .................................. 16204769

(51) Int. Cl.
*C12N 15/52* (2006.01)
*C12N 15/81* (2006.01)
*C12P 7/04* (2006.01)

(52) U.S. Cl.
CPC ........... *C12N 15/815* (2013.01); *C12N 15/52* (2013.01); *C12P 7/04* (2013.01); *C12Y 114/19001* (2013.01)

(58) Field of Classification Search
CPC .................................. C12P 7/04; C12N 15/52
See application file for complete search history.

(56) References Cited

U.S. PATENT DOCUMENTS

| | | | |
|---|---|---|---|
| 5,876,994 | A | 3/1999 | Knipple et al. |
| 8,323,935 | B2 | 12/2012 | Xue et al. |
| 9,157,103 | B2 | 10/2015 | Hattendorf et al. |
| 10,308,962 | B1* | 6/2019 | Leonard ........... C12Y 102/0105 |
| 2012/0165562 | A1 | 6/2012 | Hattendorf et al. |

FOREIGN PATENT DOCUMENTS

| | | |
|---|---|---|
| CN | 102795997 A | 11/2012 |
| EP | 2655612 B1 | 7/2017 |
| WO | 200062792 A2 | 10/2000 |
| WO | 03074715 A2 | 9/2003 |
| WO | 2004031395 A1 | 4/2004 |
| WO | 2012087958 A2 | 6/2012 |
| WO | 2013096082 A1 | 6/2013 |
| WO | 2015013674 A2 | 1/2015 |
| WO | 2015057155 A1 | 4/2015 |
| WO | 2015171057 A1 | 11/2015 |
| WO | 2016207339 A1 | 12/2016 |
| WO | 2017087846 A1 | 5/2017 |

OTHER PUBLICATIONS

C.D. Retter et al. "Production of 1-decanol by metabolically engineered Yarrowia lipolytica", Metabolic Engineering 38: 139-147 (Year: 2016).*
Dunkelblum et al.: "Identification of the sex pheromone of the cotton bollworm, *Heliothis armigera*, inIsrael", Phytoparasitica 8, 209-211 (1980).
Fujii et al.: "Molecular Cloning, Sequence Analysis, and Expression of the Yeast Alcohol Acetyltransferase Gene", Applied and Environmental Microbiology, Aug. 1994, p. 2786-2792.
Kehat et al.: "Behavioral responses of male *Heliothis armigera* (Lepidoptera: Noctuidae) moths in a flight tunnel to combinations of components identified from female sex pheromone glands", Journal of Insect Bhavior, 3(1):75-83, 1990.
Knipple et al.: "Cloning and functional expression of a cDNA encoding a pheromone gland-specific acyl-CoA D11-desaturase of the cabbage looper moth, *Trichoplusia ni*", Proc. Natl. Acad. Sci. USA, vol. 95, pp. 15287-15292, Dec. 1998, Biochemistry.
Knoll et al.: "Biochemical Studies of Three Saccharomyces cerevisiae Acyl-CoA Synthetases, Faalp, FaaZp, and Faa3p", The Journal of Biological Chemist, vol. 269, No. 23, Issue of Jun. 10,pp. 16348-16356, 1994.
Moto et al.: "Pheromone gland-specific fatty-acyl reductase of the silkmoth, *Bombyx mori*", 9156-9161 PNAS, Aug. 5, 2003, vol. 100, No. 16.
Nesbitt et al.: "(Z)-9-Hexadecenal: a minor component of the female sex pheromone of Heliothis armigera (Hübner) (Lepidoptera, Noctuidae) Entomol. Exp. Appl. 27, 306-308 (1980).
Zhang et al.: "An overlooked component: (Z)-9-tetradecenal as a sex pheromone in Helicoverpa armigera", J. Insect Physiol. 58, 1209-1216 (2012).
Roelofs, W. et al., Molecular genetics and evolution of pheromone biosynthesis in Lepidoptera, PNAS, 10016): 9179-9184, Aug. 5, 2003.
Ando, T. et al.; "LepidopteranSex Pheromone, Topics in Current Chemistry"; 239: pp. 51-96; Year: 2004.
Gatter, M.; "A newly identified fatty alcohol oxidase gene is mainly responsible for the oxidation of long-chain x-hydroxy fatty acids in Yarrowia lipolytica", FEMS Yeast Res 14, 858-872; Year: 2014.
Heath, R. et al., "Periodicity of Female Sex Pheromone Titer and Release in Heliothis subflexa and H. virescens (Lepidoptera: Noctuidae)", Annals of the Entomological Society of America, 84:2; pp. 182-189; Year: 1991.

(Continued)

Primary Examiner — Tekchand Saidha
(74) Attorney, Agent, or Firm — Dinsmore & Shohl

(57) ABSTRACT

The present invention relates to oleaginous yeast cells for the production of fatty alcohols and derivatives thereof, in particular desaturated fatty alcohols, desaturated fatty acyl acetates and desaturated fatty aldehydes. Also provided are methods for obtaining such compounds, which are useful in pheromone compositions.

17 Claims, 4 Drawing Sheets

Specification includes a Sequence Listing.

(56) References Cited

OTHER PUBLICATIONS

Suckling, D.M. et al., "Improving the Pheromone Lure for Diamondback Moth", New Zealand Plant Protection, vol. 55; pp. 182-187; Year: 2002.
Lee, S. et al., "Sex pheromone composition if the diamondback moth Plutella xylostella in Korea", J. Asia-Pacific Entomol., 8(3), pp. 243-248; Year: 2005.
Rosenfield, C-L. et al., "Structural and functional conservation and divergence among acyl-CoA desaturases of two noctuid species, the corn earworm, Helicoverpa zea1, and the cabbage looper, Trichoplusia ni", Insect Biochemistry and Molecular Biology, vol. 31, pp. 949-964; Year: 2001.
Sheng, J. et al., Metabolic engineering of yeast to produce fatty acid-derived biofuels: bottlenecks and solutions, Frontiers in Microbiology; vol. 6, pp. 1-11; Year: 2015.
Bao-Jian Ding, et al.; Nature Communications; vol. 5; 2014; DOI: 10.1038/ncomms4353.
Alfaro, et al.; Crop Protection, vol. 28; pp. 567-572, 2009.
Angerer, et al.; PNAS, vol. 111, No. 14, pp. 5207-5212; 2014.
Antony, et al.; Scientific Reports, vol. 6, No. 29927; DOI: 10.1038/srep29927, 2016.
Bari, M.A.; "Development of pheromone mating disruption strategies for the suppression of the artichoke plume moth in artichokes grown on the central coast of California"; Proc, of Vth IC of Artichoke; Ed. F.J.Sanz Villar, Acta Hort, 660, pp. 523-527; 2002.
Chen, et al.; Appl Microbiol Biotechnol; vol. 48, pp. 232-235, 1997.
Dallerac, et al.; PNAS, vol. 97, No. 17; pp. 9449-9454, Aug. 15, 2000.
Ding, B-J. (2014). On the way of making plants smell like moths—a synthetic biology approach. Lund: Lund University, Faculty of Science, Department of Biology.
Ding, Baojian & Lofstedt, Christer; BMC Genomics, vol. 16; DOI 10.1186/s12864-015-1909-2; 2015.
Ding, et al.; Lipids; vol. 51, pp. 469-475; 2016.
Eizaguirre, et al.; Use of pheromones and other semiochemicals in integrated production, IOBC wprs Bulletin; vol. 25, pp. 1-10; 2002.
Feng, et al.; Metabolic Engineering, vol. 27, pp. 10-19; 2015.
Ferrell, William J. and Yao, Kuo-Ching; J Lipid Res., vol. 13, pp. 23-26; 1972.
Fickers, et al.; FEMS Yeast Research, vol. 5, pp. 527-543; 2005.
Gietz, R. Daniel and Schiestl, Robert H.; Nat Protoc., vol. 2, No. 1, pp. 31-34, 2007.
Gietz, R. Daniel and Schiestl, Robert H.; Nat Protoc., vol. 2, No. 1; pp. 35-37; 2007.
Guerful et al.; Microbial Cell Factories; vol. 12, No. 122; 2013.
Hagstrom, et al.; Microbial Cell Factories; vol. 12, pp. 1-11; 2013.
Iwama, et al.; FEMS Yeast Res.; vol. 15, No. 3; doi: 10.1093/femsyr/fov014; 2015.
Iwama, et al.; J Biol Chem., vol. 289, No. 48; pp. 33275-33286, 2014.
Jensen, et al.; FEMS Yeast Res., vol. 14, No. 2; pp. 238-248; 2014.
Jessop-Fabre, et al.; Biotechnol J., vol. 11, No. 8; pp. 1110-1117; 2016.
Kehat, Moshe and Dunkelblum, Ezra; Archives of Insect Biochemistry and Physiology, vol. 22, pp. 425-431; 1993.
Knipple, et al.; Genetics, vol. 162, pp. 1737-1752; 2002.
Li, et al.; Synthesis, No. 7, pp. 1163-1169; 2009.
Maury, et al.; PLoS One, vol. 11, No. 3; doi:10.1371/journal.pone.0150394; 2016.
Meyer et al.; J. Org. Chem., vol. 59, pp. 7549-7552; 1994.
Mitchell et al.; Journal of Economic Entomology, vol. 75, No. 2, pp. 270-274; 1982.
Okada, et al.; ChemInform, vol. 45(33), one page; DOI: 10.1002/chin.201433042; 2014.
Schneiter, et al.; J. Bacteriol., vol. 182, No. 13 pp. 3655-3660; 2000.
Sheng, et al.; Frontiers in Microbiology, Article 554, vol. 6; doi: 10.3389/fmicb.2015.00554; 2015.
Steves, et al.; J. Am. Chem. Soc., vol. 135, pp. 15742-15745; 2013.
Stovicek, et al.; J Ind Microbiol Biotechnol, vol. 42, pp. 1519-1531; 2015.
Sumita, et al.; FEMS Microbiol Lett., vol. 214, pp. 31-38; 2002.
Tamura, et al.; Synlett, vol. 23, pp. 1397-1407; 2012.
Tumlinson, et al.; Journal of Chemical Ecology, vol. 12, No. 9, 1986.
Wang, et al.; Biotechnology for Biofuels, vol. 9, No. 1; DOI 103.1186/s13068-016-0512-3; 2016.
Wu, et al.; Insect Science, vol. 19, pp. 643-648; DOI 10.1111/j.1744-7917.2011.01497.x; 2012.
Yadav et al.; Tetrahedron, vol. 60, pp. 2131-2135; 2004.
XP-002750785; Database UniProt—2014, one page, Accession No. S4WAY4.
Zhang, Y. et al., Identification and Expression Profiles of Sex Pheromone Biosynthesis and Transport Related Genes in Spodoptera litura, PLoS ONE 10(10): e0140019, 2015.
Machine English translation of CN102795997A.
Rodriguez, G. et al., Expanding ester biosynthesis in Escherichia coli, Nat Chem Biol., 10(4): 259-265, Apr. 2014.
Bjostad, L. et al., Biosynthesis of Sex Pheromone Components and Glycerolipid Precursors From Sodium [lj4c] Acetate in Redbanded Leafroller Moth, Journal of Chemical Ecology, 10(4): 681-691, 1984.
Jurenka, R., Insect Pheromone Biosynthesis, Topics in Current Chemistry, 239: 97-132, 2004.

\* cited by examiner

SEQUENCE LISTING

<160> NUMBER OF SEQ ID NOS: 114

<210> SEQ ID NO 1
<211> LENGTH: 981
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(981)
<223> OTHER INFORMATION: S. cerevisiae-codon-optimized nucleotide
      sequence of A. transitella delta11-desaturase; mRNA-coding
      sequence.

<400> SEQUENCE: 1
atggttccaa acaagggttc ctctgatgtt ttgtctgaac attctgaacc acaattcacc    60
aagttgattg ctccacaagc tggtccaaga agtacaaaa tcgtttacag aaacttgttg    120
accttcggtt actggcattt gtctgctgtt tatggttttgt acttgtgttt cacttgtgct    180
aagtgggcta ctattttgtt cgctttcttc ttgtacgtta tcgccgaaat tggtattact    240
ggtggtgctc atagattatg ggctcataga acttacaaag ccaagttgcc attggaaatc    300
ttgttgttga tcatgaactc cattgccttc aagatactg cttttacttg ggctagagat    360
catagattgc atcacaagta ctctgatact gatgctgatc acataatgc tactagaggt    420 ttcttctact ctcatgttgg ttggttgttg ttaagaaac acccagaagt taaggctaga    480
ggtaagtact tgtctttgga tgacttgaag aacaacccct tgttgaagtt ccaaaagaag    540
tacgccattt tggtcattgg tactttgtgc ttttgatgc aactttcgt tccagtttac    600 ttttggggtg aaggtatttc tactgcctgg aacattaact tgttaagata cgtcatgaac    660
ttgaacatga cctttttggt taactccgct gctcatattt ttggtaacaa gccatacgat    720
aagtctatcg cctctgttca aacatctct gtttctttgg ctactttcgg tgaaggtttc    780
cataactacc atcatactta ccatgggat tacagagctg ctgaattggg taacaataga    840
ttgaatatga ccaccgcctt cattgatttc tttgcttgga ttggttgggc ctacgatttg    900
aaatctgttc cacaagaagc tattgctaag agatgtgcta aaactggtga tggtactgat    960
atgtggggta gaaagagatg a                                              981

<210> SEQ ID NO 2
<211> LENGTH: 326
<212> TYPE: PRT
<213> ORGANISM: Amyelois transitella
<220> FEATURE:
<221> NAME/KEY: MISC_FEATURE
<222> LOCATION: (1)..(326)
<223> OTHER INFORMATION: Amino acid sequence of A. transitella
      delta-11-desaturase (translation)

<400> SEQUENCE: 2

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Ile Met Asn Ser Ile Ala Phe Gln Asp
            100                 105                 110

Thr Ala Phe Thr Trp Ala Arg Asp His Arg Leu His His Lys Tyr Ser
            115                 120                 125

Asp Thr Asp Ala Asp Pro His Asn Ala Thr Arg Gly Phe Phe Tyr Ser
130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
            195                 200                 205

Ala Trp Asn Ile Asn Leu Leu Arg Tyr Val Met Asn Leu Asn Met Thr
210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
            275                 280                 285

Asp Phe Phe Ala Trp Ile Gly Trp Ala Tyr Asp Leu Lys Ser Val Pro
290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 3
<211> LENGTH: 1560
<212> TYPE: DNA
<213> ORGANISM: Yarrowia lipolytica

<400> SEQUENCE: 3
atgtctacct tgattgggga atccattgtg cctgccactc ctctcgacca gattcctggc      60
gacatccagc gactgcgaaa gggcttccga tccggaaaga ccctcgatct caactaccga     120
ctggaccaga ttcgaaactt gcactacgtc ctcagagaca atgtcgaggc catcaaggac     180
gccgtgtaca aggatctcgg ccgacccaag cacgagactg acctgtgcga ggtgggtttc     240
ctgtggggcg agtttaacaa cgtggttgcc aacctcaaga gtgggccgc cgacgaggac     300 gtcaagacca acctgcagta ctccatctcc tcccccaaga tccgaaagcg acctcttgga     360
aacgtgctca tcatctcgcc ctggaactac ccctttatgc tgaccgtgtc tcctctcatt     420
ggagctctgg ctgccggtaa cactgtggct gtcaagttct ccgaaatggc ccccacact      480 tccaaaattg ttggcgactt gtgcaccaag gccctcgacc ccgacgtctt ccaggccatc     540
cagggaggtg tccccgtcgt caccaagacc ctcgagcaga gttcgacaa gattatgtac     600 actggtaacc acactgtcgg taagatcatt gccactgccg ccaacaagta cctgacaccc     660

```
gtcatcctcg agctcggagg taagtcgccc gttttttgtca ccaagaactg caagaacatc    720
aagcttgccg ctaagcgagc cctgtggggt aaggtggtaa acgctggcca gacctgtgtg    780
gctcccgact acgtgattgt cgagcccgag gtggagcagg agtttatcga cgcctgcaag    840
tactggatta acgagttcta cagtggtaag attgaccagt acaaccccga ctttgccaag    900
atcgccaccc ccaaccactg gaaccgactt acctccatgt tgagcaagtc caagggagag    960
atcattactg gaggtaacac tgacgagaag actcgattca tcgctcctac tgtcgtcgca   1020
aaggtccccg acaatgattc cctgatggag gacgagattt tcggccctct tctgcccatt   1080
ctcactgccc gatccgtcga ggagggtatc aagtacgtgc acgagaacca cgacacccct   1140
cttgccatgt acgtcttcac tgacaaggcc tctgagggcg actacatcca gtcccagatc   1200
aactctggtg ccttatctt caatgacact ctgatccacg ttggatgtgt ccaggctccg   1260
tttggtggtg tcggcatgtc cggttacggt gcttaccatg cgaggactc cttcctggcc   1320 ttcacccacc gacaaaccta cctcaaccag cccaagcttc tggagcctct tcaggacgtg   1380
cgatacgccc cctacaccaa aaccaagcga agcatggtca gaacctgct gctggtcggc   1440 cccatttttcc cccgaaccgg ctccgtatac cccaacgtgc tgatccgaat cttccgaaag   1500
atttggttct gggtccttat tgtcgccatc ggagctgctg gtgccaaggc tctgctctag   1560
```

<210> SEQ ID NO 4
<211> LENGTH: 519
<212> TYPE: PRT
<213> ORGANISM: Yarrowia lipolytica

<400> SEQUENCE: 4

```
Met Ser Thr Phe Asp Trp Glu Ser Ile Val Pro Ala Thr Pro Leu Asp
1               5                   10                  15

Gln Ile Pro Gly Asp Ile Gln Arg Leu Arg Lys Gly Phe Arg Ser Gly
                20                  25                  30

Lys Thr Leu Asp Leu Asn Tyr Arg Leu Asp Gln Ile Arg Asn Leu His
            35                  40                  45

Tyr Val Leu Arg Asp Asn Val Glu Ala Ile Lys Asp Ala Val Tyr Lys
        50                  55                  60

Asp Leu Gly Arg Pro Lys His Glu Thr Asp Leu Cys Glu Val Gly Phe
65                  70                  75                  80

Leu Trp Gly Glu Phe Asn Asn Val Val Ala Asn Leu Lys Lys Trp Ala
                85                  90                  95

Ala Asp Glu Asp Val Lys Thr Asn Leu Gln Tyr Ser Ile Ser Ser Pro
            100                 105                 110

Lys Ile Arg Lys Arg Pro Leu Gly Asn Val Leu Ile Ile Ser Pro Trp
        115                 120                 125

Asn Tyr Pro Phe Met Leu Thr Val Ser Pro Leu Ile Gly Ala Leu Ala
    130                 135                 140

Ala Gly Asn Thr Val Ala Val Lys Phe Ser Glu Met Ala Pro His Thr
145                 150                 155                 160

Ser Lys Ile Val Gly Asp Leu Cys Thr Lys Ala Leu Asp Pro Asp Val
                165                 170                 175

Phe Gln Ala Ile Gln Gly Gly Val Pro Val Val Thr Lys Thr Leu Glu
            180                 185                 190

Gln Lys Phe Asp Lys Ile Met Tyr Thr Gly Asn His Thr Val Gly Lys
        195                 200                 205

Ile Ile Ala Thr Ala Ala Asn Lys Tyr Leu Thr Pro Val Ile Leu Glu
    210                 215                 220
```

```
Leu Gly Gly Lys Ser Pro Val Phe Val Thr Lys Asn Cys Lys Asn Ile
225                 230                 235                 240

Lys Leu Ala Ala Lys Arg Ala Leu Trp Gly Lys Val Val Asn Ala Gly
            245                 250                 255

Gln Thr Cys Val Ala Pro Asp Tyr Val Ile Val Glu Pro Glu Val Glu
        260                 265                 270

Gln Glu Phe Ile Asp Ala Cys Lys Tyr Trp Ile Asn Glu Phe Tyr Ser
    275                 280                 285

Gly Lys Ile Asp Gln Tyr Asn Pro Asp Phe Ala Lys Ile Ala Thr Pro
290                 295                 300

Asn His Trp Asn Arg Leu Thr Ser Met Leu Ser Lys Ser Lys Gly Glu
305                 310                 315                 320

Ile Ile Thr Gly Gly Asn Thr Asp Glu Lys Thr Arg Phe Ile Ala Pro
                325                 330                 335

Thr Val Ala Lys Val Pro Asp Asn Asp Ser Leu Met Glu Asp Glu
            340                 345                 350

Ile Phe Gly Pro Leu Leu Pro Ile Leu Thr Ala Arg Ser Val Glu Glu
        355                 360                 365

Gly Ile Lys Tyr Val His Glu Asn His Asp Thr Pro Leu Ala Met Tyr
370                 375                 380

Val Phe Thr Asp Lys Ala Ser Glu Gly Asp Tyr Ile Gln Ser Gln Ile
385                 390                 395                 400

Asn Ser Gly Gly Leu Ile Phe Asn Asp Thr Leu Ile His Val Gly Cys
                405                 410                 415

Val Gln Ala Pro Phe Gly Gly Val Gly Met Ser Gly Tyr Gly Ala Tyr
            420                 425                 430

His Gly Glu Asp Ser Phe Leu Ala Phe Thr His Arg Gln Thr Tyr Leu
        435                 440                 445

Asn Gln Pro Lys Leu Leu Glu Pro Leu Gln Asp Val Arg Tyr Ala Pro
450                 455                 460

Tyr Thr Lys Thr Lys Arg Ser Met Val Lys Asn Leu Leu Leu Val Gly
465                 470                 475                 480

Pro Ile Phe Pro Arg Thr Gly Ser Val Tyr Pro Asn Val Leu Ile Arg
                485                 490                 495

Ile Phe Arg Lys Ile Trp Phe Trp Val Leu Ile Val Ala Ile Gly Ala
            500                 505                 510

Ala Gly Ala Lys Ala Leu Leu
        515

<210> SEQ ID NO 5
<211> LENGTH: 1590
<212> TYPE: DNA
<213> ORGANISM: Yarrowia lipolytica

<400> SEQUENCE: 5
atgactacca ctgccacaga gaccccacg acaaacgtga ccccaccac gtcactgccc     60 aaggagaccg cctccccagg agggaccgct tctgtcaaca cgtcattcga ctgggagagc    120
atctgcggca agacgccgtt ggaggagatc gagtcggaca tttcgcgtct caaaaagacc    180
ttccgatcgg gcaaaactct ggatctggac taccgactcg accagatccg aaacctggcg    240
tatgcgatcc gcgataacga aaacaagatc cgcgacgcca tcaaggcgga cctgaaacga    300
cctgacttcg aaaccatggc ggccgagttc tcggtccaga tgggcgaatt caactacgtg    360
gtcaaaaacc tgccgaaatg ggtcaaggac gaaaaagtca agggaaccag catggcgtac    420
```

```
tggaactcgt cgccaaagat ccggaaacgg cccctgggct ccgtgcttgt catcacgccc      480
tggaactacc cactgattct ggccgtgtcg cctgttctgg gcgccattgc cgcaggcaac      540
accgtggcgc tgaaaatgtc agaaatgtca cccaacgcgt caaaggtgat tggcgacatt      600
atgacagctg ccctggaccc ccagctcttt caatgcttct tcggaggagt ccccgaaacc      660
accgagatcc tcaaacacag atgggacaag atcatgtaca ccggaaacgg caaagtgggc      720
cgaatcatct gtgaggctgc caacaagtac ttgacacctg tggagctcga actcggagga      780
aagtcgcctg ttttcgtcac caaacactgc tccaacctgg aaatggccgc ccgccgaatc      840
atctggggca aattcgtcaa cggaggacaa acctgcgtgg ctccagacta cgttctggtg      900
tgtcccgagg tccacgacaa atttgtggct gcctgtcaaa aggtgctgga caagttctac      960
cctaacaact ctgccgagtc cgagatggcc catatcgcca cccctctcca ttacgagcgt     1020
ttgacgggcc tgctcaattc cacccgaggt aaggtcgttg ctggaggcac tttcaactcg     1080 gccaccggt tcattgctcc tacgattgtc gacggagtgg atgccaacga ttctctgatg      1140
cagggagaac tgtttggtcc tcttctcccc attgtcaagg ccatgagcac cgaggctgcc     1200
tgcaactttg tgcttgagca ccaccccacc cccctggcag agtacatctt ttcagataac     1260
aattctgaga ttgattacat ccgagatcga gtgtcgtctg gaggtctcgt gatcaacgac     1320
actctgatcc acgtgggatg cgtacaggcg ccctttggag gtgtcggaga cagtggaaat     1380
ggaggatacc atggcaagca cactttcgat tgttcagcc attctcagac ggtcctcaga      1440
caacccggat gggtcgaaat gctgcagaag aaacggtatc ctccgtacaa caagagcaac     1500
gagaagtttg tccggagaat ggtggtcccc agccctggtt ttccccggga gggtgacgtg     1560
agaggatttt ggtcgagact cttcaactag                                      1590
```

<210> SEQ ID NO 6
<211> LENGTH: 529
<212> TYPE: PRT
<213> ORGANISM: Yarrowia lipolytica

<400> SEQUENCE: 6

```
Met Thr Thr Thr Ala Thr Glu Thr Pro Thr Thr Asn Val Thr Pro Thr
1               5                   10                  15

Thr Ser Leu Pro Lys Glu Thr Ala Ser Pro Gly Gly Thr Ala Ser Val
            20                  25                  30

Asn Thr Ser Phe Asp Trp Glu Ser Ile Cys Gly Lys Thr Pro Leu Glu
        35                  40                  45

Glu Ile Glu Ser Asp Ile Ser Arg Leu Lys Lys Thr Phe Arg Ser Gly
    50                  55                  60

Lys Thr Leu Asp Leu Asp Tyr Arg Leu Asp Gln Ile Arg Asn Leu Ala
65                  70                  75                  80

Tyr Ala Ile Arg Asp Asn Glu Asn Lys Ile Arg Asp Ala Ile Lys Ala
                85                  90                  95

Asp Leu Lys Arg Pro Asp Phe Glu Thr Met Ala Ala Glu Phe Ser Val
            100                 105                 110

Gln Met Gly Glu Phe Asn Tyr Val Val Lys Asn Leu Pro Lys Trp Val
        115                 120                 125

Lys Asp Glu Lys Val Lys Gly Thr Ser Met Ala Tyr Trp Asn Ser Ser
    130                 135                 140

Pro Lys Ile Arg Lys Arg Pro Leu Gly Ser Val Leu Val Ile Thr Pro
145                 150                 155                 160
```

```
Trp Asn Tyr Pro Leu Ile Leu Ala Val Ser Pro Val Leu Gly Ala Ile
            165                 170                 175
Ala Ala Gly Asn Thr Val Ala Leu Lys Met Ser Glu Met Ser Pro Asn
        180                 185                 190
Ala Ser Lys Val Ile Gly Asp Ile Met Thr Ala Ala Leu Asp Pro Gln
    195                 200                 205
Leu Phe Gln Cys Phe Phe Gly Val Pro Glu Thr Thr Glu Ile Leu
210                 215                 220
Lys His Arg Trp Asp Lys Ile Met Tyr Thr Gly Asn Gly Lys Val Gly
225                 230                 235                 240
Arg Ile Ile Cys Glu Ala Ala Asn Lys Tyr Leu Thr Pro Val Glu Leu
                245                 250                 255
Glu Leu Gly Gly Lys Ser Pro Val Phe Val Thr Lys His Cys Ser Asn
            260                 265                 270
Leu Glu Met Ala Ala Arg Arg Ile Ile Trp Gly Lys Phe Val Asn Gly
        275                 280                 285
Gly Gln Thr Cys Val Ala Pro Asp Tyr Val Leu Cys Pro Glu Val
    290                 295                 300
His Asp Lys Phe Val Ala Ala Cys Gln Lys Val Leu Asp Lys Phe Tyr
305                 310                 315                 320
Pro Asn Asn Ser Ala Glu Ser Glu Met Ala His Ile Ala Thr Pro Leu
                325                 330                 335
His Tyr Glu Arg Leu Thr Gly Leu Leu Asn Ser Thr Arg Gly Lys Val
            340                 345                 350
Val Ala Gly Gly Thr Phe Asn Ser Ala Thr Arg Phe Ile Ala Pro Thr
        355                 360                 365
Ile Val Asp Gly Val Asp Ala Asn Asp Ser Leu Met Gln Gly Glu Leu
    370                 375                 380
Phe Gly Pro Leu Leu Pro Ile Val Lys Ala Met Ser Thr Glu Ala Ala
385                 390                 395                 400
Cys Asn Phe Val Leu Glu His His Pro Thr Pro Leu Ala Glu Tyr Ile
                405                 410                 415
Phe Ser Asp Asn Asn Ser Glu Ile Asp Tyr Ile Arg Asp Arg Val Ser
            420                 425                 430
Ser Gly Gly Leu Val Ile Asn Asp Thr Leu Ile His Val Gly Cys Val
        435                 440                 445
Gln Ala Pro Phe Gly Val Gly Asp Ser Gly Asn Gly Gly Tyr His
    450                 455                 460
Gly Lys His Thr Phe Asp Leu Phe Ser His Ser Gln Thr Val Leu Arg
465                 470                 475                 480
Gln Pro Gly Trp Val Glu Met Leu Gln Lys Lys Arg Tyr Pro Pro Tyr
                485                 490                 495
Asn Lys Ser Asn Glu Lys Phe Val Arg Arg Met Val Val Pro Ser Pro
            500                 505                 510
Gly Phe Pro Arg Glu Gly Asp Val Arg Gly Phe Trp Ser Arg Leu Phe
        515                 520                 525
Asn
```

```
<210> SEQ ID NO 7
<211> LENGTH: 1134
<212> TYPE: DNA
<213> ORGANISM: Yarrowia lipolytica

<400> SEQUENCE: 7
```

```
atgtggggaa gttcacatgc attcgctggt gaatctgatc tgacactaca actacacacc    60
aggtccaaca tgagcgacaa tacgacaatc aaaaagccga tccgacccaa accgatccgg   120
acggaacgcc tgccttacgc tggggccgca gaaatcatcc gagccaacca gaaagaccac   180
tactttgagt ccgtgcttga acagcatctc gtcacgtttc tgcagaaatg aagggagta   240
cgatttatcc accagtacaa ggaggagctg agacggcgt ccaagtttgc atatctcggt   300
ttgtgtacgc ttgtgggctc caagactctc ggagaagagt acaccaatct catgtacact   360
atcagagacc gaacagctct accggggggtg gtgagacggt ttggctacgt gctttccaac   420
actctgtttc catacctgtt tgtgcgctac atgggcaagt gcgcgccaa actgatgcgc   480
gagtatcccc atctggtgga gtacgacgaa gatgagcctg tgcccagccc ggaaacatgg   540
aaggagcggg tcatcaagac gtttgtgaac aagtttgaca agttcacggc gctggagggg   600
tttaccgcga tccacttggc gattttctac gtctacggct cgtactacca gctcagtaag   660
cggatctggg gcatgcgtta tgtatttgga caccgactgg acaagaatga gcctcgaatc   720
ggttacgaga tgctcggtct gctgattttc gcccggtttg ccacgtcatt tgtgcagacg   780
ggaagagagt acctcggagc gctgctggaa aagagcgtgg agaaagaggc agggagaag   840
gaagatgaaa aggaagcggt tgtgccgaaa agaagtcgt caattccgtt cattgaggat   900
acagaagggg agacggaaga caagatcgat ctggaggacc ctcgacagct caagttcatt   960
cctgaggcgt ccagagcgtg cactctgtgt ctgtcataca ttagtgcgcc ggcatgtacg  1020
ccatgtggac acttttttctg ttgggactgt atttccgaat gggtgagaga gaagcccgag  1080
tgtcccttgt gtcggcaggg tgtgagagag cagaacttgt gcctatcag ataa        1134
```

<210> SEQ ID NO 8
<211> LENGTH: 377
<212> TYPE: PRT
<213> ORGANISM: Yarrowia lipolytica

<400> SEQUENCE: 8

```
Met Trp Gly Ser Ser His Ala Phe Ala Gly Glu Ser Asp Leu Thr Leu
  1               5                  10                  15

Gln Leu His Thr Arg Ser Asn Met Ser Asp Asn Thr Thr Ile Lys Lys
             20                  25                  30

Pro Ile Arg Pro Lys Pro Ile Arg Thr Glu Arg Leu Pro Tyr Ala Gly
         35                  40                  45

Ala Ala Glu Ile Ile Arg Ala Asn Gln Lys Asp His Tyr Phe Glu Ser
     50                  55                  60

Val Leu Glu Gln His Leu Val Thr Phe Leu Gln Lys Trp Lys Gly Val
 65                  70                  75                  80

Arg Phe Ile His Gln Tyr Lys Glu Glu Leu Glu Thr Ala Ser Lys Phe
                 85                  90                  95

Ala Tyr Leu Gly Leu Cys Thr Leu Val Gly Ser Lys Thr Leu Gly Glu
            100                 105                 110

Glu Tyr Thr Asn Leu Met Tyr Thr Ile Arg Asp Arg Thr Ala Leu Pro
        115                 120                 125

Gly Val Val Arg Arg Phe Gly Tyr Val Leu Ser Asn Thr Leu Phe Pro
    130                 135                 140

Tyr Leu Phe Val Arg Tyr Met Gly Lys Leu Arg Ala Lys Leu Met Arg
145                 150                 155                 160

Glu Tyr Pro His Leu Val Glu Tyr Asp Glu Asp Glu Pro Val Pro Ser
                165                 170                 175
```

Pro Glu Thr Trp Lys Glu Arg Val Ile Lys Thr Phe Val Asn Lys Phe
        180                 185                 190

Asp Lys Phe Thr Ala Leu Glu Gly Phe Thr Ala Ile His Leu Ala Ile
    195                 200                 205

Phe Tyr Val Tyr Gly Ser Tyr Tyr Gln Leu Ser Lys Arg Ile Trp Gly
210                 215                 220

Met Arg Tyr Val Phe Gly His Arg Leu Asp Lys Asn Glu Pro Arg Ile
225                 230                 235                 240

Gly Tyr Glu Met Leu Gly Leu Leu Ile Phe Ala Arg Phe Ala Thr Ser
            245                 250                 255

Phe Val Gln Thr Gly Arg Glu Tyr Leu Gly Ala Leu Leu Glu Lys Ser
        260                 265                 270

Val Glu Lys Glu Ala Gly Glu Lys Glu Asp Glu Lys Glu Ala Val Val
    275                 280                 285

Pro Lys Lys Lys Ser Ser Ile Pro Phe Ile Glu Asp Thr Glu Gly Glu
290                 295                 300

Thr Glu Asp Lys Ile Asp Leu Glu Asp Pro Arg Gln Leu Lys Phe Ile
305                 310                 315                 320

Pro Glu Ala Ser Arg Ala Cys Thr Leu Cys Leu Ser Tyr Ile Ser Ala
            325                 330                 335

Pro Ala Cys Thr Pro Cys Gly His Phe Phe Cys Trp Asp Cys Ile Ser
        340                 345                 350

Glu Trp Val Arg Glu Lys Pro Glu Cys Pro Leu Cys Arg Gln Gly Val
    355                 360                 365

Arg Glu Gln Asn Leu Leu Pro Ile Arg
370                 375

<210> SEQ ID NO 9
<211> LENGTH: 2184
<212> TYPE: DNA
<213> ORGANISM: Yarrowia lipolytica

<400> SEQUENCE: 9
atgtccgaaa ccgaccatct gctggccgcc gagcccgtgg ctgagtaccc ccagtacacg     60
ccttggccca actcccgaaa atcagtggac acggagtttt ccgcaacctc gtggatttac    120
gacttggttc tgtggatttt cacggcttgc tttgacattt ttttcagaga aatccggcca    180
cgtggtgcct tccgaatccc cagaaagggc cccgtgctgt tcgtggctgc cccccacgca    240
aaccagtttg tggaccccgt catcctcatg aaccaggtca acaggaggc cggacgacga    300 atctccttcc ttgtggccga agtccatg cgacgagctg cagtcggacg aatgccccga    360
agcatgaact caattcctgt cgtgcgagct caggacaatg caaaaaaggg agagggaaag    420
atttacgtcg acgcagagga ccccacaaag atccacggaa tcggcaccca gttcacgaag    480
cagtgcgagg tgcgaggcct cgtggtctgc tcgtcctctg tcggctcaat tgacgtggct    540
gagattgtgt ccgacactct gctcattgca agaaaggaat tcaagggccc caaagccaag    600
gaggctctca aggaatccaa cggaggaatc acatacaagt acgccgacta cgtcaaccag    660
gccacagtct accgatccgt attcgacaaa ttgcaccatg gaggctgtgt gggtatcttc    720
ccagagggag gatctcatga ccgaaccgaa ctgctgcccc ttaaggccgg tgttgctatc    780
atggctctgg gggctctcgc agaggacccc tcttgtggtg tgcgaatcgt ccctgtggt    840 ctcaactact ccacgcccca aagttccga tctcgggccg tggtggagtt tggctctcct    900
attgccattc ctccggatct cgtggagaag tacaaggcag gaggagaggc caagcgggag    960

```
gctgtcaaga ccgttctaga cattactgcc gctggtctca agtctgtgac tgttcaggtg   1020
caggatttcg acaccctgat gctgatccag gccattcgac gactctaccg acctcccgga   1080
aagaagattc ctctgcccat ggttgtagag ctcaaccgtc gacttgtata cgcctacaac   1140
cactacaagg acgatcccg tatcgaggag atgaagcagg agattcgaaa gtacaacaag   1200
ttcctgcagg ccatgggtct caaggaccat caggtagaga aggcccgaat ctccaagatt   1260
gagattctgg gccggcttct gtaccggtcc atcaagcttg tgttcttgtc cattggctgt   1320
ctccccggtc tgcttttgtt ttctcccatc ttcatcattt ctaagtccat ttccaaaacc   1380
aaggccaagg aggctctcaa ggcctccagt gtcaaaatca aggctaacga tgtggttgcc   1440
acttggaagg tgctggttgc aatgggtctg accccagttc tttacattct ctattcactg   1500
gttggatctg tggtgattcg aaagctcgat ctcatctcct ggttccccac aattcttctt   1560
cccggcctcg ttttaagcat catcatcaca acctcatacg ccgccctggc tatgggagag   1620
gccggtatgg acattttcaa gtctcttcga ccacttgcat tggctctcaa cccttccacc   1680
aaaaactctc tgctcaagct gcaaaatgaa cgaaagcgac ttgtgctcaa gtcttccgag   1740
ctcgttacct ctttgggccc tgagctgttc cccgacttcc ccgagaactc cattctgcag   1800
ggaagcgata agtttgagga cgaggagaac tacgaaaacg agaagcgatc gcattccaga   1860
tccacttctg ccacttctct atctgccatg agcgagggag acggtgatga gcttgttcgg   1920
gaggtccgaa agggtgctag ctacttccct gtgagtacca tttctgagga cgaagaccaa   1980
gccatctcgc gagtgggctc tgaggcatct cttgctgaca ttcctctgtt tggtatgtcc   2040
cgatcacaat ctggagcttc tctttcggaa gcctccacac acggctcttc tactggagct   2100
gatgccgagg aggctaagac ggaggtgact cgcagaattg cattggcgat ggaggaaaaa   2160
cgacgagagc aggatgagga ataa                                         2184
```

<210> SEQ ID NO 10  
<211> LENGTH: 727  
<212> TYPE: PRT  
<213> ORGANISM: Yarrowia lipolytica

<400> SEQUENCE: 10

```
Met Ser Glu Thr Asp His Leu Leu Ala Ala Glu Pro Val Ala Glu Tyr
1               5                   10                  15

Pro Gln Tyr Thr Pro Trp Pro Asn Ser Arg Lys Ser Val Asp Thr Glu
            20                  25                  30

Phe Ser Ala Thr Ser Trp Ile Tyr Asp Leu Val Leu Trp Ile Phe Thr
        35                  40                  45

Ala Cys Phe Asp Ile Phe Phe Arg Glu Ile Arg Pro Arg Gly Ala Phe
    50                  55                  60

Arg Ile Pro Arg Lys Gly Pro Val Leu Phe Val Ala Ala Pro His Ala
65                  70                  75                  80

Asn Gln Phe Val Asp Pro Val Ile Leu Met Asn Gln Val Lys Gln Glu
                85                  90                  95

Ala Gly Arg Arg Ile Ser Phe Leu Val Ala Glu Lys Ser Met Arg Arg
            100                 105                 110

Ala Ala Val Gly Arg Met Ala Arg Ser Met Asn Ser Ile Pro Val Val
        115                 120                 125

Arg Ala Gln Asp Asn Ala Lys Lys Gly Glu Gly Lys Ile Tyr Val Asp
    130                 135                 140

Ala Glu Asp Pro Thr Lys Ile His Gly Ile Gly Thr Gln Phe Thr Lys
145                 150                 155                 160
```

```
Gln Cys Glu Val Arg Gly Leu Val Val Cys Ser Ser Val Gly Ser
                165                 170                 175

Ile Asp Val Ala Glu Ile Val Ser Asp Thr Leu Leu Ile Ala Arg Lys
            180                 185                 190

Glu Phe Lys Gly Pro Lys Ala Lys Glu Ala Leu Lys Glu Ser Asn Gly
            195                 200                 205

Gly Ile Thr Tyr Lys Tyr Ala Asp Tyr Val Asn Gln Ala Thr Val Tyr
        210                 215                 220

Arg Ser Val Phe Asp Lys Leu His His Gly Cys Val Gly Ile Phe
225                 230                 235                 240

Pro Glu Gly Gly Ser His Asp Arg Thr Glu Leu Leu Pro Leu Lys Ala
                245                 250                 255

Gly Val Ala Ile Met Ala Leu Gly Ala Leu Ala Glu Asp Pro Ser Cys
                260                 265                 270

Gly Val Arg Ile Val Pro Cys Gly Leu Asn Tyr Phe His Ala His Lys
            275                 280                 285

Phe Arg Ser Arg Ala Val Val Glu Phe Gly Ser Pro Ile Ala Ile Pro
            290                 295                 300

Pro Asp Leu Val Glu Lys Tyr Lys Ala Gly Gly Glu Ala Lys Arg Glu
305                 310                 315                 320

Ala Val Lys Thr Val Leu Asp Ile Thr Ala Ala Gly Leu Lys Ser Val
                325                 330                 335

Thr Val Gln Val Gln Asp Phe Asp Thr Leu Met Leu Ile Gln Ala Ile
            340                 345                 350

Arg Arg Leu Tyr Arg Pro Pro Gly Lys Lys Ile Pro Leu Pro Met Val
            355                 360                 365

Val Glu Leu Asn Arg Arg Leu Val Tyr Ala Tyr Asn His Tyr Lys Asp
            370                 375                 380

Asp Pro Arg Ile Glu Glu Met Lys Gln Glu Ile Arg Lys Tyr Asn Lys
385                 390                 395                 400

Phe Leu Gln Ala Met Gly Leu Lys Asp His Gln Val Glu Lys Ala Arg
                405                 410                 415

Ile Ser Lys Ile Glu Ile Leu Gly Arg Leu Leu Tyr Arg Ser Ile Lys
            420                 425                 430

Leu Val Phe Leu Ser Ile Gly Cys Leu Pro Gly Leu Leu Phe Ser
            435                 440                 445

Pro Ile Phe Ile Ile Ser Lys Ser Ile Ser Lys Thr Lys Ala Lys Glu
            450                 455                 460

Ala Leu Lys Ala Ser Ser Val Lys Ile Lys Ala Asn Asp Val Val Ala
465                 470                 475                 480

Thr Trp Lys Val Leu Val Ala Met Gly Leu Thr Pro Val Leu Tyr Ile
                485                 490                 495

Leu Tyr Ser Leu Val Gly Ser Val Val Ile Arg Lys Leu Asp Leu Ile
            500                 505                 510

Ser Trp Phe Pro Thr Ile Leu Leu Pro Gly Leu Val Leu Ser Ile Ile
            515                 520                 525

Ile Thr Thr Ser Tyr Ala Ala Leu Ala Met Gly Glu Ala Gly Met Asp
            530                 535                 540

Ile Phe Lys Ser Leu Arg Pro Leu Ala Leu Ala Leu Asn Pro Ser Thr
545                 550                 555                 560

Lys Asn Ser Leu Leu Lys Leu Gln Asn Glu Arg Lys Arg Leu Val Leu
                565                 570                 575
```

-continued

```
Lys Ser Ser Glu Leu Val Thr Ser Leu Gly Pro Glu Leu Phe Pro Asp
                580                 585                 590

Phe Pro Glu Asn Ser Ile Leu Gln Gly Ser Asp Lys Phe Glu Asp Glu
            595                 600                 605

Glu Asn Tyr Glu Asn Glu Lys Arg Ser His Ser Arg Ser Thr Ser Ala
        610                 615                 620

Thr Ser Leu Ser Ala Met Ser Glu Gly Asp Gly Asp Glu Leu Val Arg
625                 630                 635                 640

Glu Val Arg Lys Gly Ala Ser Tyr Phe Pro Val Ser Thr Ile Ser Glu
                645                 650                 655

Asp Glu Asp Gln Ala Ile Ser Arg Val Gly Ser Glu Ala Ser Leu Ala
            660                 665                 670

Asp Ile Pro Leu Phe Gly Met Ser Arg Ser Gln Ser Gly Ala Ser Leu
        675                 680                 685

Ser Glu Ala Ser Thr His Gly Ser Ser Thr Gly Ala Asp Ala Glu Glu
690                 695                 700

Ala Lys Thr Glu Val Thr Arg Arg Ile Ala Leu Ala Met Glu Glu Lys
                705                 710                 715                 720

Arg Arg Glu Gln Asp Glu Glu
                725
```

<210> SEQ ID NO 11
<211> LENGTH: 1362
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1362)
<223> OTHER INFORMATION: S. cerevisiae-codon-optimized nucleotide
      sequence of H. subflexa fatty acyl reductase; mRNA-coding
      sequence.

<400> SEQUENCE: 11

```
atggttgtct tgacctccaa agaaactaag ccatctgttg ctgaatttta cgctggtaag      60
tctgttttca ttactggtgg tactggtttc ttgggtaagg ttttcattga aaagttgttg     120
tactcctgcc cagatatcgg taatatctac atgttgatca gagaaaagaa gggtttgtcc     180
gtttccgaaa gaatcaagca ctttttggat gatcctttgt tcaccagatt gaaagaaaaa     240
agaccagccg acttggaaaa gatcgttttg attccaggtg atattactgc tccagatttg     300
ggtattacct ccgaaaacga aaagatgttg atcgaaaagg tcagtgtcat tattcattct     360
gctgctaccg ttaagttcaa cgaaccattg ccaactgctt ggaagattaa cgttgaaggt     420
actagaatga tgttggcctt gtctagaaga atgaagagaa tcgaagtttt catccatatc     480
tctaccgctt acactaacac caacagagaa gttgttgacg aaatcttgta tccagctcca     540
gctgatattg atcaagttca ccaatatgtt aaggacggta tctctgaaga agaaactgaa     600
aaaatcttga cggtagacc aaacacttac actttcacta aggctttgac cgaacatttg     660
gttgctgaaa atcaagctta cgttccaacc attatcgtta ccatcagtt gttgctgcc     720
attaaggatg aacctattaa gggttggttg ggtaattggt atggtgctac aggtttgact     780
gtttttactg ctaagggttt gaacagagtt atctacggtc actcttctaa catcgttgat     840
ttgatcccag ttgattacgt tgccaacttg gttattgctg ctggtgctaa atcttctaag     900
tctactgaat tgaaggtcta caactgctgt tcttctgctt gtaacccaat tactatcggt     960
aagttgatgt ccatgtttgc tgaagatgct atcaagcaaa agtcttacgc tatgccattg    1020
```

```
ccaggttggt acatttttac taagtacaag tggttggtct tgttgttgac cattttgttc    1080
caagttattc cagcctacat taccgacttg tacagacatt tgattggtaa gaacccaaga    1140
tatatcaagt tgcaatcctt ggtcaatcaa accagatcct ccattgattt cttcaccaac    1200
cattcttggg ttatgaaggc tgatagagtc agagaattat tcgcttcttt gtctccagca    1260
gataagtact tgtttccatg tgatccagtc aacatcaatt ggagacaata tatccaagat    1320
tactgctggg gtgttagaca tttcttggaa aaaaagactt aa                       1362
```

<210> SEQ ID NO 12
<211> LENGTH: 453
<212> TYPE: PRT
<213> ORGANISM: Heliothis subflexa

<400> SEQUENCE: 12

```
Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
                20                  25                  30

Lys Val Phe Ile Glu Lys Leu Leu Tyr Ser Cys Pro Asp Ile Gly Asn
            35                  40                  45

Ile Tyr Met Leu Ile Arg Glu Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
                100                 105                 110

Lys Val Ser Val Ile Ile His Ser Ala Ala Thr Val Lys Phe Asn Glu
            115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
                180                 185                 190

Gly Ile Ser Glu Glu Glu Thr Glu Lys Ile Leu Asn Gly Arg Pro Asn
            195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
                260                 265                 270

Gly His Ser Ser Asn Ile Val Asp Leu Ile Pro Val Asp Tyr Val Ala
            275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
```

Lys Leu Met Ser Met Phe Ala Glu Asp Ala Ile Lys Gln Lys Ser Tyr
305                 310                 315                 320

Ala Met Pro Leu Pro Gly Trp Tyr Ile Phe Thr Lys Tyr Lys Trp Leu
            325                 330                 335

Val Leu Leu Leu Thr Ile Leu Phe Gln Val Ile Pro Ala Tyr Ile Thr
        340                 345                 350

Asp Leu Tyr Arg His Leu Ile Gly Lys Asn Pro Arg Tyr Ile Lys Leu
    355                 360                 365

Gln Ser Leu Val Asn Gln Thr Arg Ser Ser Ile Asp Phe Phe Thr Asn
370                 375                 380

His Ser Trp Val Met Lys Ala Asp Arg Val Arg Glu Leu Phe Ala Ser
385                 390                 395                 400

Leu Ser Pro Ala Asp Lys Tyr Leu Phe Pro Cys Asp Pro Val Asn Ile
            405                 410                 415

Asn Trp Arg Gln Tyr Ile Gln Asp Tyr Cys Trp Gly Val Arg His Phe
        420                 425                 430

Leu Glu Lys Lys Thr
    435                 440                 445

450

<210> SEQ ID NO 13
<211> LENGTH: 1368
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1368)
<223> OTHER INFORMATION: S. cerevisiae-codon-optimized nucleotide
      sequence of Helicoverpa armigera fatty acyl reductase; mRNA-coding
      sequence

<400> SEQUENCE: 13
atggttgtct tgacctccaa agaaactaag ccatctgttg ctgaatttta cgctggtaag      60
tctgttttca ttactggtgg tactggtttc ttgggtaagg ttttcattga aaagttgttg     120
tactcctgcc cagatatcgg taatatctac atgttgatca gagaaaagaa gggtttgtcc     180
gtttccgaaa gaatcaagca cttttttggat gatccttttgt tcaccagatt gaaagaaaaa     240
agaccagccg acttggaaaa gatcgttttg attccaggtg atattactgc tccagatttg     300
ggtattacct ccgaaaacga aaagatgttg atcgaaaagg tcagtgtcat tattcattct     360
gctgctaccg ttaagttcaa cgaaccattg ccaactgctt ggaagattaa cgttgaaggt     420
actagaatga tgttggcctt gtctagaaga atgaagagaa tcgaagtttt catccatatc     480
tctaccgctt acactaacac caacagaaa gttgttgacg aaatcttgta tccagctcca     540
gctgatattg atcaagttca cagatatgtt aaggacggta tctctgaaga agaaactgaa     600
aaaatcttga acggtagacc aaacacttac actttcacta aggctttgac cgaacatttg     660
gttgctgaaa tcaagcttta cgttccaacc attatcgtta gaccatcagt tgttgctgcc     720
attaaggatg aacctattaa gggttggttg ggtaattggt atggtgctac aggttttgact     780 gtttttactg ctaagggttt gaacagagtt atctacggtc actcttctaa catcgttgat     840
ttgatcccag ttgattacgt tgccaacttg gttattgctg ctggtgctaa atcttctaag     900
tctactgaat tgaaggtcta caactgctgt tcttctgctt gtaacccaat tactatcggt     960
aagttgatgt ccatgtttgc tgaagatgct atcaagcaaa agtcttacgc tatgccattg    1020

```
ccaggttggt acattttac taagtacaag tggttggtct tgttgttgac cattttgttc    1080
caagttattc cagcctacat taccgacttg tacagacatt tgattggtaa gaacccaaga    1140
tatatcaagt tgcaatcctt ggtcaatcaa accagatcct ccattgattt cttcacctct    1200
cattcttggg ttatgaaggc tgatagagtc agagaattat tcgcttcttt gtctccagca    1260
gataagtact tgtttccatg tgatccaacc gatattaact ggacccatta cattcaagat    1320
tactgctggg gtgttagaca tttcttggaa aaaaaaagct acgaataa               1368
```

<210> SEQ ID NO 14
<211> LENGTH: 455
<212> TYPE: PRT
<213> ORGANISM: Helicoverpa armigera

<400> SEQUENCE: 14

```
Met Val Val Leu Thr Ser Lys Glu Thr Lys Pro Ser Val Ala Glu Phe
1               5                  10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
            180                 185                 190

Gly Ile Ser Glu Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320
```

Lys Leu Met Ser Met Phe Ala Glu Asp Ala Ile Lys Gln Lys Ser Tyr
            325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
            355                 360                 365

Asp Leu Tyr Arg His Leu Ile Gly Lys Asn Pro Arg Tyr Ile Lys Leu
            370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
            405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
            435                 440                 445

Leu Glu Lys Lys Ser Tyr Glu
            450                 455

<210> SEQ ID NO 15
<211> LENGTH: 1371
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1371)
<223> OTHER INFORMATION: S. cerevisiae-codon-optimized nucleotide
      sequence of H. assulta fatty acyl reductase; mRNA-coding sequence.

<400> SEQUENCE: 15
atggttgtct tgacctccaa agaaactaag ccatctgttg ctgaatttta cgctggtaag      60
tctgttttca ttactggtgg tactggtttc ttgggtaaga tcttcattga aaagttgttg     120
tactcctgcc agatatcgg taatatctac atgttgatca gagaaaagaa gggtttgtcc     180
gtttccgaaa gaatcaagca atttttggat gacccttgt tcaccagatt gaagaaaaa     240 agaccagccg acttggaaaa gatcgttttg attccaggtg atattactgc tccagatttg     300
ggtattacct ccgaaaacga aaagatgttg atcgaaaagg tcagtgtcat tattcattct     360
gctgctaccg ttaagttcaa cgaaccattg ccaactgctt ggaagattaa cgttgaaggt     420
actagaatga tgttggcctt gtctagaaga atgaagagaa tcgaagtttt catccatatc     480
tctaccgctt acactaacac caacagagaa gttgttgacg aaatcttgta tccagctcca     540
gctgatattg atcaagttca ccaatatgtt aaggacggta tctctgaaga agaaactgaa     600
aaaatcttga acggtagacc aaacacttac actttcacta aggctttgac cgaacatttg     660
gttgctgaaa tcaagctta cgttccaacc attatcgtta gaccatcagt tgttgctgcc     720
attaaggatg aacctattaa gggttggttg gtaattggt atggtgctac aggtttgact     780 gttttactg ctaagggttt gaacagagtt atctacggtc attcctctta catcgttgat     840
ttgatcccag ttgattacgt tgccaacttg gttattgctc tggtgctaa atcttctaag     900 tctactgaat tgaaggtcta caactgctgt tcttctgctt gtaacccaat tactatcggt     960
aagttgatgt ccatgtttgc tgaagatgct atcaagcaaa agtcttacgc tatgccattg    1020
ccaggttggt atgttttac aaagtacaag tggttggtct tgttgttgac catttttgttc    1080

-continued

```
caagttattc cagcctacat taccgacttg tacagacatt tgattggtaa gaacccaaga    1140
tatatcaagt tgcaatcctt ggtcaatcaa accagatcct ccattgattt cttcacctct    1200
cattcttggg ttatgaaggc tgatagagtc agagaattat tcgcttcttt gtctccagca    1260
gataagtact tgtttccatg tgatccaacc gatattaact ggacccatta cattcaagat    1320
tactgctggg gtgttagaca cttcttggaa aaaaagacta ccaacaagta a             1371
```

<210> SEQ ID NO 16
<211> LENGTH: 456
<212> TYPE: PRT
<213> ORGANISM: Helicoverpa assulta

<400> SEQUENCE: 16

```
Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Ile Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
50                  55                  60

Ile Lys Gln Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
```

```
            325                 330                 335
Ala Met Pro Leu Pro Gly Trp Tyr Val Phe Thr Lys Tyr Lys Trp Leu
            340                 345                 350

Val Leu Leu Leu Thr Ile Leu Phe Gln Val Ile Pro Ala Tyr Ile Thr
            355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
            435                 440                 445

Leu Glu Lys Lys Thr Thr Asn Lys
    450                 455
```

<210> SEQ ID NO 17
<211> LENGTH: 1086
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1086)
<223> OTHER INFORMATION: S. cerevisiae codon-optimized nucleotide
      sequence of delat9 desaturase from Drosophila melanogaster Dmd9

<400> SEQUENCE: 17

```
atggctccat actctagaat ctaccaccaa gataagtcct ctagagaaac tggtgttttg      60
ttcgaagatg atgctcaaac cgttgattct gatttgacta ccgatagatt ccaattgaag     120
agagccgaaa aagaagatt gccattggtt tggagaaaca tcatcttgtt cgctttggtt     180
catttggctg ccttgtatgg tttacattcc attttcacta gagctaagtt ggctactact     240
ttgtttgctg ctggtttgta cattatcggt atgttgggtg ttactgctgg tgctcataga     300
ttgtgggctc atagaactta caaagctaaa tggccttttga gattgttgtt ggtcatcttc     360
aacaccattg ctttccaaga tgctgtttat cattgggcca gagatcatag agttcatcac     420
aaatactctg aaaccgatgc tgatccacat aatgctacta gaggtttctt cttctctcat     480
gttggttggt gttgtgcaa gaaacaccca gatatcaaag aaaagggtag aggtttggat     540
tgtccgatt tgagagctga tccaatcttg atgtttcaaa gaaagcacta ctacatcttg     600
atgccattgg cttgttttgt tttgccaacc gttattccaa tggtctactg gaacgaaact     660
ttggcttctt cttggtttgt tgctactatg ttcagatggt gcttccaatt gaatatgacc     720
tggttggtta attccgctgc tcataagttt ggtaatagac atacgataa gaccatgaac     780
ccaactcaaa atgctttcgt ttctgctttc acttttggtg aaggttggca taattaccat     840
catgctttc catgggatta caagactgct gaatggggtt gttactcttt gaacattact     900
accgccttca ttgatttgtt cgctaaaatt ggttgggcct acgatttgaa aactgttgct     960
ccagatgtta tccaaagaag agttttgaga actggtgatg ttctcatga attgtgggt    1020
tggggtgata aggatttgac cgctgaagat gctagaaacg ttttgttggt tgacaagtcc    1080
agataa                                                                1086
```

<210> SEQ ID NO 18
<211> LENGTH: 361
<212> TYPE: PRT
<213> ORGANISM: Drosophila melanogaster

<400> SEQUENCE: 18

Met Ala Pro Tyr Ser Arg Ile Tyr His Gln Asp Lys Ser Ser Arg Glu
1               5                   10                  15

Thr Gly Val Leu Phe Glu Asp Asp Ala Gln Thr Val Asp Ser Asp Leu
            20                  25                  30

Thr Thr Asp Arg Phe Gln Leu Lys Arg Ala Glu Lys Arg Arg Leu Pro
        35                  40                  45

Leu Val Trp Arg Asn Ile Ile Leu Phe Ala Leu Val His Leu Ala Ala
    50                  55                  60

Leu Tyr Gly Leu His Ser Ile Phe Thr Arg Ala Lys Leu Ala Thr Thr
65                  70                  75                  80

Leu Phe Ala Ala Gly Leu Tyr Ile Ile Gly Met Leu Gly Val Thr Ala
                85                  90                  95

Gly Ala His Arg Leu Trp Ala His Arg Thr Tyr Lys Ala Lys Trp Pro
            100                 105                 110

Leu Arg Leu Leu Leu Val Ile Phe Asn Thr Ile Ala Phe Gln Asp Ala
        115                 120                 125

Val Tyr His Trp Ala Arg Asp His Arg Val His His Lys Tyr Ser Glu
    130                 135                 140

Thr Asp Ala Asp Pro His Asn Ala Thr Arg Gly Phe Phe Phe Ser His
145                 150                 155                 160

Val Gly Trp Leu Leu Cys Lys Lys His Pro Asp Ile Lys Glu Lys Gly
                165                 170                 175

Arg Gly Leu Asp Leu Ser Asp Leu Arg Ala Asp Pro Ile Leu Met Phe
            180                 185                 190

Gln Arg Lys His Tyr Tyr Ile Leu Met Pro Leu Ala Cys Phe Val Leu
        195                 200                 205

Pro Thr Val Ile Pro Met Val Tyr Trp Asn Glu Thr Leu Ala Ser Ser
    210                 215                 220

Trp Phe Val Ala Thr Met Phe Arg Trp Cys Phe Gln Leu Asn Met Thr
225                 230                 235                 240

Trp Leu Val Asn Ser Ala Ala His Lys Phe Gly Asn Arg Pro Tyr Asp
                245                 250                 255

Lys Thr Met Asn Pro Thr Gln Asn Ala Phe Val Ser Ala Phe Thr Phe
            260                 265                 270

Gly Glu Gly Trp His Asn Tyr His His Ala Phe Pro Trp Asp Tyr Lys
        275                 280                 285

Thr Ala Glu Trp Gly Cys Tyr Ser Leu Asn Ile Thr Thr Ala Phe Ile
    290                 295                 300

Asp Leu Phe Ala Lys Ile Gly Trp Ala Tyr Asp Leu Lys Thr Val Ala
305                 310                 315                 320

Pro Asp Val Ile Gln Arg Arg Val Leu Arg Thr Gly Asp Gly Ser His
                325                 330                 335

Glu Leu Trp Gly Trp Gly Asp Lys Asp Leu Thr Ala Glu Asp Ala Arg
            340                 345                 350

Asn Val Leu Leu Val Asp Lys Ser Arg
        355                 360

<210> SEQ ID NO 19

```
<211> LENGTH: 335
<212> TYPE: PRT
<213> ORGANISM: Choristoneura rosaceana

<400> SEQUENCE: 19

Met Ala Pro Asn Val Glu Asp Met Glu Ser Asp Leu Pro Glu Ser Glu
1               5                   10                  15

Glu Lys Leu Glu Lys Leu Val Ala Pro Gln Ala Ala Pro Arg Lys Tyr
                20                  25                  30

Gln Ile Ile Tyr Thr Asn Leu Thr Phe Gly Tyr Trp His Ile Ala
        35                  40                  45

Gly Leu Tyr Gly Leu Tyr Leu Cys Phe Thr Ser Ala Lys Trp Gln Thr
    50                  55                  60

Ile Ile Leu Ala Leu Ile Leu Asn Glu Met Ala Ile Leu Gly Ile Thr
65                  70                  75                  80

Ala Gly Ala His Arg Leu Trp Ala His Arg Ser Tyr Lys Ala Thr Val
                85                  90                  95

Pro Leu Gln Ile Ile Leu Ile Ile Phe Asn Ser Leu Ser Phe Gln Asn
                100                 105                 110

Ser Ala Ile His Trp Ile Arg Asp His Arg Met His His Lys Tyr Ser
            115                 120                 125

Asp Thr Asp Gly Asp Pro His Asn Ala Ser Arg Gly Phe Phe Tyr Ser
130                 135                 140

His Val Gly Trp Leu Leu Val Lys Lys His Pro Glu Val Lys Lys Arg
145                 150                 155                 160

Ala Lys Thr Ile Asp Met Ser Asp Ile Tyr Ser Asn Pro Ile Leu Arg
                165                 170                 175

Phe Gln Lys Lys Tyr Ala Ile Pro Phe Ile Gly Met Ile Cys Phe Val
                180                 185                 190

Leu Pro Thr Ile Ile Pro Met Tyr Phe Trp Gly Glu Thr Leu Ser Asn
            195                 200                 205

Ala Trp His Ile Thr Met Leu Arg Tyr Val Phe Ser Leu Asn Ser Ile
        210                 215                 220

Phe Leu Val Asn Ser Ala Ala His Leu Tyr Gly Tyr Arg Pro Tyr Asp
225                 230                 235                 240

Lys Asn Ile Leu Pro Ala Glu Asn Lys Met Thr Phe Ile Ala Cys Leu
                245                 250                 255

Gly Glu Asn Phe His Asn Tyr His His Val Phe Pro Trp Asp Tyr Arg
            260                 265                 270

Ala Ser Glu Leu Gly Asn Ile Gly Met Asn Trp Thr Ala Lys Phe Ile
        275                 280                 285

Asp Phe Phe Ala Trp Ile Gly Trp Ala Tyr Asp Leu Lys Thr Ala Ser
290                 295                 300

Asp Glu Asn Ile Lys Ser Arg Met Lys Arg Thr Gly Asp Gly Thr Asp
305                 310                 315                 320

Val Ser Gly Gln Lys Tyr Ser Cys Glu Ser Ser Glu Val Leu Gln
                325                 330                 335

<210> SEQ ID NO 20
<211> LENGTH: 334
<212> TYPE: PRT
<213> ORGANISM: Choristoneura parallela

<400> SEQUENCE: 20

Met Ala Pro Asn Val Glu Asp Met Glu Ser Asp Met Pro Glu Ser Glu
1               5                   10                  15
```

Lys Trp Glu Lys Leu Val Ala Pro Gln Ala Pro Arg Lys Tyr Glu
            20                  25                  30

Ile Ile Tyr Thr Asn Leu Leu Thr Phe Gly Tyr Gly His Ile Ala Gly
        35                  40                  45

Leu Tyr Gly Leu Tyr Leu Cys Phe Thr Ser Ala Lys Trp Gln Thr Val
50                  55                  60

Ile Leu Ala Ile Ile Leu Asn Glu Met Ala Ile Leu Gly Ile Thr Ala
65                  70                  75                  80

Gly Ala His Arg Leu Trp Ser His Arg Ser Tyr Lys Ala Ala Val Pro
                85                  90                  95

Leu Gln Ile Ile Leu Met Ile Phe Asn Ser Leu Ala Phe Gln Asn Ser
            100                 105                 110

Ala Ile Asn Trp Val Arg Asp His Arg Met His His Lys Tyr Ser Asp
            115                 120                 125

Thr Asp Gly Asp Pro His Asn Ala Ser Arg Gly Phe Phe Tyr Ser His
130                 135                 140

Val Gly Trp Leu Leu Val Lys Lys His Pro Glu Val Lys Lys Arg Gly
145                 150                 155                 160

Lys Met Ile Asp Met Ser Asp Ile Tyr Ser Asn Pro Val Leu Arg Phe
                165                 170                 175

Gln Lys Lys Tyr Ala Ile Pro Phe Ile Gly Met Ile Cys Phe Val Leu
            180                 185                 190

Pro Thr Ile Ile Pro Met Tyr Phe Trp Gly Glu Thr Leu Ser Asn Ala
            195                 200                 205

Trp His Ile Thr Met Leu Arg Tyr Val Phe Ser Leu Asn Ser Ile Phe
            210                 215                 220

Leu Val Asn Ser Ala Ala His Leu Tyr Gly Tyr Arg Pro Tyr Asp Lys
225                 230                 235                 240

Asn Ile Leu Pro Ala Glu Asn Lys Ile Ala Leu Ile Ala Cys Leu Gly
                245                 250                 255

Asp Ser Phe His Asn Tyr His His Val Phe Pro Trp Asp Tyr Arg Ala
            260                 265                 270

Ser Glu Leu Gly Asn Ile Gly Met Asn Trp Thr Ala Gln Phe Ile Asp
            275                 280                 285

Phe Phe Ala Trp Ile Gly Trp Ala Tyr Asp Leu Lys Thr Ala Ser Asp
290                 295                 300

Glu Asn Ile Asn Ser Arg Met Lys Arg Thr Gly Asp Gly Thr Asp Ile
305                 310                 315                 320

Ser Gly Gln Lys Tyr Ser Cys Glu Ser Ser Glu Val Leu Gln
                325                 330

<210> SEQ ID NO 21
<211> LENGTH: 1830
<212> TYPE: DNA
<213> ORGANISM: Yarrowia lipolytica

<400> SEQUENCE: 21
atgtctgacg acaagcacac tttcgacttt atcattgtcg gtggaggaac cgccggcccc    60
actctcgccc ggcgactggc cgatgcctgg atctccggta agaagctcaa ggtgctcctg   120
ctcgagtccg gcccctcttc cgagggtgtt gatgatattc gatgccccgg taactgggtc   180
aacaccatcc actccgagta cgactggtcc tacgaggtcg acgagcctta cctgtctact   240
gatggcgagg agcgacgact ctgtggtatc ccccgaggcc attgtctggg tggatcctct   300

```
tgtctgaaca cctctttcgt catccgagga acccgaggtg atttcgaccg aatcgaagag    360
gagaccggcg ctaagggctg gggttgggat gatctgttcc cctacttccg aaagcacgag    420
tgttacgtgc cccagggatc tgcccacgag cccaagctca ttgacttcga cacctacgac    480
tacaagaagt tccacggtga ctctggtcct atcaaggtcc agccttacga ctacgcgccc    540
atctccaaga agttctctga gtctctggct tctttcggct acccttataa ccccgagatc    600
ttcgtcaacg gaggagcccc caggggttgg ggtcacgttg ttcgttccac ctccaacggt    660
gttcgatcca ccggctacga cgctcttgtc cacgccccca gaacctcga  cattgtgact    720 ggccacgctg tcaccaagat tctctttgag aagatcggtg caagcagac  cgccgttggt    780 gtcgagacct acaaccgagc tgccgaggag gctggcccta cctacaaggc cgatacgag   840 gtggttgtgt gctgcggctc ttatgcctct ccccagcttc tgatggtttc cggtgttgga    900
cccaagaagg agctcgagga ggttggtgtc aaggacatca ttttggactc tccttacgtt    960
ggaaagaacc tgcaggacca tcttatctgc ggtatctttg tcgaaattaa ggagcccgga   1020
tacacccgag accaccagtt cttcgacgac gagggactcg acaagtccac cgaggagtgg   1080
aagaccaagc gaaccggttt cttctccaat cctccccagg gcattttctc ttacggccga   1140
atcgacaacc tgctcaagga tgatcccgtc tggaaggagg cctgcgagaa gcagaaggct   1200
ctcaaccctc gacgagaccc catgggtaac gatccctctc agccccattt cgagatctgg   1260
aatgctgagc tctacatcga gctagagatg acccaggctc ccgacgaggg ccagtccgtc   1320
atgaccgtca tcggtgagat tcttcctcct cgatccaagg gttacgtcaa gctgctgtcc   1380
cccgacccta tggagaaccc cgagattgtc acaactacc  tgcaggaccc tgttgacgct   1440
cgagtcttcg ctgccatcat gaagcacgcc gccgacgttg ccaccaacgg tgctggcacc   1500
aaggacctct caaggctcg  atggcccccg gagtccaagc ccttcgagga aatgtccatc   1560
gaggaatggg agacttacgt ccgagacaag tctcacacct gtttccaccc ctgtggtact   1620
gtcaagcttg gtggtgctaa tgataaggag gccgttgttg acgagcgact ccgagtcaag   1680
ggtgtcgacg gcctgcgagt tgccgacgtc tctgtccttc cccgagtccc caacggacac   1740
acccaggctt tgcctacgc  tgttggtgag aaggctgccg acctcatcct tgccgacatt   1800
gctggaaagg atctccgacc tcgaatctaa                                    1830
```

<210> SEQ ID NO 22
<211> LENGTH: 609
<212> TYPE: PRT
<213> ORGANISM: Yarrowia lipolytica

<400> SEQUENCE: 22

Met Ser Asp Asp Lys His Thr Phe Asp Phe Ile Ile Val Gly Gly Gly
1               5                   10                  15

Thr Ala Gly Pro Thr Leu Ala Arg Arg Leu Ala Asp Ala Trp Ile Ser
            20                  25                  30

Gly Lys Lys Leu Lys Val Leu Leu Glu Ser Gly Pro Ser Ser Glu
        35                  40                  45

Gly Val Asp Asp Ile Arg Cys Pro Gly Asn Trp Val Asn Thr Ile His
    50                  55                  60

Ser Glu Tyr Asp Trp Ser Tyr Glu Val Asp Pro Tyr Leu Ser Thr
65                  70                  75                  80

Asp Gly Glu Glu Arg Arg Leu Cys Gly Ile Pro Arg Gly His Cys Leu
                85                  90                  95

Gly Gly Ser Ser Cys Leu Asn Thr Ser Phe Val Ile Arg Gly Thr Arg

-continued

```
              100                 105                 110
Gly Asp Phe Asp Arg Ile Glu Glu Thr Gly Ala Lys Gly Trp Gly
            115                 120                 125

Trp Asp Leu Phe Pro Tyr Phe Arg Lys His Glu Cys Tyr Val Pro
        130                 135                 140

Gln Gly Ser Ala His Glu Pro Lys Leu Ile Asp Phe Asp Thr Tyr Asp
145                 150                 155                 160

Tyr Lys Lys Phe His Gly Asp Ser Gly Pro Ile Lys Val Gln Pro Tyr
                165                 170                 175

Asp Tyr Ala Pro Ile Ser Lys Lys Phe Ser Glu Ser Leu Ala Ser Phe
            180                 185                 190

Gly Tyr Pro Tyr Asn Pro Glu Ile Phe Val Asn Gly Ala Pro Gln
        195                 200                 205

Gly Trp Gly His Val Val Arg Ser Thr Ser Asn Gly Val Arg Ser Thr
        210                 215                 220

Gly Tyr Asp Ala Leu Val His Ala Pro Lys Asn Leu Asp Ile Val Thr
225                 230                 235                 240

Gly His Ala Val Thr Lys Ile Leu Phe Glu Lys Ile Gly Gly Lys Gln
                245                 250                 255

Thr Ala Val Gly Val Glu Thr Tyr Asn Arg Ala Ala Glu Glu Ala Gly
            260                 265                 270

Pro Thr Tyr Lys Ala Arg Tyr Glu Val Val Val Cys Cys Gly Ser Tyr
        275                 280                 285

Ala Ser Pro Gln Leu Leu Met Val Ser Gly Val Gly Pro Lys Lys Glu
        290                 295                 300

Leu Glu Glu Val Gly Val Lys Asp Ile Ile Leu Asp Ser Pro Tyr Val
305                 310                 315                 320

Gly Lys Asn Leu Gln Asp His Leu Ile Cys Gly Ile Phe Val Glu Ile
                325                 330                 335

Lys Glu Pro Gly Tyr Thr Arg Asp His Gln Phe Phe Asp Glu Gly
            340                 345                 350

Leu Asp Lys Ser Thr Glu Glu Trp Lys Thr Arg Thr Gly Phe Phe
        355                 360                 365

Ser Asn Pro Pro Gln Gly Ile Phe Ser Tyr Gly Arg Ile Asp Asn Leu
        370                 375                 380

Leu Lys Asp Asp Pro Val Trp Lys Glu Ala Cys Glu Lys Gln Lys Ala
385                 390                 395                 400

Leu Asn Pro Arg Arg Asp Pro Met Gly Asn Asp Pro Ser Gln Pro His
                405                 410                 415

Phe Glu Ile Trp Asn Ala Glu Leu Tyr Ile Glu Leu Glu Met Thr Gln
            420                 425                 430

Ala Pro Asp Glu Gly Gln Ser Val Met Thr Val Ile Gly Glu Ile Leu
        435                 440                 445

Pro Pro Arg Ser Lys Gly Tyr Val Lys Leu Leu Ser Pro Asp Pro Met
        450                 455                 460

Glu Asn Pro Glu Ile Val His Asn Tyr Leu Gln Asp Pro Val Asp Ala
465                 470                 475                 480

Arg Val Phe Ala Ala Ile Met Lys His Ala Ala Asp Val Ala Thr Asn
                485                 490                 495

Gly Ala Gly Thr Lys Asp Leu Val Lys Ala Arg Trp Pro Pro Glu Ser
            500                 505                 510

Lys Pro Phe Glu Glu Met Ser Ile Glu Glu Trp Glu Thr Tyr Val Arg
        515                 520                 525
```

```
Asp Lys Ser His Thr Cys Phe His Pro Cys Gly Thr Val Lys Leu Gly
        530                 535                 540

Gly Ala Asn Asp Lys Glu Ala Val Val Asp Glu Arg Leu Arg Val Lys
545                 550                 555                 560

Gly Val Asp Gly Leu Arg Val Ala Asp Val Ser Val Leu Pro Arg Val
                565                 570                 575

Pro Asn Gly His Thr Gln Ala Phe Ala Tyr Ala Val Gly Glu Lys Ala
            580                 585                 590

Ala Asp Leu Ile Leu Ala Asp Ile Ala Gly Lys Asp Leu Arg Pro Arg
        595                 600                 605

Ile
```

<210> SEQ ID NO 23
<211> LENGTH: 1437
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1437)
<223> OTHER INFORMATION: Y.lipolytica codon-optimized nucleotide
      sequence of fatty acyl reductase from Bicyclus anynana Ban-wFAR2

<400> SEQUENCE: 23

```
atgtaccgaa acgtgaacaa caactacaag ggccactctg tgtacaccaa cggcgctggc      60
tctcgagtga agtctctgct gtcctctgcc accgacaaca ccaacgagta ccagtctatc     120
gccgagtgct acaagggaca gtccgtgttc atcaccggcg gcaccggctt cgtcggcaag     180
gtgctgctcg agaagctgct gtactcttgc cccggcatcg acaaggtgta cctgctggtg     240
cgagagactc agggcgccac cgctcaccag cgaatgcaga agctcctgga gaacccgcc      300
ttctcgcgaa tcaaggaaga gaaccctcag gccttcgaga aggtgatccc catcgtgggc     360
gacatcaccc cagcctcagct gggcatcatg gccgagaacg aggaactgct gattaaggaa    420
gtgtctttcg tctaccacgt ggccgccacc accaagttca cgagactct ggacattgcc      480
atgaacgtga acgtggccgg aaccggacga gtgctggacc tgtctaagcg aatggaaaac    540
atcaaggcct tcgtgtacgt gtctaccgcc tactctaaca ccgaccgaga ggtggtggaa    600
gaggtgctgt acccccgctcc tgtgtctctg aacgaggtgc acaagctgct gaagatcggc    660
atcaccgacg ctcaggtgaa ggaactgatc aagggacgac ccaacaccta caccttcacc    720
aaggctctgg ctgagaacct ggtggccgac aaccacggac acgtgcccgc catcatcgtg    780
cgaccctcta cgtgtcctc gtctaagaag gaacccatca ccggatggat cgactcttgg    840
tacgcgcca ccttcctggc caccgtgacc atgaagggct tcaaccgagt gttcgtgtcg    900
tcttacgagt acaacctgga cttcatcccc gtggactacg tgtccaacct gatcatcgtg    960
gccgctgctc gatgcaagtg ctctgacaag gtggacgtgt acaactcttc tacctccggc    1020
gaaaaccctc tgaagattgg cgccttcttc gacgacatca ttgcctactc ttgcaagcac    1080
aagttctacg acatccctct gcctatggcc tacctgactc gataccgatg ggtcatgttc    1140
ctgatcaccc tgctgctgca gacctgcct gcctatatcg ccgacctgtt cctgctgatc    1200
gtgggcaaga gccccgata cgtcaagctg gcctctaaga tctctgccgc tcacgaggtc    1260
ctggactact cccctctcg aacctggtct atgtctgccc gacagaccac cgctctgttc    1320
cagtctctgt ctccctcgga ccgagatcag tttccttgcg accccaccga catcgactgg    1380
```

```
aaggagtaca tcgtcaccta ctgccaggga atccgacagt tcctgtgcaa gtcttaa        1437
```

<210> SEQ ID NO 24
<211> LENGTH: 478
<212> TYPE: PRT
<213> ORGANISM: Bicyclus anynana

<400> SEQUENCE: 24

```
Met Tyr Arg Asn Val Asn Asn Tyr Lys Gly His Ser Val Tyr Thr
1               5                   10                  15

Asn Gly Ala Gly Ser Arg Val Lys Ser Leu Leu Ser Ser Ala Thr Asp
            20                  25                  30

Asn Thr Asn Glu Tyr Gln Ser Ile Ala Glu Cys Tyr Lys Gly Gln Ser
        35                  40                  45

Val Phe Ile Thr Gly Gly Thr Gly Phe Val Gly Lys Val Leu Leu Glu
    50                  55                  60

Lys Leu Leu Tyr Ser Cys Pro Gly Ile Asp Lys Val Tyr Leu Leu Val
65              70                  75                  80

Arg Glu Thr Gln Gly Ala Thr Ala His Gln Arg Met Gln Lys Leu Leu
                85                  90                  95

Glu Glu Pro Ala Phe Ser Arg Ile Lys Glu Glu Asn Pro Gln Ala Phe
            100                 105                 110

Glu Lys Val Ile Pro Ile Val Gly Asp Ile Thr Gln Pro Gln Leu Gly
        115                 120                 125

Ile Met Ala Glu Asn Glu Glu Leu Leu Ile Lys Glu Val Ser Phe Val
    130                 135                 140

Tyr His Val Ala Ala Thr Thr Lys Phe Asn Glu Thr Leu Asp Ile Ala
145                 150                 155                 160

Met Asn Val Asn Val Ala Gly Thr Gly Arg Val Leu Asp Leu Ser Lys
                165                 170                 175

Arg Met Glu Asn Ile Lys Ala Phe Val Tyr Val Ser Thr Ala Tyr Ser
            180                 185                 190

Asn Thr Asp Arg Glu Val Val Glu Glu Val Leu Tyr Pro Ala Pro Val
        195                 200                 205

Ser Leu Asn Glu Val His Lys Leu Leu Lys Ile Gly Ile Thr Asp Ala
    210                 215                 220

Gln Val Lys Glu Leu Ile Lys Gly Arg Pro Asn Thr Tyr Thr Phe Thr
225                 230                 235                 240

Lys Ala Leu Ala Glu Asn Leu Val Ala Asp Asn His Gly His Val Pro
                245                 250                 255

Ala Ile Ile Val Arg Pro Ser Ile Val Ser Ser Ser Lys Lys Glu Pro
            260                 265                 270

Ile Thr Gly Trp Ile Asp Ser Trp Tyr Gly Ala Thr Phe Leu Ala Thr
        275                 280                 285

Val Thr Met Lys Gly Phe Asn Arg Val Phe Val Ser Ser Tyr Glu Tyr
    290                 295                 300

Asn Leu Asp Phe Ile Pro Val Asp Tyr Val Ser Asn Leu Ile Ile Val
305                 310                 315                 320

Ala Ala Ala Arg Cys Lys Cys Ser Asp Lys Val Asp Val Tyr Asn Ser
                325                 330                 335

Ser Thr Ser Gly Glu Asn Pro Leu Lys Ile Gly Ala Phe Phe Asp Asp
            340                 345                 350

Ile Ile Ala Tyr Ser Cys Lys His Lys Phe Tyr Asp Ile Pro Leu Pro
        355                 360                 365
```

```
Met Ala Tyr Leu Thr Arg Tyr Arg Trp Val Met Phe Leu Ile Thr Leu
            370                 375                 380

Leu Leu Gln Thr Leu Pro Ala Tyr Ile Ala Asp Leu Phe Leu Leu Ile
385                 390                 395                 400

Val Gly Lys Lys Pro Arg Tyr Val Lys Leu Ala Ser Lys Ile Ser Ala
                405                 410                 415

Ala His Glu Val Leu Asp Tyr Phe Pro Ser Arg Thr Trp Ser Met Ser
                420                 425                 430

Ala Arg Gln Thr Thr Ala Leu Phe Gln Ser Leu Ser Pro Ser Asp Arg
            435                 440                 445

Asp Gln Phe Pro Cys Ala Pro Thr Asp Ile Asp Trp Lys Glu Tyr Ile
450                 455                 460

Val Thr Tyr Cys Gln Gly Ile Arg Gln Phe Leu Cys Lys Ser
465                 470                 475
```

<210> SEQ ID NO 25
<211> LENGTH: 22
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(22)
<223> OTHER INFORMATION: SEQ ID NO: 25 PR-141n = uracil

<400> SEQUENCE: 25
agaacagcng aagcttcgta cg                                          22

<210> SEQ ID NO 26
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: PR-142n = uracil

<400> SEQUENCE: 26
aggccacnag tggatctgat atcac                                       25

<210> SEQ ID NO 27
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-10851 (Atrd11 expression cassette _fw) n =
      uracil

<400> SEQUENCE: 27
agtgcaggng acgcagtagg atgtcctgc                                   29

<210> SEQ ID NO 28
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: PR-10853 (Hs_Far expression cassette _fw)n = uracil

<400> SEQUENCE: 28
acctgcacna gagaccgggt tgg                                              23

<210> SEQ ID NO 29
<211> LENGTH: 33
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(33)
<223> OTHER INFORMATION: PR-10655 (EpiVecYL _fw)n = uracil

<400> SEQUENCE: 29
acccattgcn gtagatatgt cttgtgtgta agg                                   33

<210> SEQ ID NO 30
<211> LENGTH: 32
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(32)
<223> OTHER INFORMATION: PR-10656 (EpiVecYL _rev)n = uracil

<400> SEQUENCE: 30
atcatgtaan tagttatgtc acgcttacat tc                                    32

<210> SEQ ID NO 31
<211> LENGTH: 22
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(22)
<223> OTHER INFORMATION: PR-10702 (delta-pex10YL_up _fw)

<400> SEQUENCE: 31
cattgtaact agtcctggag gg                                               22

<210> SEQ ID NO 32
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: PR-10703 (delta-pex10YL_up _rev)n = uracil

<400> SEQUENCE: 32
acgaagttan tttgagccga ggcagatttg                                       30

<210> SEQ ID NO 33
<211> LENGTH: 31
<212> TYPE: DNA
<213> ORGANISM: Artificial sequence
<220> FEATURE:
<223> OTHER INFORMATION: Primer

```
<220> FEATURE:
<221> NAME/KEY: misc_feature
<222> LOCATION: (1)..(31)
<223> OTHER INFORMATION: PR-10704 (dekta-pex10YL_down _fw)n = uracil

<400> SEQUENCE: 33
acgaagttat ntgacgaggt ctggatggaa g                                   31

<210> SEQ ID NO 34
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: PR-10705 (delta-pex10YL_down _rev)

<400> SEQUENCE: 34
cattgctaag aatccaaact ggag                                           24

<210> SEQ ID NO 35
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(19)
<223> OTHER INFORMATION: PR-10767 (NatMxSynYL-start _rev_new)

<400> SEQUENCE: 35
tcatggacat ggcatagac                                                 19

<210> SEQ ID NO 36
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: PR-11047 (NatMxSynYL-end _rev_new)n = uracil

<400> SEQUENCE: 36
aataacttcg natagcatac attatacgaa gttatcgagc gtcccaaaac c             51

<210> SEQ ID NO 37
<211> LENGTH: 31
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: PR-11110 (E.coli backboneUSER _fw)

<400> SEQUENCE: 37
atcgcgtgca ttcgcggccg catttaaatc c                                   31

<210> SEQ ID NO 38
<211> LENGTH: 36
<212> TYPE: DNA
<213> ORGANISM: Artificial sequence
<220> FEATURE:
```

<223> OTHER INFORMATION: Primer
<220> FEATURE:
<221> NAME/KEY: misc_feature
<222> LOCATION: (1)..(36)
<223> OTHER INFORMATION: PR-11111 (E.coli backboneUSER _rev)

<400> SEQUENCE: 38
tcgcacgcat tcgcggccgc aaatttaaat aaaatg                              36

<210> SEQ ID NO 39
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: PR-11138 (Hphsyn _fw)n = uracil

<400> SEQUENCE: 39
agcaatgggn aaaaagcctg aactcaccgc                                     30

<210> SEQ ID NO 40
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: PR-11139 (Hphsyn _rev)n = uracil

<400> SEQUENCE: 40
attacatgan tattcctttg ccctcggacg                                     30

<210> SEQ ID NO 41
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: PR-11694 (GPAT_up_USER _fw)n = uracil

<400> SEQUENCE: 41
cgtgcgangc atctaggagc tccattcagc                                     30

<210> SEQ ID NO 42
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: PR-11695 (GPAT_down _USER_rev)n = uracil

<400> SEQUENCE: 42
cacgcgangg acgagcagac cacg                                           24

<210> SEQ ID NO 43
<211> LENGTH: 25
<212> TYPE: DNA
<213> ORGANISM: Artificial sequence

```
<220> FEATURE:
<223> OTHER INFORMATION: Primer
<220> FEATURE:
<221> NAME/KEY: misc_feature
<222> LOCATION: (1)..(25)
<223> OTHER INFORMATION: PR-13494 (Nat-Tcyc-loxP_fw)n = uracil

<400> SEQUENCE: 43
agggtacnac tttggatgat actgc                                          25

<210> SEQ ID NO 44
<211> LENGTH: 54
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(54)
<223> OTHER INFORMATION: PR-13549 (loxP-PrTefIntron _fw)n= uracil

<400> SEQUENCE: 44
ataacttcgn ataatgtatg ctatacgaag ttatagagac cgggttggcg gcgc           54

<210> SEQ ID NO 45
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: PR-14269 (UraYL_fw)

<400> SEQUENCE: 45
atgccctcct acgaggcccg                                                20

<210> SEQ ID NO 46
<211> LENGTH: 22
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(22)
<223> OTHER INFORMATION: PR-14270 (UraYL_rev)

<400> SEQUENCE: 46
ctagcagttg atcttctggt ag                                             22

<210> SEQ ID NO 47
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: PR-15426 (?hfd1_up _fw)n = uracil

<400> SEQUENCE: 47
cgtgcganat aagaaaaaaa acag                                           24

<210> SEQ ID NO 48
<211> LENGTH: 26
<212> TYPE: DNA
```

-continued

```
<213> ORGANISM: Artificial sequence
<220> FEATURE:
<223> OTHER INFORMATION: Primer
<220> FEATURE:
<221> NAME/KEY: misc_feature
<222> LOCATION: (1)..(26)
<223> OTHER INFORMATION: PR-15427 (delta-hfd1_up _rev)?n = uracil

<400> SEQUENCE: 48
agctgttcna ctaaccctac ttcctc                                    26

<210> SEQ ID NO 49
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: PR-15428 (delta-hfd1_down _fw)n = uracil

<400> SEQUENCE: 49
agtggccntt ttattggtgg tgtg                                      24

<210> SEQ ID NO 50
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-15429 (delta-hfd1_down _rev)n = uracil

<400> SEQUENCE: 50
cacgcgangc atagtgcttt tcatattc                                  28

<210> SEQ ID NO 51
<211> LENGTH: 32
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(32)
<223> OTHER INFORMATION: PR-15438 (delta-hfd4_up _fw)n = uracil

<400> SEQUENCE: 51
cgtgcganag tatcgctact gtactaaaat tg                             32

<210> SEQ ID NO 52
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-15439 (delta-hfd4_up _rev)n = uracil

<400> SEQUENCE: 52
agctgttcna gcggacaagt gtcaatgtt                                 29

<210> SEQ ID NO 53
<211> LENGTH: 31
```

```
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: PR-15440 (delta-hfd4_down _fw)n = uracil

<400> SEQUENCE: 53
agtggccnat gtattttatc agtagtatct c                              31

<210> SEQ ID NO 54
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-15441 (delta-hfd4_down _rev)n = uracil

<400> SEQUENCE: 54
cacgcganat tggataatac atttccta                                  28

<210> SEQ ID NO 55
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-16463 (delta-fao1YL_up _fw)n = uracil

<400> SEQUENCE: 55
cgtgcgantg ggggaggatt gcgatggg                                  28

<210> SEQ ID NO 56
<211> LENGTH: 31
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: PR-16464 (delta-fao1YL_up _rev)n = uracil

<400> SEQUENCE: 56
agctgttcnt gtcaagtaat caagctaatg c                              31

<210> SEQ ID NO 57
<211> LENGTH: 31
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: PR-16465 (delta-fao1YL_down _fw)n = uracil

<400> SEQUENCE: 57
agtggccngc aagagacgag tttagaaata g                              31

<210> SEQ ID NO 58
```

<210> SEQ ID NO 58
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-16466 (delta-fao1YL_down _rev)n = uracil

<400> SEQUENCE: 58
cacgcgangt gttagttcct tgtagtgtg                              29

<210> SEQ ID NO 59
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-16696 (GPAT_up _rev)n = uracil

<400> SEQUENCE: 59
agctgttcnt accgcacttc cggaacatc                              29

<210> SEQ ID NO 60
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-16698 (GPAT_100bpPr_down _fw)n = uracil

<400> SEQUENCE: 60
agtggccncc gatacttgtt tgtgtgac                               28

<210> SEQ ID NO 61
<211> LENGTH: 1578
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1578)
<223> OTHER INFORMATION: Y.lipolytica codon-optimized nucleotide
      sequence of alcohol acetyltransferase from S. cerevisiae ATF1

<400> SEQUENCE: 61
atgaacgaga tcgacgagaa gaaccaggct cctgtgcagc aagagtgcct gaaggaaatg      60
atccagaacg acacgcccg acgaatgggc tctgtcgagg acctgtacgt ggccctgaac      120
cgacagaacc tgtaccgaaa cttctgcacc tacggcgagc tgtctgacta ctgcacccga     180
gatcagctga ccctggctct gcgagagatc tgcctgaaga accctactct gctgcatatc     240
gtgctgccca ctcgatggcc caaccacgag aactactacc gatcttctga gtactactct     300
cgaccccatc ctgtgcacga ctacatctcc gtgctgcaag ctgaagct gtctggcgtg       360 gtgctgaacg agcagcccga gtactctgcc gtgatgaagc agatcctgga agagttcaag     420
aactctaagg gctcttacac cgccaagatc ttcaagctga ctactaccct gaccattcct     480
tacttcggcc ccactggacc ctcttggcga ctgatctgtc tgcccgagga acacaccgag     540

-continued

```
aagtggaaga agttcatctt cgtttctaac cactgcatgt ctgacggacg atcctctatc      600
cacttctttc acgacctgcg agatgagctg aacaacatca agaccectcc aaagaagctg      660 gactacattt tcaagtacga agaggactac cagctgctgc gaaagctgcc cgagcctatc      720
gagaaggtga tcgacttccg acctccttac ctgttcatcc ccaagtctct gctgtctgga      780
ttcatctaca accacctccg attctcttcg aagggcgtgt gcatgcgaat ggacgacgtg      840
gaaaagaccg acgacgttgt gaccgagatc atcaacatct ctcccaccga gttccaggcc      900
atcaaggcca acattaagtc taacatccag ggcaagtgta ccatcactcc ctttctgcac      960
gtgtgctggt tcgtgtctct gcacaagtgg ggcaagttct taagcccct gaacttcgag      1020 tggctgaccg acatcttcat ccccgccgac tgccgatctc agctgcctga cgacgacgag      1080
atgcgacaga tgtaccgata cggcgccaac gtgggcttca tcgacttcac cccttggatc      1140
tctgagttcg acatgaacga caacaaggaa aacttctggc ccctgatcga gcactaccac      1200
gaggtgattt ctgaggccct gcgaaacaag aagcacctcc acggcctggg cttcaacatt      1260
cagggcttcg tccagaagta cgtcaacatt gacaaggtga tgtgcgaccg agccatcggc      1320
aagcgacgag gcggcaccct gctgtctaac gtgggcctgt caaccagct cgaggaaccc      1380 gacgccaagt actctatctg cgacctggcc ttcggccagt ccaaggctc ttggcaccag      1440 gctttctccc tgggcgtgtg ttctaccaac gtgaagggca tgaacatcgt ggtggcctct      1500
accaagaacg tggtgggctc tcaagagtct ctggaagaac tgtgctctat ctacaaggcc      1560
ctgctgctgg gcccctaa                                                   1578
```

<210> SEQ ID NO 62
<211> LENGTH: 525
<212> TYPE: PRT
<213> ORGANISM: Saccharomyces cerevisiae

<400> SEQUENCE: 62

```
Met Asn Glu Ile Asp Glu Lys Asn Gln Ala Pro Val Gln Gln Glu Cys
1               5                   10                  15

Leu Lys Glu Met Ile Gln Asn Gly His Ala Arg Arg Met Gly Ser Val
            20                  25                  30

Glu Asp Leu Tyr Val Ala Leu Asn Arg Gln Asn Leu Tyr Arg Asn Phe
        35                  40                  45

Cys Thr Tyr Gly Glu Leu Ser Asp Tyr Cys Thr Arg Asp Gln Leu Thr
    50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95

Glu Tyr Tyr Ser Arg Pro His Pro Val His Asp Tyr Ile Ser Val Leu
            100                 105                 110

Gln Glu Leu Lys Leu Ser Gly Val Val Leu Asn Glu Gln Pro Glu Tyr
        115                 120                 125

Ser Ala Val Met Lys Gln Ile Leu Glu Glu Phe Lys Asn Ser Lys Gly
    130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
            180                 185                 190
```

Met Ser Asp Gly Arg Ser Ser Ile His Phe Phe His Asp Leu Arg Asp
            195                 200                 205

Glu Leu Asn Asn Ile Lys Thr Pro Pro Lys Lys Leu Asp Tyr Ile Phe
        210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
            260                 265                 270

Val Cys Met Arg Met Asp Val Glu Lys Thr Asp Asp Val Val Thr
        275                 280                 285

Glu Ile Ile Asn Ile Ser Pro Thr Glu Phe Gln Ala Ile Lys Ala Asn
    290                 295                 300

Ile Lys Ser Asn Ile Gln Gly Lys Cys Thr Ile Thr Pro Phe Leu His
305                 310                 315                 320

Val Cys Trp Phe Val Ser Leu His Lys Trp Gly Lys Phe Lys Pro
                325                 330                 335

Leu Asn Phe Glu Trp Leu Thr Asp Ile Phe Ile Pro Ala Asp Cys Arg
            340                 345                 350

Ser Gln Leu Pro Asp Asp Asp Glu Met Arg Gln Met Tyr Arg Tyr Gly
        355                 360                 365

Ala Asn Val Gly Phe Ile Asp Phe Thr Pro Trp Ile Ser Glu Phe Asp
    370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys Lys His Leu His Gly Leu
                405                 410                 415

Gly Phe Asn Ile Gln Gly Phe Val Gln Lys Tyr Val Asn Ile Asp Lys
            420                 425                 430

Val Met Cys Asp Arg Ala Ile Gly Lys Arg Arg Gly Gly Thr Leu Leu
        435                 440                 445

Ser Asn Val Gly Leu Phe Asn Gln Leu Glu Glu Pro Asp Ala Lys Tyr
    450                 455                 460

Ser Ile Cys Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Val Ala Ser Thr Lys Asn Val Val Gly Ser Gln Glu Ser Leu Glu
            500                 505                 510

Glu Leu Cys Ser Ile Tyr Lys Ala Leu Leu Leu Gly Pro
        515                 520                 525

<210> SEQ ID NO 63
<211> LENGTH: 1086
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1086)
<223> OTHER INFORMATION: Y. lipolytica codon-optimized nucleotide
      sequence of delta9 desaturase from Drosophila melanogaster Dmd9

<400> SEQUENCE: 63

```
atggctccct actctcgaat ctaccaccag acaagtcgt cccgagagac tggcgtgctg      60
ttcgaggacg acgcccagac cgtggactct gacctgacca ccgaccgatt ccagctgaag     120
cgagccgaga agcgacgact gccctggtg tggcgaaaca tcatcctgtt cgccctggtg     180
cacctggccg ctctgtacgg cctgcactct atcttcaccc gagccaagct ggccaccact    240
ctgttcgctg ccggcctgta catcatcggc atgctgggcg tgaccgctgg cgcccaccga    300
ctgtgggctc accgaaccta caaggccaag tggccctgc gactgctgct ggtgatcttc     360
aacaccattg ccttccagga cgccgtgtac cactgggccc gagatcaccg agtgcaccac    420
aagtactctg agactgacgc tgaccctcac aacgctaccc gaggcttctt cttctctcac    480
gtcggctggc tgctgtgcaa gaagcacccc gacatcaagg aaaagggccg aggcctggac    540
ctgtctgacc tgcgagctga ccccatcctg atgttccagc gaaagcacta ctacattctg    600
atgcccctgg cctgcttcgt gctgccacc gtgattccca tggtgtactg gaacgagact     660
ctggcctctt cctggttcgt ggccaccatg ttccgatggt gcttccagct caacatgacc    720
tggctggtga actctgccgc tcacaagttc ggcaaccgac cttacgacaa gactatgaac    780
cccactcaga acgccttcgt gtctgccttc accttcggcg aaggctggca caactaccac    840
cacgcattcc cttgggacta caagaccgcc gagtggggct gctactctct gaacatcacc    900
accgccttca tcgacctgtt cgctaagatc ggctgggcct acgacctcaa gaccgtggct    960
cccgacgtga tccagcgacg agtgctgcga accggcgacg ctctcacga gctgtggggc    1020
tggggcgaca aggacctgac cgctgaggac gcccgaaacg tcctgctggt ggacaagtct   1080
cgataa                                                              1086
```

<210> SEQ ID NO 64
<211> LENGTH: 1368
<212> TYPE: DNA
<213> ORGANISM: Artificial sequence
<220> FEATURE:
<223> OTHER INFORMATION: codon-optimized nucleotide sequence
<220> FEATURE:
<221> NAME/KEY: misc_feature
<222> LOCATION: (1)..(1368)
<223> OTHER INFORMATION: Y.lipolytica codon-optimized nucleotide
       sequence of fatty acyl reductase from H. armigera Har_FAR

<400> SEQUENCE: 64

```
atggtggtcc tgacctctaa ggagactaag ccctccgtgg ccgagttcta cgctggcaag      60
tctgtcttca tcaccggcgg aaccggtttc ctgggcaagg tcttcattga agctgctg       120
tactcctgtc ccgacatcgg caacatctac atgctgatcc gagagaagaa gggactgtct    180
gtgtccgagc gaattaagca cttcctggac gacccctgt tcacccgact gaaggagaag     240
cgacccgccg acctggagaa gatcgtgctg attcccggag acatcaccgc tcccgacctg    300
ggtattacct ctgagaacga aagatgctg atcgagaagg tgtctgtcat cattcactcc     360
gccgctaccg tcaagttcaa cgagcccctg ccaccgcct ggaagatcaa cgtggaggga    420
acccgaatga tgctggctct gtctcgacga atgaagcgaa ttgaggtctt catccacatt    480
tccaccgcct acaccaacac caaccgagag gtggtggacg agatcctgta ccctgctcct    540
gctgacattg accaggtgca ccgatacgtc aaggacggta tctctgagga agagactgag    600
aagattctga acggccgacc caacaccctac accttccaca aggccctgac cgagcacctg    660
gtggctgaga accaggctta cgtgcccacc atcattgtcc gacctccgt ggtcgccgct    720
atcaaggacg agcccattaa gggatggctg gtaactggt acggagctac cggactgacc    780
```

```
gtgttcaccg ctaagggtct gaaccgagtc atctacggcc actcttccaa catcgtggac        840
ctgattcccg tggactacgt cgccaacctg gtcattgccg ctggcgctaa gtcttccaag        900
tccaccgagc tgaaggtgta caactgttgc tcttccgcct gcaaccccat caccattgga        960
aagctgatgt ctatgttcgc cgaggacgct atcaagcaga agtcctacgc tatgcccctg       1020
cccggttggt acatcttcac caagtacaag tggctggtcc tgctgctgac cattctgttc       1080
caggtcatcc ccgcctacat taccgacctg taccgacacc tgatcggcaa gaaccccga       1140 tacattaagc tgcagtctct ggtcaaccag acccgatctt ccattgactt cttcacctct       1200
cactcctggg tcatgaaggc tgaccgagtc cgagagctgt tcgcctctct gtcccccgct       1260
gacaagtacc tgttcccctg tgaccccacc gacatcaact ggaccacta cattcaggac       1320 tactgctggg gagtgcgaca cttcctggag aagaagtcct acgagtag                    1368
```

<210> SEQ ID NO 65
<211> LENGTH: 1062
<212> TYPE: DNA
<213> ORGANISM: Spodoptera litura

<400> SEQUENCE: 65

```
atggctccca acatctctga ggacgtgaac ggcgtgctgt tcgagtctga cgccgctact         60
cccgacctgg ctctggcccg acctcctgtg cagaaggccg acaacaagcc caagcagctg        120
gtgtggcgaa acatcatcct gttcgcctac ctgcacctgg ccgctctgta cggcggctac        180
ctgttcctgt ctctgccaa gtggcagacc gacatcttcg cctacatcct gtacgtgatc         240
tctggcctgg gcatcaccgc tggcgcccac cgactgtggg ctcacaagtc ttacaaggct        300
aagtggcccc tgaaggtgat cctgatcatc ttcaacaccg tggccttcca ggacgccgcc        360
atggactggg cccgagatca ccgaatgcac cacaagtact ctgagactga cgctgaccct        420
cacaacgcta cccgaggctt cttcttctct cacatcggct ggctgctggt gcgaaagcac        480
cccgacctga aggaaaaggg caagggcctc gacatgtctg acctgctggc tgaccccgtg        540
ctgcgattcc agaagaagta ctacctgctg ctgatgcccc tggcctgctt cgtcatgccc        600
accgtgattc ccgtgtacct gtggggcgag acttggacca acgccttctt cgtggccgcc        660
atgttccgat acgccttcat tctgaacgtg acctggctgg tgaactctgc tgcccacaag        720
tggggcgaca gccctacga caagtctatc aagccctctg agaacatgtc tgtggccatg        780
ttcgccctcg gcgagggatt ccacaactac caccacacat tcccttggga ctacaagacc        840
gccgagttcg gcaacaacaa gctgaacttc actaccgcct tcatcaactt tttcgccaag        900
atcggctggg cttacgacat gaagaccgtg tctgaggaca tcgtgaagaa ccgagtgaag        960
cgaaccggcg acggctctca ccacctctgg ggctggggcg acgagaacca gcctaaggaa       1020
gagatcgagg ccgccatccg aatcaacccc aaggacgact aa                          1062
```

<210> SEQ ID NO 66
<211> LENGTH: 353
<212> TYPE: PRT
<213> ORGANISM: Spodoptera litura

<400> SEQUENCE: 66

Met Ala Pro Asn Ile Ser Glu Asp Val Asn Gly Val Leu Phe Glu Ser
1               5                   10                  15

Asp Ala Ala Thr Pro Asp Leu Ala Leu Ala Arg Pro Pro Val Gln Lys
            20                  25                  30

Ala Asp Asn Lys Pro Lys Gln Leu Val Trp Arg Asn Ile Ile Leu Phe

```
              35                  40                  45
Ala Tyr Leu His Leu Ala Ala Leu Tyr Gly Gly Tyr Leu Phe Leu Phe
 50                  55                  60

Ser Ala Lys Trp Gln Thr Asp Ile Phe Ala Tyr Ile Leu Tyr Val Ile
 65                  70                  75                  80

Ser Gly Leu Gly Ile Thr Ala Gly Ala His Arg Leu Trp Ala His Lys
                 85                  90                  95

Ser Tyr Lys Ala Lys Trp Pro Leu Lys Val Ile Leu Ile Ile Phe Asn
            100                 105                 110

Thr Val Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175

Ala Asp Pro Val Leu Arg Phe Gln Lys Lys Tyr Tyr Leu Leu Leu Met
            180                 185                 190

Pro Leu Ala Cys Phe Val Met Pro Thr Val Ile Pro Val Tyr Leu Trp
        195                 200                 205

Gly Glu Thr Trp Thr Asn Ala Phe Phe Val Ala Ala Met Phe Arg Tyr
    210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Met
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Phe Gly Asn Asn Lys Leu
        275                 280                 285

Asn Phe Thr Thr Ala Phe Ile Asn Phe Phe Ala Lys Ile Gly Trp Ala
    290                 295                 300

Tyr Asp Met Lys Thr Val Ser Glu Asp Ile Val Lys Asn Arg Val Lys
305                 310                 315                 320

Arg Thr Gly Asp Gly Ser His His Leu Trp Gly Trp Gly Asp Glu Asn
                325                 330                 335

Gln Pro Lys Glu Glu Ile Glu Ala Ala Ile Arg Ile Asn Pro Lys Asp
            340                 345                 350

Asp

<210> SEQ ID NO 67
<211> LENGTH: 981
<212> TYPE: DNA
<213> ORGANISM: Artificial sequence
<220> FEATURE:
<223> OTHER INFORMATION: Codon-optimised sequence
<220> FEATURE:
<221> NAME/KEY: CDS
<222> LOCATION: (1)..(981)
<223> OTHER INFORMATION: Y. lipolytica codon-optimized nucleotide
      sequence of ?11 desaturase from Amyelois transitella

<400> SEQUENCE: 67 atg gtg ccc aac aag ggt tct tcc gac gtc ctg tct gag cac tcc gag    48
Met Val Pro Asn Lys Gly Ser Ser Asp Val Leu Ser Glu His Ser Glu
 1               5                  10                  15
```

```
ccc cag ttc acc aag ctg att gct ccc cag gct ggc ccc cga aag tac    96
Pro Gln Phe Thr Lys Leu Ile Ala Pro Gln Ala Gly Pro Arg Lys Tyr
         20                  25                  30 aag atc gtg tac cga aac ctg ctg acc ttc gga tac tgg cac ctg tct   144
Lys Ile Val Tyr Arg Asn Leu Leu Thr Phe Gly Tyr Trp His Leu Ser
             35                  40                  45 gcc gtc tac ggt ctg tac ctg tgt ttc acc tgc gcc aag tgg gct acc   192
Ala Val Tyr Gly Leu Tyr Leu Cys Phe Thr Cys Ala Lys Trp Ala Thr
 50                  55                  60 att ctg ttc gcc ttc ttc ctg tac gtg atc gct gag atc ggc att acc   240
Ile Leu Phe Ala Phe Phe Leu Tyr Val Ile Ala Glu Ile Gly Ile Thr
 65                  70                  75                  80 ggc gga gcc cac cga ctg tgg gct cac cga acc tac aag gcc aag ctg   288
Gly Gly Ala His Arg Leu Trp Ala His Arg Thr Tyr Lys Ala Lys Leu
                 85                  90                  95 ccc ctg gag atc ctg ctg ctg att atg aac tct atc gct ttc cag gac   336
Pro Leu Glu Ile Leu Leu Leu Ile Met Asn Ser Ile Ala Phe Gln Asp
             100                 105                 110 acc gcc ttc acc tgg gct cga gat cac cga ctg cac cac aag tac tct   384
Thr Ala Phe Thr Trp Ala Arg Asp His Arg Leu His His Lys Tyr Ser
         115                 120                 125 gac acc gac gct gac cct cac aac gct acc cga ggt ttc ttc tac tcc   432
Asp Thr Asp Ala Asp Pro His Asn Ala Thr Arg Gly Phe Phe Tyr Ser
 130                 135                 140 cac gtg ggc tgg ctg ctg gtc aag aag cac ccc gag gtg aag gcc cgg   480
His Val Gly Trp Leu Leu Val Lys Lys His Pro Glu Val Lys Ala Arg
145                 150                 155                 160 gga aag tac ctg tcc ctg gac gac ctg aag aac aac ccc ctg ctg aag   528
Gly Lys Tyr Leu Ser Leu Asp Asp Leu Lys Asn Asn Pro Leu Leu Lys
                 165                 170                 175 ttc cag aag aag tac gct atc ctg gtc att ggc acc ctg tgt ttc ctg   576
Phe Gln Lys Lys Tyr Ala Ile Leu Val Ile Gly Thr Leu Cys Phe Leu
             180                 185                 190 atg ccc acc ttc gtg ccc gtc tac ttc tgg ggt gag ggc att tct acc   624
Met Pro Thr Phe Val Pro Val Tyr Phe Trp Gly Glu Gly Ile Ser Thr
         195                 200                 205 gcc tgg aac atc aac ctg ctg cga tac gtg atg aac ctg aac atg acc   672
Ala Trp Asn Ile Asn Leu Leu Arg Tyr Val Met Asn Leu Asn Met Thr
 210                 215                 220 ttc ctg gtc aac tcc gcc gct cac att ttc ggc aac aag ccc tac gac   720
Phe Leu Val Asn Ser Ala Ala His Ile Phe Gly Asn Lys Pro Tyr Asp
225                 230                 235                 240 aag tct att gcc tcc gtg cag aac atc tct gtc tcc ctg gct acc ttc   768
Lys Ser Ile Ala Ser Val Gln Asn Ile Ser Val Ser Leu Ala Thr Phe
                 245                 250                 255 gga gag ggt ttc cac aac tac cac cac acc tac cct tgg gac tac cga   816
Gly Glu Gly Phe His Asn Tyr His His Thr Tyr Pro Trp Asp Tyr Arg
             260                 265                 270 gct gct gag ctg ggc aac aac cga ctg aac atg acc acc gcc ttc att   864
Ala Ala Glu Leu Gly Asn Asn Arg Leu Asn Met Thr Thr Ala Phe Ile
         275                 280                 285 gac ttc ttc gcc tgg atc gga tgg gct tac gac ctg aag tcc gtc ccc   912
Asp Phe Phe Ala Trp Ile Gly Trp Ala Tyr Asp Leu Lys Ser Val Pro
 290                 295                 300 cag gaa gcc atc gct aag cga tgc gct aag acc ggc gac gga acc gac   960
Gln Glu Ala Ile Ala Lys Arg Cys Ala Lys Thr Gly Asp Gly Thr Asp
305                 310                 315                 320 atg tgg gga cga aag cga tag                                       981
Met Trp Gly Arg Lys Arg
```

<210> SEQ ID NO 68
<211> LENGTH: 326
<212> TYPE: PRT
<213> ORGANISM: Artificial sequence
<220> FEATURE:
<223> OTHER INFORMATION: Synthetic Construct

<400> SEQUENCE: 68

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Ile Met Asn Ser Ile Ala Phe Gln Asp
            100                 105                 110

Thr Ala Phe Thr Trp Ala Arg Asp His Arg Leu His His Lys Tyr Ser
            115                 120                 125

Asp Thr Asp Ala Asp Pro His Asn Ala Thr Arg Gly Phe Phe Tyr Ser
130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
        195                 200                 205

Ala Trp Asn Ile Asn Leu Leu Arg Tyr Val Met Asn Leu Asn Met Thr
    210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
        275                 280                 285

Asp Phe Phe Ala Trp Ile Gly Trp Ala Tyr Asp Leu Lys Ser Val Pro
    290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 69
<211> LENGTH: 1368
<212> TYPE: DNA

```
<213> ORGANISM: Artificial sequence
<220> FEATURE:
<223> OTHER INFORMATION: Codon-optimised sequence
<220> FEATURE:
<221> NAME/KEY: CDS
<222> LOCATION: (1)..(1368)
<223> OTHER INFORMATION: Y. lipolytica codon-optimized nucleotide
      sequence of fatty acyl reductase from Helicoverpa armigera

<400> SEQUENCE: 69 atg gtg gtc ctg acc tct aag gag act aag ccc tcc gtg gcc gag ttc      48
Met Val Val Leu Thr Ser Lys Glu Thr Lys Pro Ser Val Ala Glu Phe
1               5                   10                  15 tac gct ggc aag tct gtc ttc atc acc ggc gga acc ggt ttc ctg ggc      96
Tyr Ala Gly Lys Ser Val Phe Ile Thr Gly Gly Thr Gly Phe Leu Gly
                20                  25                  30 aag gtc ttc att gag aag ctg ctg tac tcc tgt ccc gac atc ggc aac     144
Lys Val Phe Ile Glu Lys Leu Leu Tyr Ser Cys Pro Asp Ile Gly Asn
            35                  40                  45 atc tac atg ctg atc cga gag aag aag gga ctg tct gtg tcc gag cga     192
Ile Tyr Met Leu Ile Arg Glu Lys Lys Gly Leu Ser Val Ser Glu Arg
 50                  55                  60 att aag cac ttc ctg gac gac ccc ctg ttc acc cga ctg aag gag aag     240
Ile Lys His Phe Leu Asp Asp Pro Leu Phe Thr Arg Leu Lys Glu Lys
65                  70                  75                  80 cga ccc gcc gac ctg gag aag atc gtg ctg att ccc gga gac atc acc     288
Arg Pro Ala Asp Leu Glu Lys Ile Val Leu Ile Pro Gly Asp Ile Thr
                85                  90                  95 gct ccc gac ctg ggt att acc tct gag aac gag aag atg ctg atc gag     336
Ala Pro Asp Leu Gly Ile Thr Ser Glu Asn Glu Lys Met Leu Ile Glu
                100                 105                 110 aag gtg tct gtc atc att cac tcc gcc gct acc gtc aag ttc aac gag     384
Lys Val Ser Val Ile Ile His Ser Ala Ala Thr Val Lys Phe Asn Glu
            115                 120                 125 ccc ctg ccc acc gcc tgg aag atc aac gtg gag gga acc cga atg atg     432
Pro Leu Pro Thr Ala Trp Lys Ile Asn Val Glu Gly Thr Arg Met Met
130                 135                 140 ctg gct ctg tct cga cga atg aag cga att gag gtc ttc atc cac att     480
Leu Ala Leu Ser Arg Arg Met Lys Arg Ile Glu Val Phe Ile His Ile
145                 150                 155                 160 tcc acc gcc tac acc aac acc aac cga gag gtg gtg gac gag atc ctg     528
Ser Thr Ala Tyr Thr Asn Thr Asn Arg Glu Val Val Asp Glu Ile Leu
                165                 170                 175 tac cct gct cct gct gac att gac cag gtg cac cga tac gtc aag gac     576
Tyr Pro Ala Pro Ala Asp Ile Asp Gln Val His Arg Tyr Val Lys Asp
                180                 185                 190 ggt atc tct gag gaa gag act gag aag att ctg aac ggc cga ccc aac     624
Gly Ile Ser Glu Glu Glu Thr Glu Lys Ile Leu Asn Gly Arg Pro Asn
            195                 200                 205 acc tac acc ttc acc aag gcc ctg acc gag cac ctg gtg gct gag aac     672
Thr Tyr Thr Phe Thr Lys Ala Leu Thr Glu His Leu Val Ala Glu Asn
210                 215                 220 cag gct tac gtg ccc acc atc att gtc cga ccc tcc gtg gtc gcc gct     720
Gln Ala Tyr Val Pro Thr Ile Ile Val Arg Pro Ser Val Val Ala Ala
225                 230                 235                 240 atc aag gac gag ccc att aag gga tgg ctg ggt aac tgg tac gga gct     768
Ile Lys Asp Glu Pro Ile Lys Gly Trp Leu Gly Asn Trp Tyr Gly Ala
                245                 250                 255 acc gga ctg acc gtg ttc acc gct aag ggt ctg aac cga gtc atc tac     816
Thr Gly Leu Thr Val Phe Thr Ala Lys Gly Leu Asn Arg Val Ile Tyr
                260                 265                 270
```

```
ggc cac tct tcc aac atc gtg gac ctg att ccc gtg gac tac gtc gcc    864
Gly His Ser Ser Asn Ile Val Asp Leu Ile Pro Val Asp Tyr Val Ala
        275                 280                 285 aac ctg gtc att gcc gct ggc gct aag tct tcc aag tcc acc gag ctg    912
Asn Leu Val Ile Ala Ala Gly Ala Lys Ser Ser Lys Ser Thr Glu Leu
        290                 295                 300 aag gtg tac aac tgt tgc tct tcc gcc tgc aac ccc atc acc att gga    960
Lys Val Tyr Asn Cys Cys Ser Ser Ala Cys Asn Pro Ile Thr Ile Gly
305                 310                 315                 320 aag ctg atg tct atg ttc gcc gag gac gct atc aag cag aag tcc tac   1008
Lys Leu Met Ser Met Phe Ala Glu Asp Ala Ile Lys Gln Lys Ser Tyr
            325                 330                 335 gct atg ccc ctg ccc ggt tgg tac atc ttc acc aag tac aag tgg ctg   1056
Ala Met Pro Leu Pro Gly Trp Tyr Ile Phe Thr Lys Tyr Lys Trp Leu
        340                 345                 350 gtc ctg ctg ctg acc att ctg ttc cag gtc atc ccc gcc tac att acc   1104
Val Leu Leu Leu Thr Ile Leu Phe Gln Val Ile Pro Ala Tyr Ile Thr
        355                 360                 365 gac ctg tac cga cac ctg atc ggc aag aac ccc cga tac att aag ctg   1152
Asp Leu Tyr Arg His Leu Ile Gly Lys Asn Pro Arg Tyr Ile Lys Leu
370                 375                 380 cag tct ctg gtc aac cag acc cga tct tcc att gac ttc ttc acc tct   1200
Gln Ser Leu Val Asn Gln Thr Arg Ser Ser Ile Asp Phe Phe Thr Ser
385                 390                 395                 400 cac tcc tgg gtc atg aag gct gac cga gtc cga gag ctg ttc gcc tct   1248
His Ser Trp Val Met Lys Ala Asp Arg Val Arg Glu Leu Phe Ala Ser
            405                 410                 415 ctg tcc ccc gct gac aag tac ctg ttc ccc tgt gac ccc acc gac atc   1296
Leu Ser Pro Ala Asp Lys Tyr Leu Phe Pro Cys Asp Pro Thr Asp Ile
        420                 425                 430 aac tgg acc cac tac att cag gac tac tgc tgg gga gtg cga cac ttc   1344
Asn Trp Thr His Tyr Ile Gln Asp Tyr Cys Trp Gly Val Arg His Phe
        435                 440                 445 ctg gag aag aag tcc tac gag tag                                    1368
Leu Glu Lys Lys Ser Tyr Glu
    450                 455

<210> SEQ ID NO 70
<211> LENGTH: 455
<212> TYPE: PRT
<213> ORGANISM: Artificial sequence
<220> FEATURE:
<223> OTHER INFORMATION: Synthetic Construct

<400> SEQUENCE: 70

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110
```

Lys Val Ser Val Ile Ile His Ser Ala Ala Thr Val Lys Phe Asn Glu
115                 120                 125

Pro Leu Pro Thr Ala Trp Lys Ile Asn Val Glu Gly Thr Arg Met Met
130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
                180                 185                 190

Gly Ile Ser Glu Glu Thr Glu Lys Ile Leu Asn Gly Arg Pro Asn
                195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
                260                 265                 270

Gly His Ser Ser Asn Ile Val Asp Leu Ile Pro Val Asp Tyr Val Ala
                275                 280                 285

Asn Leu Val Ile Ala Ala Gly Ala Lys Ser Ser Lys Ser Thr Glu Leu
                290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
                340                 345                 350

Val Leu Leu Leu Thr Ile Leu Phe Gln Val Ile Pro Ala Tyr Ile Thr
                355                 360                 365

Asp Leu Tyr Arg His Leu Ile Gly Lys Asn Pro Arg Tyr Ile Lys Leu
370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
                420                 425                 430

Asn Trp Thr His Tyr Ile Gln Asp Tyr Cys Trp Gly Val Arg His Phe
                435                 440                 445

Leu Glu Lys Lys Ser Tyr Glu
450                 455

<210> SEQ ID NO 71
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: PR-10714

<400> SEQUENCE: 71
ttgcttgcga acctaattcc                                                20

<210> SEQ ID NO 72
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: PR-10766

<400> SEQUENCE: 72
ataacttcgu ataatgtatg ctatacgaag ttataaggag tttggcgccc g              51

<210> SEQ ID NO 73
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(19)
<223> OTHER INFORMATION: PR-10767

<400> SEQUENCE: 73
tcatggacat ggcatagac                                                 19

<210> SEQ ID NO 74
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: PR-11047

<400> SEQUENCE: 74
aataacttcg uatagcatac attatacgaa gttatcgagc gtcccaaaac c              51

<210> SEQ ID NO 75
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-13338

<400> SEQUENCE: 75
acctgcacug ttgatgtgtg tttaattc                                       28

<210> SEQ ID NO 76
<211> LENGTH: 22
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(22)
<223> OTHER INFORMATION: PR-141

```
<400> SEQUENCE: 76
agaacagcug aagcuucgua cg                                          22

<210> SEQ ID NO 77
<211> LENGTH: 31
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(31)
<223> OTHER INFORMATION: PR-14148

<400> SEQUENCE: 77
acgtgcaacg cuacgcaac taacatgaat g                                 31

<210> SEQ ID NO 78
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: PR-14149

<400> SEQUENCE: 78
tgacttcaac attatatcgc tctga                                       25

<210> SEQ ID NO 79
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: PR-142

<400> SEQUENCE: 79
aggccacuag tggatctgat atcac                                       25

<210> SEQ ID NO 80
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-14565

<400> SEQUENCE: 80
agtggccugg ggctggcgtg tgaaggag                                    28

<210> SEQ ID NO 81
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: PR-14566
```

<400> SEQUENCE: 81
acgcgaucag acctctcaca cggcatc                                                27

<210> SEQ ID NO 82
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: PR-14567

<400> SEQUENCE: 82
taatacgact cactataggg c                                                      21

<210> SEQ ID NO 83
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-14568

<400> SEQUENCE: 83
cacgcgaucc ttgagacgtt accagagc                                               28

<210> SEQ ID NO 84
<211> LENGTH: 37
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(37)
<223> OTHER INFORMATION: PR-14589

<400> SEQUENCE: 84
cgtgcgaugc ggaggagcaa tagacatacg atttgac                                     37

<210> SEQ ID NO 85
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: PR-14590

<400> SEQUENCE: 85
aagcgttgca cgutcccctc cccacggtg                                              29

<210> SEQ ID NO 86
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-14591

<400> SEQUENCE: 86
agtggccuca ccgagggata gggaacac                                              28

<210> SEQ ID NO 87
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: PR-14592

<400> SEQUENCE: 87
acgcgautta acactggacc gtactgc                                               27

<210> SEQ ID NO 88
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: PR-15430

<400> SEQUENCE: 88
cgtgcgaugg ttctatacga tgg                                                   23

<210> SEQ ID NO 89
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-15431

<400> SEQUENCE: 89
agctgttcut atgatatttt tactaacc                                              28

<210> SEQ ID NO 90
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-15432

<400> SEQUENCE: 90
agtggccuga ttggcgttgt gttcaaatg                                             29

<210> SEQ ID NO 91
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)

<223> OTHER INFORMATION: PR-15433

<400> SEQUENCE: 91
cacgcgautt gctcattcac cagaaaag                28

<210> SEQ ID NO 92
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-15434

<400> SEQUENCE: 92
cgtgcgauat gtacaagtat ttctattg                28

<210> SEQ ID NO 93
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-15435

<400> SEQUENCE: 93
agctgttcug aatgataaag agataacag               29

<210> SEQ ID NO 94
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-15436

<400> SEQUENCE: 94
agtggccutg tggcggaagt tgtacacc                28

<210> SEQ ID NO 95
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: PR-15437

<400> SEQUENCE: 95
acctgcggtu agtactgcaa aaagtgctgg              30

<210> SEQ ID NO 96
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature

```
<222> LOCATION: (1)..(30)
<223> OTHER INFORMATION: PR-15930

<400> SEQUENCE: 96
acctgcggtu agtactgcaa aaagtgctgg                                    30

<210> SEQ ID NO 97
<211> LENGTH: 35
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(35)
<223> OTHER INFORMATION: PR-16592

<400> SEQUENCE: 97
agtgcaggug ccacaatggt gcccaacaag ggttc                              35

<210> SEQ ID NO 98
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: PR-16593

<400> SEQUENCE: 98
cgtgcgauct atcgctttcg tccccac                                       27

<210> SEQ ID NO 99
<211> LENGTH: 26
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(26)
<223> OTHER INFORMATION: PR-16594

<400> SEQUENCE: 99
aaccgcaggu ggtcctgacc tctaag                                        26

<210> SEQ ID NO 100
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-16595

<400> SEQUENCE: 100
cacgcgauct actcgtagga cttcttctc                                     29

<210> SEQ ID NO 101
<211> LENGTH: 20
<212> TYPE: DNA
<213> ORGANISM: Artificial sequence
<220> FEATURE:
<223> OTHER INFORMATION: Primer
<220> FEATURE:
```

```
<221> NAME/KEY: misc_feature
<222> LOCATION: (1)..(20)
<223> OTHER INFORMATION: PR-14279

<400> SEQUENCE: 101
cgtgcgauag agaccgggtt                                              20

<210> SEQ ID NO 102
<211> LENGTH: 30
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: PR-16618

<400> SEQUENCE: 102
agcctgcggu tagtactgca aaaagtgctg                                   30

<210> SEQ ID NO 103
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: PR-14395

<400> SEQUENCE: 103
cgtgcgautt gatatggtgt aacaatg                                      27

<210> SEQ ID NO 104
<211> LENGTH: 33
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(33)
<223> OTHER INFORMATION: PR-14396

<400> SEQUENCE: 104
aagcgttgca cguaagcact atcctctgct gcg                               33

<210> SEQ ID NO 105
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-14397

<400> SEQUENCE: 105
agtggccucc gagcgtcgac aagcatac                                     28

<210> SEQ ID NO 106
<211> LENGTH: 28
<212> TYPE: DNA
<213> ORGANISM: Artificial sequence
<220> FEATURE:
<223> OTHER INFORMATION: Primer
```

<220> FEATURE:
<221> NAME/KEY: misc_feature
<222> LOCATION: (1)..(28)
<223> OTHER INFORMATION: PR-14398

<400> SEQUENCE: 106
cacgcgaugt tagaagcaat tggagaag                                    28

<210> SEQ ID NO 107
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: PR-15521

<400> SEQUENCE: 107
cgtgcgauaa ggagtttggc gcccgtt                                     27

<210> SEQ ID NO 108
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: PR-15522

<400> SEQUENCE: 108
atgacagaut gctgtagata tgtcttgt                                    28

<210> SEQ ID NO 109
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: PR-18486

<400> SEQUENCE: 109
agtgcaggug ccacaatgaa cgagatc                                     27

<210> SEQ ID NO 110
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: PR-18487

<400> SEQUENCE: 110
cgtgcgautt aggggcccag                                             20

<210> SEQ ID NO 111
<211> LENGTH: 23
<212> TYPE: DNA
<213> ORGANISM: Artificial sequence
<220> FEATURE:

```
<223> OTHER INFORMATION: Primer
<220> FEATURE:
<221> NAME/KEY: misc_feature
<222> LOCATION: (1)..(23)
<223> OTHER INFORMATION: PR-18490

<400> SEQUENCE: 111
accgcaggcu ccctactctc gaa                                          23

<210> SEQ ID NO 112
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: PR-18489

<400> SEQUENCE: 112
cacgcgautt atcgagactt gtcc                                         24

<210> SEQ ID NO 113
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: PR-18499

<400> SEQUENCE: 113
atctgtcaug ccacaatggc tccca                                        25

<210> SEQ ID NO 114
<211> LENGTH: 24
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: PR-18500

<400> SEQUENCE: 114
cacgcgautt agtcgtcctt gggg                                         24
```

METHODS FOR PRODUCING FATTY ALCOHOLS AND DERIVATIVES THEREOF IN YEAST

TECHNICAL FIELD

The present invention relates to oleaginous yeast cells for the production of fatty alcohols and derivatives thereof, in particular desaturated fatty alcohols, desaturated fatty acyl acetates and desaturated fatty aldehydes. Also provided are methods for obtaining such compounds, which are useful in pheromone compositions.

BACKGROUND

Fatty alcohols are a group of chemicals with broad applications. Fatty alcohols are usually straight primary alcohols that vary in chain length ($C_6$-$C_{26}$) and can bear saturated or unsaturated carbon bonds. Depending on the above mentioned characteristics, fatty alcohols can be used as fuel, detergents and surfactants, cosmetics, insect pest management and many more.

Since the advent of DDT more than 50 years ago, broad-spectrum neurotoxic insecticides have provided the principal means for the control of economically important insects in agriculture and public health programs. Whereas the use of synthetic insecticides initially resulted in spectacular increases in crop yields and the suppression of some important human and animal disease vectors, the development of insecticide resistance in insect pest populations and the environmental damage caused by insecticides have become widely recognised as serious drawbacks to their use. Among the most significant environmental problems associated with the manufacture and use of insecticides are 1) their direct toxicity to non-target organisms (including humans); 2) their persistence in the biosphere where they can accumulate and cause untoward developmental and reproductive effects in higher organisms; 3) significant point-source pollution associated with their manufacture and distribution; 4) their worldwide dispersal.

Pheromones can be used as pest control instead of pesticides. (Z)19-14:OAc for example has been found to disrupt mating efficiency of fall armyworm with 86% efficiency when applied alone, i.e. without other pheromone components. The commercial use of pheromones to control insect pests by mating disruption has several advantages over conventional insecticides. Pheromones are: 1) non-toxic and environmentally benign; 2) specific to one target species and do not adversely affect non-target beneficial insects, making them extremely well suited for use in integrated pest management programs; and 3) much less likely (and have never been shown) to produce resistance in the target insect. In contrast to pheromone syntheses in nature, current approaches for the commercial production of pheromones employ traditional synthetic chemical routes. Because pheromones require very high purity to elicit an insect's response, these syntheses are expensive and difficult, and generate large amounts of organic wastes that require treatment.

Thus the major hurdle standing in the way of using sex pheromones remains the production cost. As a result, a very small part of global agricultural land employs pheromones (estimated to less than 0.05%). Pheromone production from a cell factory is expected to significantly lower the production costs of pheromones.

Fatty alcohols are usually produced chemically based on petrochemical or natural feedstocks. Some approaches have been made to produce fatty alcohols in microorganisms such as *Escherichia coli* and yeast using renewable feedstock such as e.g. glucose. Preferable hosts for microbial oleochemical production are oleaginous yeast, which are specialised in accumulating and consuming lipid-derived compounds. Among the oleaginous yeast most advanced research has been conducted on the yeast *Yarrowia lipolytica*.

Methods and host strains are needed to improve the production of fatty alcohols and derivatives thereof.

SUMMARY OF INVENTION

The invention is as defined in the claims.

Fatty alcohols can be produced in microorganisms by the heterologous expression of the enzyme fatty acyl reductase which reduces the natively produced fatty acyl-CoA esters to fatty alcohols. In microorganisms fatty acyl-CoA esters are used for membrane lipid production or stored in lipid bodies. Some microorganisms are able to degrade fatty alcohols. *Y. lipolytica* degrades fatty acid derived chemicals via beta-oxidation, which takes place in the peroxisomes, or via omega-oxidation pathway, occurring at the endoplasmic reticulum.

The present disclosure provides methods and host strains which increase fatty alcohol production by decreasing the activity of competing lipid biosynthesis pathway and by decreasing fatty alcohol degradation. These methods and host strains are particularly suitable for production of desaturated fatty alcohols and their derivatives (e.g., fatty acyl acetates), such as *Lepidoptera* pheromones.

Fatty acyl-CoA esters with different carbon chain length are synthesised by the fatty acyl-CoA synthetase complex (FAS1 and 2) from acetyl-CoA and malonyl-CoA and serve as substrates for storage and membrane lipids. The initial reaction towards lipids is the transfer of fatty acyl-CoAs to glycerol-3-phosphate, catalyzed by glycerol-3-phosphate 1-O-acyltransferase (GPAT) and resulting in formation of lysophosphatidic acid. The overexpression of GPAT in *Y. lipolytica* has been shown to increase lipid accumulation.

The oleaginous yeast *Y. lipolytica* is known to be able to utilize hydrophobic compounds as fatty alcohols as sole energy and carbon source. Fatty alcohols are thought to be oxidised into fatty aldehydes by fatty alcohol dehydrogenases present in both ER and peroxisomes and fatty alcohol oxidases (FAO) present in peroxisomes.

The fatty aldehydes are further oxidised to fatty acids by fatty aldehyde dehydrogenases (HFD). *Y. lipolytica*'s Adh1p, Adh3p and Fao1p have been suggested to play a role in degradation of exogenous fatty alcohols, while fatty alcohols resulting from alkane degradation have been suggested to be oxidised by Adh1p-Adh7p, Fadhp and Fao1p (Iwama, 2015). *Y. lipolytica* encodes four fatty aldehyde dehydrogenases, Hfd1p to Hfd4p, which have been shown to be essential for growth on n-alkanes (Iwama, 2014). The PEX10 gene encodes peroxisome biogenesis factor Peroxin 10. Deletion of PEX10 in *Y. lipolytica* results in the absence of peroxisomes and in defect in n-decane assimilation (Sumita et al, 2002).

The present invention describes the downregulation of GPAT, Hfd1, Hfd4, Fao1 and/or Pex10 expression as a strategy to redirect the flux of fatty acyl-CoA ester precursors from storage and membrane lipid synthesis to fatty alcohol production. In combination with the introduction of heterologous desaturases and fatty acyl-CoA reductases, this allows production of fatty alcohols and derivatives thereof with high titres, in particular such fatty alcohols and derivatives which are comprised in *Lepidoptera* pheromones, in an oleaginous yeast cell such as a *Yarrowia lipolytica* cell.

Herein is provided an oleaginous yeast cell capable of producing a desaturated fatty alcohol, said cell:
i) expressing at least one heterologous desaturase capable of introducing at least one double bond in a fatty acyl-CoA; and
ii) expressing at least one heterologous fatty acyl-CoA reductase, capable of converting at least part of said desaturated fatty acyl-CoA to a desaturated fatty alcohol; and
iii) having reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or having reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

Also provided is a method of producing a fatty alcohol in an oleaginous yeast cell, said method comprising the steps of providing a yeast cell and incubating said yeast cell in a medium, wherein the yeast cell:
i) expresses at least one heterologous desaturase capable of introducing at least one double bond in a fatty acyl-CoA, thereby converting at least part of said fatty acyl-CoA to a desaturated fatty acyl-CoA; and
ii) expresses at least one heterologous fatty acyl-CoA reductase, capable of converting at least part of said desaturated fatty acyl-CoA to a desaturated fatty alcohol, thereby producing said desaturated fatty alcohol; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

Also provided is a nucleic acid construct for modifying a yeast cell, said construct comprising:
i) a first polynucleotide encoding at least one heterologous desaturase capable of introducing at least one double bond in a fatty acyl-CoA; and
ii) a second polynucleotide encoding at least one heterologous fatty acyl-CoA reductase (FAR), capable of converting at least part of said desaturated fatty acyl-CoA to a desaturated fatty alcohol; and
iii) optionally, additional polynucleotides for reducing activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10),
wherein optionally the first polynucleotide and/or the second polynucleotide and/or the additional polynucleotides are under the control of a promoter.

Also provided is a kit of parts comprising:
a) the yeast cell as defined herein and instructions for use; and/or
b) a nucleic acid construct as defined herein, wherein said construct is for modifying a yeast cell, and
c) optionally the yeast cell to be modified.

Also provided is a desaturated fatty alcohol, a desaturated fatty acyl acetate or a desaturated fatty aldehyde obtainable by the methods disclosed herein.

Also provided is the use of a desaturated fatty alcohol, a desaturated fatty acyl acetate or a desaturated fatty aldehyde obtainable by the methods disclosed herein.

DETAILED DESCRIPTION OF THE INVENTION

Definitions

Figure 1:
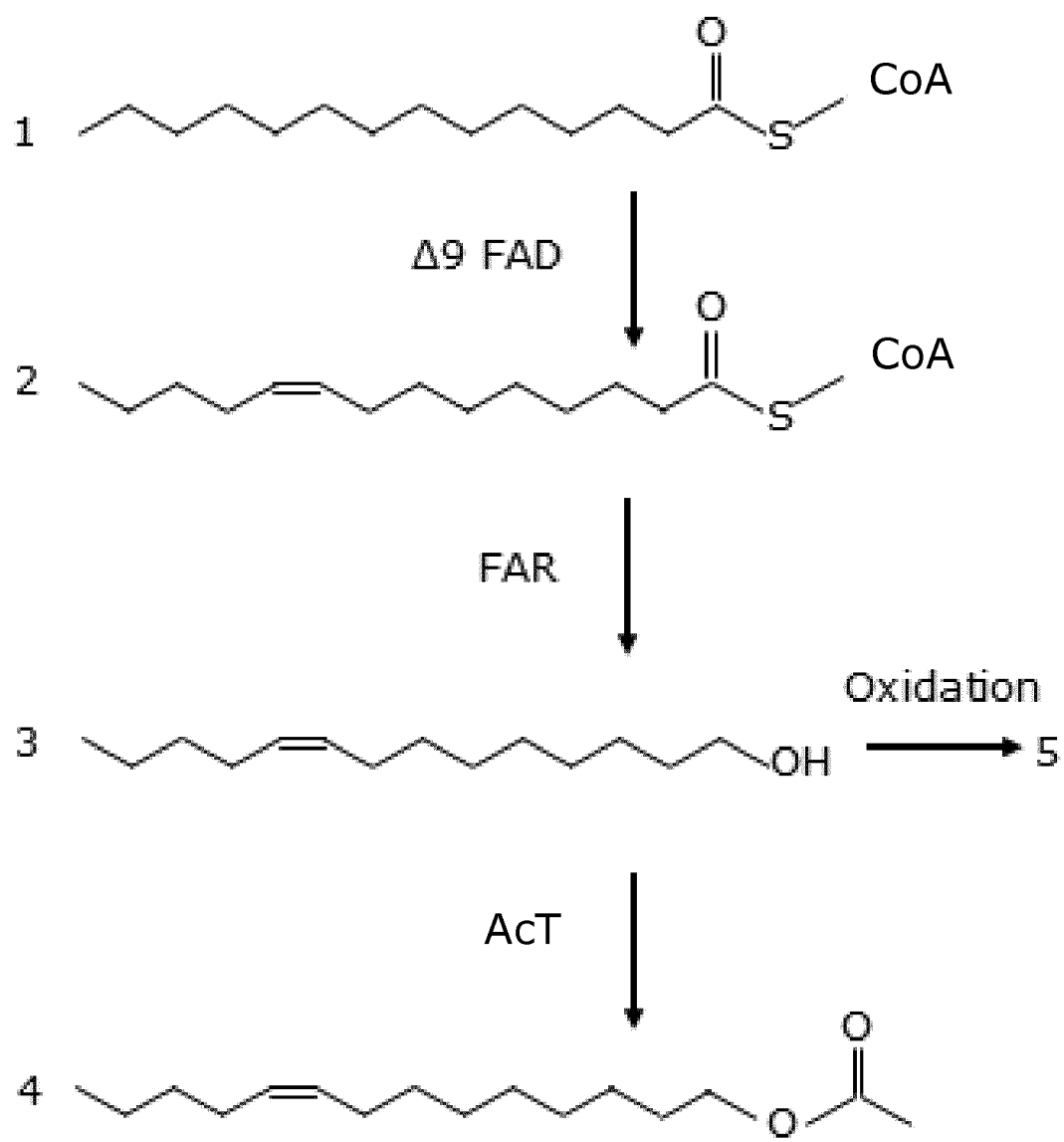
FIG. 1: pathway towards Z9-C14:OAc. (1) tetradecanoyl-CoA (myristoyl-CoA), 14:CoA (2) (Z)9-tetradecen-1-yl-CoA, Z9-14:CoA, (3) (Z)9-tetradecen-1-ol, Z9-14:OH, (4) (Z)9-tetradecen-1-yl acetate, Z9-14:OAc, (5) (Z)9-tetradecenal, Z9-14:Ald. Δ9 FAD-Z9-fatty acyl desaturase, FAR—fatty acyl-CoA reductase, AcT—acetyl-CoA transferase.

Biopesticide: the term 'biopesticide' is a contraction of 'biological pesticide' and refers to several types of pest management intervention: through predatory, parasitic, or chemical relationships. In the EU, biopesticides have been defined as "a form of pesticide based on micro-organisms or natural products". In the US, they are defined by the EPA as "including naturally occurring substances that control pests (biochemical pesticides), microorganisms that control pests (microbial pesticides), and pesticidal substances produced by plants containing added genetic material (plant-incorporated protectants) or PIPs". The present disclosure relates more particularly to biopesticides comprising natural products or naturally occurring substances. They are typically created by growing and concentrating naturally occurring organisms and/or their metabolites including bacteria and other microbes, fungi, nematodes, proteins, etc. They are often considered to be important components of integrated pest management (IPM) programmes, and have received much practical attention as substitutes to synthetic chemical plant protection products (PPPs). The Manual of Biocontrol Agents (2009: formerly the Biopesticide Manual) gives a review of the available biological insecticide (and other biology-based control) products.

Desaturated: the term "desaturated" will be herein used interchangeably with the term "unsaturated" and refers to a compound containing one or more double or triple carbon-carbon bonds.

Fatty acid: the term "fatty acid" refers to a carboxylic acid having a long aliphatic chain, i.e. an aliphatic chain between 4 and 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Most naturally occurring fatty acids are unbranched. They can be saturated, or desaturated.

Fatty acyl acetate: the term will herein be used interchangeably with "fatty acetate" and refers to an acetate having a fatty carbon chain, i.e. an aliphatic chain between 4 and 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Fatty acyl acetates can be saturated or desaturated.

Fatty acyl-CoA: the term will herein be used interchangeably with "fatty acyl-CoA ester", and refers to compounds of general formula R-CO-SCoA, where R is a fatty carbon chain. The fatty carbon chain is joined to the —SH group of coenzyme A by a thioester bond. Fatty acyl-CoAs can be saturated or desaturated, depending on whether the fatty acid which it is derived from is saturated or desaturated.

Fatty alcohol: the term "fatty alcohol" refers herein to an alcohol derived from a fatty acyl-CoA, having a carbon chain length of 4 to 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Fatty alcohols can be saturated or desaturated.

Fatty aldehyde: the term refers herein to an aldehyde derived from a fatty acyl-CoA, having a carbon chain length of 4 to 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Fatty aldehydes can be saturated or desaturated.

Heterologous: the term "heterologous" when referring to a polypeptide, such as a protein or an enzyme, or to a polynucleotide, shall herein be construed to refer to a polypeptide or a polynucleotide which is not naturally present in a wild type cell. For example, the term "heterologous Δ9 desaturase" when applied to *Yarrowia lipolytica* refers to a Δ9 desaturase which is not naturally present in a wild type *Y. lipolytica* cell, e.g. a Δ9 desaturase derived from *Drosophila melanogaster*.

Native: the term "native" when referring to a polypeptide, such as a protein or an enzyme, or to a polynucleotide, shall herein be construed to refer to a polypeptide or a polynucleotide which is naturally present in a wild type cell.

Pest: as used herein, the term 'pest' shall refer to an organism, in particular an animal, detrimental to humans or human concerns, in particular in the context of agriculture or livestock production. A pest is any living organism which is invasive or prolific, detrimental, troublesome, noxious, destructive, a nuisance to either plants or animals, human or human concerns, livestock, human structures, wild ecosystems etc. The term often overlaps with the related terms vermin, weed, plant and animal parasites and pathogens. It is possible for an organism to be a pest in one setting but beneficial, domesticated or acceptable in another.

Pheromone: pheromones are naturally occurring compounds designated by an unbranched aliphatic chain (between 9 and 18 carbons) ending in an alcohol, aldehyde or acetate functional group and containing up to 3 double bonds in the aliphatic backbone. Pheromone compositions may be produced chemically or biochemically, for example as described herein. Pheromones may thus comprise desaturated fatty alcohols, fatty aldehydes or fatty acyl acetates, such as can be obtained by the methods and cells described herein.

Reduced activity: the term "reduced activity" may herein refer to a total or a partial loss of activity of a given peptide, such as a protein or an enzyme. In some cases, peptides are encoded by essential genes, which cannot be deleted. In these cases, activity of the peptide can be reduced by methods known in the art, such as down-regulation of transcription or translation, or inhibition of the peptide. In other cases, the peptide is encoded by a non-essential gene, and the activity may be reduced or it may be completely lost, e.g. as a consequence of a deletion of the gene encoding the peptide.

Saturated: the term "saturated" refers to a compound which is devoid of double or triple carbon-carbon bonds.

The present disclosure relates to an oleaginous yeast cell useful for the production of *Lepidoptera* pheromones. The inventors have found that down-regulation of one or more of HFD1, HFD4, PEX10, FAO1 and GPAT in an oleaginous yeast cell, in particular in a *Y. lipolytica* cell, combined with heterologous expression of at least one heterologous desaturase and at least one heterologous fatty acyl-CoA reductase, results in the production of desaturated fatty alcohols useful for example for formulating pheromone compositions for pest management. In particular, down-regulation of PEX10 and one or more of HFD1, HFD4, FAO1 or GPAT is of interest. The cell may be further engineered to also allow production of fatty alcohol derivatives such as aldehydes and acetates, in particular desaturated fatty alcohol derivatives such as desaturated aldehydes and desaturated acetates, which are also useful for such pheromone compositions.

In one aspect, an oleaginous yeast cell is provided, which is capable of producing a desaturated fatty alcohol, said cell:
  i) expressing at least one heterologous desaturase capable of introducing at least one double bond in a fatty acyl-CoA; and
  ii) expressing at least one heterologous fatty acyl-CoA reductase, capable of converting at least part of said desaturated fatty acyl-CoA to a desaturated fatty alcohol; and
  iii) having reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or having reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In some embodiments, the yeast cell:
i) expresses at least one heterologous desaturase capable of introducing at least one double bond in a fatty acyl-CoA; and
ii) expresses at least one heterologous fatty acyl-CoA reductase, capable of converting at least part of said desaturated fatty acyl-CoA to a desaturated fatty alcohol; and
iii) has a mutation resulting in reduced activity of Pex10 (SEQ ID NO: 8) and a mutation resulting in reduced activity of at least one of Hfd1 (SEQ ID NO: 4), Hfd4 (SEQ ID NO: 6), Fao1 (SEQ ID NO: 22) and GPAT (SEQ ID NO: 10) or having a mutation resulting in reduced activity of at least one protein having at least 60% homology to Pex10 (SEQ ID NO: 8) and a mutation resulting in reduced activity of at least one of Hfd1 (SEQ ID NO: 4), Hfd4 (SEQ ID NO: 6), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8) and at least one of Hfd1 (SEQ ID NO: 4), Hfd4 (SEQ ID NO: 6), Fao1 (SEQ ID NO: 22) and GPAT (SEQ ID NO: 10).

Also provided is a method of producing a fatty alcohol in an oleaginous yeast cell, said method comprising the steps of providing a yeast cell and incubating said yeast cell in a medium, wherein the yeast cell:
i) expresses at least one heterologous desaturase capable of introducing at least one double bond in a fatty acyl-CoA, thereby converting at least part of said fatty acyl-CoA to a desaturated fatty acyl-CoA; and
ii) expresses at least one heterologous fatty acyl-CoA reductase, capable of converting at least part of said desaturated fatty acyl-CoA to a desaturated fatty alcohol, thereby producing said desaturated fatty alcohol; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In some embodiments, the method the steps of providing a yeast cell and incubating said yeast cell in a medium, wherein the yeast cell:
i) expresses at least one heterologous desaturase capable of introducing at least one double bond in a fatty acyl-CoA; and
ii) expresses at least one heterologous fatty acyl-CoA reductase, capable of converting at least part of said desaturated fatty acyl-CoA to a desaturated fatty alcohol; and
iii) has a mutation resulting in reduced activity of Pex10 (SEQ ID NO: 8) and a mutation resulting in reduced activity of at least one of Hfd1 (SEQ ID NO: 4), Hfd4 (SEQ ID NO: 6), Fao1 (SEQ ID NO: 22) and GPAT (SEQ ID NO: 10) or having a mutation resulting in reduced activity of at least one protein having at least 60% homology to Pex10 (SEQ ID NO: 8) and a mutation resulting in reduced activity of at least one of Hfd1 (SEQ ID NO: 4), Hfd4 (SEQ ID NO: 6), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8) and at least one of Hfd1 (SEQ ID NO: 4), Hfd4 (SEQ ID NO: 6), Fao1 (SEQ ID NO: 22) and GPAT (SEQ ID NO: 10).

Also provided is a nucleic acid construct for modifying a yeast cell, said construct comprising:
i) a first polynucleotide encoding at least one heterologous desaturase capable of introducing at least one double bond in a fatty acyl-CoA; and
ii) a second polynucleotide encoding at least one heterologous fatty acyl-CoA reductase (FAR), capable of converting at least part of said desaturated fatty acyl-CoA to a desaturated fatty alcohol; and iii) optionally, additional polynucleotides for reducing activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), wherein optionally the first polynucleotide and/or the second polynucleotide and/or the additional polynucleotides are under the control of a promoter.

Also provided is a kit of parts comprising a yeast cell as described herein and instructions for use; and/or a nucleic acid construct as described herein, wherein said construct is for modifying a yeast cell, and optionally a yeast cell to be modified.

Also provided is a desaturated fatty alcohol, a desaturated fatty acyl acetate or a desaturated fatty aldehyde obtainable by the methods described herein.

Also provided is the use of a desaturated fatty alcohol, a desaturated fatty acyl acetate or a desaturated fatty aldehyde obtainable by the present methods.

Desaturase (FAD)

In the present disclosure, the terms 'fatty acyl-CoA desaturase', 'desaturase', 'fatty acyl desaturase' and 'FAD' will be used interchangeably. The term refers to an enzyme capable of introducing at least one double bond in E/Z confirmations in an acyl-CoA having a chain length of 8, 9, 10, 11, 12, 13, 14, 15, 16, 17, 18, 19, 20, 21 or 22 carbon atoms. The double bond may be introduced in any position. For example, a desaturase introducing a double bond in position 3 is termed Δ3 desaturase. A desaturase introducing a double bond in position 5 is termed Δ5 desaturase. A desaturase introducing a double bond in position 6 is termed Δ6 desaturase. A desaturase introducing a double bond in position 7 is termed Δ7 desaturase. A desaturase introducing a double bond in position 8 is termed Δ8 desaturase. A desaturase introducing a double bond in position 9 is termed Δ9 desaturase. A desaturase introducing a double bond in position 10 is termed Δ10 desaturase. A desaturase introducing a double bond in position 11 is termed Δ11 desaturase. A desaturase introducing a double bond in position 12 is termed Δ12 desaturase. A desaturase introducing a double bond in position 13 is termed Δ13 desaturase. A desaturase introducing a double bond in position 14 is termed Δ14 desaturase. A desaturase introducing a double bond in position 15 is termed Δ15 desaturase. A desaturase introducing a double bond in position 16 is termed Δ16 desaturase. A desaturase introducing a double bond in position 17 is termed Δ17 desaturase. A desaturase introducing a double bond in position 18 is termed Δ18 desaturase. A desaturase introducing a double bond in position 19 is termed Δ19 desaturase. A desaturase introducing a double bond in position 20 is termed Δ20 desaturase.

Reductases reduce acyl-CoAs into alcohols of the corresponding chain length.

In one embodiment, the cell is capable of expressing at least one heterologous Δ5 desaturase. In another embodiment, the cell is capable of expressing at least one heterologous Δ6 desaturase. In another embodiment, the cell is capable of expressing at least one heterologous Δ7 desaturase. In another embodiment, the cell is capable of expressing at least one heterologous Δ8 desaturase. In another embodiment, the cell is capable of expressing at least one heterologous Δ9 desaturase. In another embodiment, the cell is capable of expressing at least one heterologous Δ10 desaturase. In another embodiment, the cell is capable of expressing at least one heterologous Δ11 desaturase. In another embodiment, the cell is capable of expressing at least one heterologous Δ12 desaturase. In another embodiment, the cell is capable of expressing at least one heterologous Δ13 desaturase. In another embodiment, the cell is capable of expressing at least one heterologous Δ14 desaturase. In another embodiment, the cell is capable of expressing at least one heterologous Δ15 desaturase. In another embodiment, the cell is capable of expressing at least one heterologous Δ16 desaturase. In another embodiment, the cell is capable of expressing at least one heterologous Δ17 desaturase. In another embodiment, the cell is capable of expressing at least one heterologous Δ18 desaturase. In another embodiment, the cell is capable of expressing at least one heterologous Δ19 desaturase. In another embodiment, the cell is capable of expressing at least one heterologous Δ20 desaturase.

The skilled person will know, depending on which desaturated fatty alcohol is desired, which kind of desaturase to use. For example, for the production of a fatty alcohol desaturated in position 11, a Δ11 desaturase having at least 60% homology to the Δ11 desaturase from *Amyelois transitella* as set forth in SEQ ID NO: 2, a Δ11 desaturase having at least 60% homology to the Δ11 desaturase from *Choristoneura rosaceana* as set forth in SEQ ID NO: 19 or a Δ11 desaturase having at least 60% homology to the Δ11 desaturase from *Choristoneura parallela* as set forth in SEQ ID NO: 20 may be used. Preferably, a Δ11 desaturase having at least 60% homology to the Δ11 desaturase from *Amyelois transitella* as set forth in SEQ ID NO: 2. If a fatty alcohol desaturated in position 9 is desired, a Δ9 desaturase having at least 60% homology to the Δ9 desaturase from *Drosophila melanogaster* as set forth in SEQ ID NO: 18 may be used. The gene encoding the heterologous desaturase may be codon-optimised for any purpose for the given host cell, e.g. *Yarrowia lipolytica*, as is known in the art. In one embodiment, the nucleic acid encoding the heterologous desaturase is as set forth in SEQ ID NO: 63 or a homologue thereof having at least 60% homology thereto, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% homology to SEQ ID NO: 63.

Accordingly, in one embodiment, the at least one heterologous desaturase is a Δ11 desaturase having at least 60% homology to the Δ11 desaturase from *Amyelois transitella* as set forth in SEQ ID NO: 2, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ11 desaturase from *Amyelois transitella* as set forth in SEQ ID NO: 2.

In one embodiment, the at least one heterologous desaturase is encoded by a nucleic acid having at least 60% homology to the nucleic acid encoding the Δ11 desaturase from *Amyelois transitella* as set forth in SEQ ID NO: 1, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the Δ11 desaturase from *Amyelois transitella* as set forth in SEQ ID NO: 1.

In another embodiment, the at least one heterologous desaturase is encoded by a nucleic acid having at least 60% homology to the nucleic acid encoding the Δ11 desaturase from *Amyelois transitella* as set forth in SEQ ID NO: 64, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the Δ11 desaturase from *Amyelois transitella* as set forth in SEQ ID NO: 64.

In another embodiment, the at least one heterologous desaturase is a Δ9 desaturase having at least 60% homology to the Δ9 desaturase having at least 60% homology to the Δ9 desaturase from *Drosophila melanogasteras* set forth in SEQ ID NO: 18, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Drosophila melanogaster* as set forth in SEQ ID NO: 18.

In one embodiment, the at least one heterologous desaturase is encoded by a nucleic acid having at least 60% homology to the nucleic acid encoding the Δ9 desaturase from *Drosophila melanogaster* as set forth in SEQ ID NO: 17, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding Δ9 desaturase having at least 60% homology to the Δ9 desaturase from *Drosophila melanogaster* as set forth in SEQ ID NO: 17.

In another embodiment, the at least one heterologous desaturase is encoded by a nucleic acid having at least 60% homology to the nucleic acid encoding the Δ9 desaturase from *Drosophila melanogasteras* set forth in SEQ ID NO: 63, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding Δ9 desaturase having at least 60% homology to the Δ9 desaturase from *Drosophila melanogasteras* set forth in SEQ ID NO: 63.

The heterologous desaturase may preferably be derived from an insect, for example from the order of Lepidoptera. In one embodiment, the heterologous desaturase is derived from *Amyelois transitella*. In another embodiment, the heterologous desaturase is derived from *Helicoverpa assulta*. In another embodiment, the heterologous desaturase is derived from *Helicoverpa armigera*. In another embodiment, the heterologous desaturase is derived from *Choristoneura rosaceana*. In another embodiment, the heterologous desaturase is derived from *Choristoneura parallela*.

A heterologous desaturase may be expressed from a nucleic acid introduced in the cell, e.g. on a vector such as a plasmid, or by genomic integration. The nucleic acid may be codon-optimised for any purpose as is known in the art for the specific yeast cell used.

The yeast cell to be modified may express a native desaturase, which may have a negative impact on the production of desaturated fatty alcohol and/or desaturated fatty acyl acetate. Accordingly, if the yeast cell to be modified expresses such a native desaturase, the cell may be modified so that activity of the native desaturase is reduced or absent.

To ensure lack of activity of a native desaturase, methods known in the art can be employed. The gene encoding the native desaturase may be deleted or partly deleted in order to ensure that the native desaturase is not expressed. Alternatively, the gene may be mutated so that the native desaturase is expressed but lacks activity, e.g. by mutation of the catalytical site of the enzyme. Alternatively, translation of mRNA to an active protein may be prevented by methods such as silencing RNA or siRNA. Alternatively, the yeast cell may be incubated in a medium comprising an inhibitor which inhibits activity of the native desaturase. A compound inhibiting transcription of the gene encoding the native desaturase may also be provided so that transcription is inactivated when said compound is present.

Inactivation of the native desaturase may thus be permanent or long-term, i.e. the modified yeast cell does not exhibit activity of the native desaturase in stable conditions, or it may be transient, i.e. the modified yeast cell may exhibit activity of the native desaturase for periods of time, but this activity can be suppressed for other periods of time.

Alcohol-Forming Fatty Acyl-CoA Reductase (EC 1.2.1.84)

The terms 'alcohol-forming fatty acyl-CoA reductase', 'fatty acyl-CoA reductase' and 'FAR' will be used herein interchangeably. The term "heterologous FAR" refers to a FAR which is not naturally expressed by the yeast cell.

FARs catalyse the two-step reaction (FIG. 1):

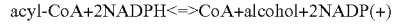

acyl-CoA+2NADPH<=>CoA+alcohol+2NADP(+)

wherein in a first step, the fatty acyl-CoA is reduced to a fatty aldehyde, before the fatty aldehyde is further reduced into a fatty alcohol in a second step. The fatty acyl-CoA may be a desaturated fatty acyl-CoA.

The FARs capable of catalyzing such reaction are alcohol-forming fatty acyl-CoA reductases with an EC number 1.2.1.84. The yeast cell of the present disclosure expresses at least one heterologous desaturase capable of introducing at least one double bond in a fatty acyl-CoA as described above, and at least one heterologous fatty acyl-CoA reductase capable of converting at least part of said desaturated fatty acyl-CoA to a desaturated fatty alcohol, and has moreover reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or having reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10). In some embodiments, the yeast cell expresses at least one heterologous desaturase, at least one heterologous fatty acyl-CoA reductase and has reduced activity of Pex10 and at least one of Hfd1, Hfd4, GPAT and Fao1 or a homologue thereof.

In some embodiments, the at least one heterologous FAR is derived from an organism belonging to the Lepidoptera order.

A heterologous fatty acyl-CoA reductase may be expressed from a nucleic acid introduced in the cell, e.g. on a vector such as a plasmid, or by genomic integration.

The nucleic acid may be codon-optimised for any purpose as is known in the art for the specific yeast cell used.

In one embodiment, the at least one heterologous FAR is capable of converting a Δ3 fatty acyl-CoA into a Δ3 fatty alcohol. In another embodiment, the at least one heterologous FAR is capable of converting a Δ5 fatty acyl-CoA into a Δ5 fatty alcohol.

In another embodiment, the at least one heterologous FAR is capable of converting a Δ6 fatty acyl-CoA into a Δ6 fatty alcohol. In another embodiment, the at least one heterologous FAR is capable of converting a Δ7 fatty acyl-CoA into a Δ7 fatty alcohol. In another embodiment, the at least one heterologous FAR is capable of converting a Δ8 fatty acyl-CoA into a Δ8 fatty alcohol. In another embodiment, the at least one heterologous FAR is capable of converting a Δ9 fatty acyl-CoA into a Δ9 fatty alcohol. In another embodiment, the at least one heterologous FAR is capable of converting a Δ10 fatty acyl-CoA into a Δ10 fatty alcohol. In another embodiment, the at least one heterologous FAR is capable of converting a Δ11 fatty acyl-CoA into a Δ11 fatty alcohol. In another embodiment, the at least one heterologous FAR is capable of converting a Δ12 fatty acyl-CoA into a Δ12 fatty alcohol. In another embodiment, the at least one heterologous FAR is capable of converting a Δ13 fatty acyl-CoA into a Δ13 fatty alcohol. In another embodiment, the at least one heterologous FAR is capable of converting a Δ14 fatty acyl-CoA into a Δ14 fatty alcohol. In another embodiment, the at least one heterologous FAR is capable of converting a Δ15 fatty acyl-CoA into a Δ15 fatty alcohol. In another embodiment, the at least one heterologous FAR is capable of converting a Δ16 fatty acyl-CoA into a Δ16 fatty alcohol. In another embodiment, the at least one heterologous FAR is capable of converting a Δ17 fatty acyl-CoA into a Δ17 fatty alcohol. In another embodiment, the at least one heterologous FAR is capable of converting a Δ18 fatty acyl-CoA into a Δ18 fatty alcohol. In another embodiment, the at least one heterologous FAR is capable of converting a Δ19 fatty acyl-CoA into a Δ19 fatty alcohol. In another embodiment, the at least one heterologous FAR is capable of converting a Δ20 fatty acyl-CoA into a Δ20 fatty alcohol. In another embodiment, the at least one heterologous FAR is capable of converting a Δ21 fatty acyl-CoA into a Δ21 fatty alcohol. In another embodiment, the at least one heterologous FAR is capable of converting a Δ22 fatty acyl-CoA into a Δ22 fatty alcohol.

In some embodiments, the FAR is selected from a FAR having at least 80% homology to the FAR derived from *Helicoverpa armigera*, as set forth in SEQ ID NO: 14, a FAR having at least 80% homology to the FAR from *Helicoverpa assulta* as set forth in SEQ ID NO: 16, a FAR having at least 80% homology to the FAR from *Heliothis subflexa* as set forth in SEQ ID NO: 12 and a FAR having at least 80% homology to the FAR from *Bicyclus anynana* as set forth in SEQ ID NO: 24. Preferably, the FAR is selected from a FAR having at least 80% homology to the FAR derived from *Helicoverpa armigera* and a FAR having at least 80% homology to the FAR from *Heliothis subflexa* as set forth in SEQ ID NO: 12.

In one embodiment, the FAR is Har_FAR (SEQ ID NO: 14, FAR from *Helicoverpa armigera*) or a variant thereof having at least 75% homology to Har_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Har_FAR (SEQ ID NO: 14).

In another embodiment, the FAR is Has_FAR (SEQ ID NO: 16, FAR from *Helicoverpa assulta*) or a variant thereof having at least 75% homology to Has_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Has_FAR (SEQ ID NO: 16).

In another embodiment, the FAR is Hs_FAR (SEQ ID NO: 12, FAR from *Heliothis subflexa*) or a variant thereof having at least 75% homology to Hs_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Hs_FAR (SEQ ID NO: 12).

In another embodiment, the FAR is Ban_FAR (SEQ ID NO: 24, FAR from *Bicyclus anynana*) or a variant thereof having at least 75% homology to Ban_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Ban_FAR (SEQ ID NO: 24).

In some embodiments, expression of the desaturase and/or of the FAR can be induced, for example if the genes encoding these enzymes are under the control of inducible promoters, as is known in the art. The yeast cell is incubated under suitable conditions, such as in an appropriate medium and at an appropriate temperature as is known to a person of skill in the art. Suitable media supporting yeast growth are known in the art and include, but are not limited to: undefined, complete media such as YEPD (or YPD, Yeast Extract Peptone Dextrose); defined, complete medium such as SC (Synthetic Complete); defined, drop-out medium such as SD (Synthetic Dextrose) lacking one or more elements such as an amino acid or an inducer; or mineral medium, consisting of salts, vitamins and a carbon source, and others.

Reduced Activity of Hfd1, Hfd4, Pex10, Fao1, GPAT or a Homologue Thereof

Throughout this disclosure, the term "reduced activity" may refer to a partial or a total loss activity. Reduced activity may be achieved by methods known in the art, e.g. by mutation or deletion of the gene encoding the peptide displaying said activity, by repression of transcription using a repressible promoter, by inhibition of the activity or by silencing at the translational level.

Peroxisome Biogenesis Factor 10 Pex10

In *Yarrowia lipolytica*, PEX10 (YAL10001023g, SEQ ID NO: 7) encodes the peroxisome biogenesis factor 10 (SEQ ID NO: 8). It is involved in import of peroxisomal matrix proteins and localizes to the peroxisomal membrane.

The inventors found that reduced activity of Pex10 resulted in increased titre of desaturated fatty alcohols in *Y. lipolytica*.

Accordingly, the oleaginous yeast cell of the present disclosure expresses at least one heterologous desaturase capable of introducing at least one double bond in a fatty acyl-CoA as described above, at least one heterologous fatty acyl-CoA reductase, capable of converting at least part of said desaturated fatty acyl-CoA to a desaturated fatty alcohol as described above, and has reduced activity of Pex10 or of a protein having at least 60% homology to Pex10 (SEQ ID NO: 8), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Pex10 (SEQ ID NO: 8).

Reduced or total loss of activity of Pex10 or of a protein having at least 60% homology thereto can be obtained by methods known in the art. In one embodiment, reduced activity is total loss of activity. For example, the gene encoding Pex10 or the protein having at least 60% homology thereto can be knocked out, or deleted, or its transcription can be prevented as is known in the art, for example by introducing a repressible promoter upstream of the gene resulting in total inactivation of transcription in the presence of a repressing compound.

In some embodiments, the gene encoding Pex10 or a protein having at least 60% homology thereto is deleted. In one embodiment, the gene is PEX10 (SEQ ID NO: 7) and the oleaginous yeast cell is *Yarrowia lipolytica*.

In one embodiment, the yeast cell expresses:
- at least one heterologous desaturase selected from the group consisting of a Δ11 desaturase having at least 60% homology to the Δ11 desaturase from *Amyelois transitella* as set forth in SEQ ID NO: 2, a Δ9 desaturase having at least 60% homology to the Δ9 desaturase from *Drosophila melanogaster* as set forth in SEQ ID NO: 18, a Δ11 desaturase having at least 60% homology to the Δ11 desaturase from *Choristoneura rosaceana* as set forth in SEQ ID NO: 19 and a Δ11 desaturase having at least 60% homology to the Δ11 desaturase from *Choristoneura parallela* as set forth in SEQ ID NO: 20; and
- at least one heterologous fatty acyl-CoA reductase selected from the group consisting of a FAR having at least 80% homology to the FAR from *Helicoverpa armigera* as set forth in SEQ ID NO: 14, a FAR having at least 80% homology to the FAR from *Helicoverpa assulta* as set forth in SEQ ID NO: 16, a FAR having at least 80% homology to the FAR from *Heliothis subflexa* as set forth in SEQ ID NO: 12 and a FAR having at least 80% homology to the FAR from *Bicyclus anynana* as set forth in SEQ ID NO: 24; preferably, the FAR is selected from a FAR having at least 80% homology to the FAR derived from *Helicoverpa armigera* as set forth in SEQ ID NO: 14 and a FAR having at least 80% homology to the FAR from *Heliothis subflexa* as set forth in SEQ ID NO: 12; and
- has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In one embodiment, the yeast cell expresses:
- at least one heterologous desaturase having at least 60% homology to the Δ11 desaturase from *Amyelois transitella* as set forth in SEQ ID NO: 2; and
- at least one heterologous fatty acyl-CoA reductase having at least 80% homology to the FAR from *Helicoverpa armigera* as set forth in SEQ ID NO: 14; and
- has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
- at least one heterologous desaturase having at least 60% homology to the Δ9 desaturase from *Drosophila melanogasteras* set forth in SEQ ID NO: 18; and
- at least one heterologous fatty acyl-CoA reductase having at least 80% homology to the FAR from *Helicoverpa armigera* as set forth in SEQ ID NO: 14; and
- has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
- at least one heterologous desaturase having at least 60% homology to the Δ11 desaturase from *Amyelois transitella* as set forth in SEQ ID NO: 2; and
- at least one heterologous fatty acyl-CoA reductase having at least 80% homology to the FAR from *Helicoverpa assulta* as set forth in SEQ ID NO: 16; and
- has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
- at least one heterologous desaturase having at least 60% homology to the Δ9 desaturase from *Drosophila melanogasteras* set forth in SEQ ID NO: 18; and
- at least one heterologous fatty acyl-CoA reductase having at least 80% homology to the FAR from *Helicoverpa assulta* as set forth in SEQ ID NO: 16; and
- has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Heliothis subflexa* as set forth in SEQ ID NO: 12; and
has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Heliothis subflexa* as set forth in SEQ ID NO: 12; and
has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Bicyclus anynana* as set forth in SEQ ID NO: 24; and
has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Bicyclus anynana* as set forth in SEQ ID NO: 24; and
has reduced activity or total loss of activity of Pex10 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8).

In preferred embodiments, the yeast cell is a *Yarrowia* cell, such as a *Yarrowia lipolytica* cell.

Fatty Aldehyde Dehydrogenase Hfd1

In *Yarrowia lipolytica*, HFD1 (YAL10F23793g, SEQ ID NO: 3) encodes a fatty aldehyde dehydrogenase (SEQ ID NO: 4). It catalyses the oxidation of fatty aldehydes to fatty acids.

The inventors found that reduced activity of Hfd1 resulted in increased titre of desaturated fatty alcohols in oleaginous yeast cells such as *Y. lipolytica*. In specific embodiments, the yeast cell also has reduced or total loss of activity of Pex10 or of a protein having at least 60% homology to Pex10 (SEQ ID NO: 8), as described above.

Accordingly, the oleaginous yeast cell of the present disclosure expresses at least one heterologous desaturase capable of introducing at least one double bond in a fatty acyl-CoA as described above, at least one heterologous fatty acyl-CoA reductase, capable of converting at least part of said desaturated fatty acyl-CoA to a desaturated fatty alcohol as described above, and has reduced activity of Hfd1 or of a protein having at least 60% homology to Hfd1 (SEQ ID NO: 4), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 (SEQ ID NO: 4).

In specific embodiments, the yeast cell also has reduced or total loss of activity of Pex10 or of a protein having at least 60% homology to Pex10 (SEQ ID NO: 8), as described above.

Reduced activity of Hfd1 or of a protein having at least 60% homology thereto can be obtained by methods known in the art. In one embodiment, reduced activity is total loss of activity. For example, the gene encoding Hfd1 or the protein having at least 60% homology thereto can be knocked out, or deleted, or its transcription can be prevented as is known in the art, for example by introducing a repressible promoter upstream of the gene resulting in total inactivation of transcription in the presence of a repressing compound.

In some embodiments, the gene encoding Hfd1 or a protein having at least 60% homology thereto is deleted. In one embodiment, the gene is HFD1 (SEQ ID NO: 3) and the oleaginous yeast cell is *Yarrowia lipolytica*.

In one embodiment, the yeast cell expresses:
- at least one heterologous desaturase selected from the group consisting of a Δ11 desaturase having at least 60% homology to the Δ11 desaturase from *Amyelois transitella* as set forth in SEQ ID NO: 2, a Δ9 desaturase having at least 60% homology to the Δ9 desaturase from *Drosophila melanogaster* as set forth in SEQ ID NO: 18, a Δ11 desaturase having at least 60% homology to the Δ11 desaturase from *Choristoneura rosaceana* as set forth in SEQ ID NO: 19 and a Δ11 desaturase having at least 60% homology to the Δ11 desaturase from *Choristoneura parallela* as set forth in SEQ ID NO: 20; preferably the at least one heterologous desaturase is a Δ11 desaturase having at least 60% homology to the Δ11 desaturase from *Amyelois transitella* as set forth in SEQ ID NO: 2 or a Δ9 desaturase having at least 60% homology to the Δ9 desaturase from *Drosophila melanogasteras* set forth in SEQ ID NO: 18; and
- at least one heterologous fatty acyl-CoA reductase selected from the group consisting of a FAR having at least 80% homology to the FAR from *Helicoverpa armigera* as set forth in SEQ ID NO: 14, a FAR having at least 80% homology to the FAR from *Helicoverpa assulta* as set forth in SEQ ID NO: 16, a FAR having at least 80% homology to the FAR from *Heliothis subflexa* as set forth in SEQ ID NO: 12 and a FAR having at least 80% homology to the FAR from *Bicyclus anynana* as set forth in SEQ ID NO: 24; preferably, the FAR is selected from a FAR having at least 80% homology to the FAR derived from *Helicoverpa armigera* as set forth in SEQ ID NO: 14 and a FAR having at least 80% homology to the FAR from *Heliothis subflexa* as set forth in SEQ ID NO: 12; and
- has reduced activity or total loss of activity of Hfd1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 (SEQ ID NO: 4).

In specific embodiments, the yeast cell has reduced or total loss of activity of at least Pex10 or a protein having at least 60% homology to Pex10 (SEQ ID NO: 8).

In one embodiment, the yeast cell expresses:
- at least one heterologous desaturase having at least 60% homology to the Δ11 desaturase from *Amyelois transitella* as set forth in SEQ ID NO: 2; and
- at least one heterologous fatty acyl-CoA reductase having at least 80% homology to the FAR from *Helicoverpa armigera* as set forth in SEQ ID NO: 14; and
- has reduced activity or total loss of activity of Hfd1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
- at least one heterologous desaturase having at least 60% homology to the Δ9 desaturase from *Drosophila melanogasteras* set forth in SEQ ID NO: 18; and
- at least one heterologous fatty acyl-CoA reductase having at least 80% homology to the FAR from *Helicoverpa armigera* as set forth in SEQ ID NO: 14; and
- has reduced activity or total loss of activity of Hfd1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
- at least one heterologous desaturase having at least 60% homology to the Δ11 desaturase from *Amyelois transitella* as set forth in SEQ ID NO: 2; and
- at least one heterologous fatty acyl-CoA reductase having at least 80% homology to the FAR from *Helicoverpa assulta* as set forth in SEQ ID NO: 16; and has reduced activity or total loss of activity of Hfd1 or of
a protein having at least 65% homology thereto, such as
at least 70% homology, such as at least 75% homology,
such as at least 80% homology, such as at least 81%
homology, such as at least 82% homology, such as at
least 83% homology, such as at least 84% homology,
such as at least 85% homology, such as at least 86%
homology, such as at least 87% homology, such as at
least 88% homology, such as at least 89% homology,
such as at least 90% homology, such as at least 91%
homology, such as at least 92% homology, such as at
least 93% homology, such as at least 94% homology,
such as at least 95% homology, such as at least 96%
homology, such as at least 97% homology, such as at
least 98% homology, such as at least 99% homology to
Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Helicoverpa assulta* as set forth in SEQ ID NO: 16; and
has reduced activity or total loss of activity of Hfd1 or of
a protein having at least 65% homology thereto, such as
at least 70% homology, such as at least 75% homology,
such as at least 80% homology, such as at least 81%
homology, such as at least 82% homology, such as at
least 83% homology, such as at least 84% homology,
such as at least 85% homology, such as at least 86%
homology, such as at least 87% homology, such as at
least 88% homology, such as at least 89% homology,
such as at least 90% homology, such as at least 91%
homology, such as at least 92% homology, such as at
least 93% homology, such as at least 94% homology,
such as at least 95% homology, such as at least 96%
homology, such as at least 97% homology, such as at
least 98% homology, such as at least 99% homology to
Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Heliothis subflexa* as set forth in SEQ ID NO: 12; and
has reduced activity or total loss of activity of Hfd1 or of
a protein having at least 65% homology thereto, such as
at least 70% homology, such as at least 75% homology,
such as at least 80% homology, such as at least 81%
homology, such as at least 82% homology, such as at
least 83% homology, such as at least 84% homology,
such as at least 85% homology, such as at least 86%
homology, such as at least 87% homology, such as at
least 88% homology, such as at least 89% homology,
such as at least 90% homology, such as at least 91%
homology, such as at least 92% homology, such as at
least 93% homology, such as at least 94% homology,
such as at least 95% homology, such as at least 96%
homology, such as at least 97% homology, such as at
least 98% homology, such as at least 99% homology to
Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Heliothis subflexa* as set forth in SEQ ID NO: 12; and
has reduced activity or total loss of activity of Hfd1 or of
a protein having at least 65% homology thereto, such as
at least 70% homology, such as at least 75% homology,
such as at least 80% homology, such as at least 81%
homology, such as at least 82% homology, such as at
least 83% homology, such as at least 84% homology,
such as at least 85% homology, such as at least 86%
homology, such as at least 87% homology, such as at
least 88% homology, such as at least 89% homology,
such as at least 90% homology, such as at least 91%
homology, such as at least 92% homology, such as at
least 93% homology, such as at least 94% homology,
such as at least 95% homology, such as at least 96%
homology, such as at least 97% homology, such as at
least 98% homology, such as at least 99% homology to
Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Bicyclus anynana* as set forth in SEQ ID NO: 24; and
has reduced activity or total loss of activity of Hfd1 or of
a protein having at least 65% homology thereto, such as
at least 70% homology, such as at least 75% homology,
such as at least 80% homology, such as at least 81%
homology, such as at least 82% homology, such as at
least 83% homology, such as at least 84% homology,
such as at least 85% homology, such as at least 86%
homology, such as at least 87% homology, such as at
least 88% homology, such as at least 89% homology,
such as at least 90% homology, such as at least 91%
homology, such as at least 92% homology, such as at
least 93% homology, such as at least 94% homology,
such as at least 95% homology, such as at least 96%
homology, such as at least 97% homology, such as at
least 98% homology, such as at least 99% homology to
Hfd1 (SEQ ID NO: 4).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and at least one heterologous fatty acyl-CoA reductase having
at least 80% homology to the FAR from *Bicyclus
anynana* as set forth in SEQ ID NO: 24; and
has reduced activity or total loss of activity of Hfd1 or of
a protein having at least 65% homology thereto, such as
at least 70% homology, such as at least 75% homology,
such as at least 80% homology, such as at least 81%
homology, such as at least 82% homology, such as at
least 83% homology, such as at least 84% homology,
such as at least 85% homology, such as at least 86%
homology, such as at least 87% homology, such as at
least 88% homology, such as at least 89% homology,
such as at least 90% homology, such as at least 91%
homology, such as at least 92% homology, such as at
least 93% homology, such as at least 94% homology,
such as at least 95% homology, such as at least 96%
homology, such as at least 97% homology, such as at
least 98% homology, such as at least 99% homology to
Hfd1 (SEQ ID NO: 4).

In specific embodiments, the yeast cell also has reduced or total loss of activity of Pex10 or of a protein having at least 60% homology to Pex10 (SEQ ID NO: 8), as described above.

Fatty Aldehyde Dehydrogenase Hfd4

In *Yarrowia lipolytica*, HFD4 (YAL10B01298g, SEQ ID NO: 5 encodes a fatty aldehyde dehydrogenase (SEQ ID NO: 6). It catalyses the oxidation of fatty aldehydes to fatty acids.

The inventors found that reduced activity of Hfd4 resulted in increased titre of desaturated fatty alcohols in *Y. lipolytica*. In specific embodiments, the yeast cell also has reduced or total loss of activity of Pex10 or of a protein having at least 60% homology to Pex10 (SEQ ID NO: 8), as described above.

Accordingly, the oleaginous yeast cell of the present disclosure expresses at least one heterologous desaturase capable of introducing at least one double bond in a fatty acyl-CoA as described above, at least one heterologous fatty acyl-CoA reductase, capable of converting at least part of said desaturated fatty acyl-CoA to a desaturated fatty alcohol as described above, and has reduced activity of Hfd4 or of a protein having at least 60% homology to Hfd4 (SEQ ID NO: 6), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

Reduced activity of Hfd4 or of a protein having at least 60% homology thereto can be obtained by methods known in the art. In one embodiment, reduced activity is total loss of activity. For example, the gene encoding Hfd4 or the protein having at least 60% homology thereto can be knocked out, or deleted, or its transcription can be prevented as is known in the art, for example by introducing a repressible promoter upstream of the gene resulting in total inactivation of transcription in the presence of a repressing compound.

In some embodiments, the gene encoding Hfd4 or a protein having at least 60% homology thereto is deleted. In one embodiment, the gene is HFD4 (SEQ ID NO: 5) and the oleaginous yeast cell is *Yarrowia lipolytica*.

In one embodiment, the yeast cell expresses:
at least one heterologous desaturase selected from the group consisting of a Δ11 desaturase having at least 60% homology to the Δ11 desaturase from *Amyelois transitella* as set forth in SEQ ID NO: 2, a Δ9 desaturase having at least 60% homology to the Δ9 desaturase from *Drosophila melanogaster* as set forth in SEQ ID NO: 18, a Δ11 desaturase having at least 60% homology to the Δ11 desaturase from *Choristoneura rosaceana* as set forth in SEQ ID NO: 19 and a Δ11 desaturase having at least 60% homology to the Δ11 desaturase from *Choristoneura parallela* as set forth in SEQ ID NO: 20; preferably the at least one heterologous desaturase is a Δ11 desaturase having at least 60% homology to the Δ11 desaturase from *Amyelois transitella* as set forth in SEQ ID NO: 2 or a Δ9 desaturase having at least 60% homology to the Δ9 desaturase from *Drosophila melanogasteras* set forth in SEQ ID NO: 18; and
at least one heterologous fatty acyl-CoA reductase selected from the group consisting of a FAR having at least 80% homology to the FAR from *Helicoverpa armigera* as set forth in SEQ ID NO: 14, a FAR having at least 80% homology to the FAR from *Helicoverpa assulta* as set forth in SEQ ID NO: 16, a FAR having at least 80% homology to the FAR from *Heliothis subflexa* as set forth in SEQ ID NO: 12 and a FAR having at least 80% homology to the FAR from *Bicyclus anynana* as set forth in SEQ ID NO: 24; preferably, the FAR is selected from a FAR having at least 80% homology to the FAR derived from *Helicoverpa armigera* as set forth in SEQ ID NO: 14 and a FAR having at least 80% homology to the FAR from *Heliothis subflexa* as set forth in SEQ ID NO: 12; and
has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In one embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Helicoverpa armigera* as set forth in SEQ ID NO: 14; and
has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Helicoverpa armigera* as set forth in SEQ ID NO: 14; and
has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Helicoverpa assulta* as set forth in SEQ ID NO: 16; and
has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Helicoverpa assulta* as set forth in SEQ ID NO: 16; and
has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Heliothis subflexa* as set forth in SEQ ID NO: 12; and
has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and at least one heterologous fatty acyl-CoA reductase having at least 80% homology to the FAR from *Heliothis subflexa* as set forth in SEQ ID NO: 12; and has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ11 desaturase from *Amyelois transitella* as set forth in SEQ ID NO: 2; and at least one heterologous fatty acyl-CoA reductase having at least 80% homology to the FAR from *Bicyclus anynana* as set forth in SEQ ID NO: 24; and has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ9 desaturase from *Drosophila melanogasteras* set forth in SEQ ID NO: 18; and at least one heterologous fatty acyl-CoA reductase having at least 80% homology to the FAR from *Bicyclus anynana* as set forth in SEQ ID NO: 24; and has reduced activity or total loss of activity of Hfd4 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 (SEQ ID NO: 6).

In specific embodiments, the yeast cell also has reduced or total loss of activity of Pex10 or of a protein having at least 60% homology to Pex10 (SEQ ID NO: 8), as described above.

In preferred embodiments, the yeast cell is a *Yarrowia* cell, such as a *Yarrowia lipolytica* cell.

Fatty Alcohol Oxidase Fao1

In *Yarrowia lipolytica*, FAO1 (YALI0B14014g, SEQ ID NO: 21) encodes a fatty alcohol oxidase (SEQ ID NO: 22). Its deletion results in increased accumulation of w-hydroxy fatty acids.

The inventors found that reduced activity of Fao1 resulted in increased titre of desaturated fatty alcohols in *Y. lipolytica*. In specific embodiments, the yeast cell also has reduced or total loss of activity of Pex10 or of a protein having at least 60% homology to Pex10 (SEQ ID NO: 8), as described above.

Accordingly, the oleaginous yeast cell of the present disclosure expresses at least one heterologous desaturase capable of introducing at least one double bond in a fatty acyl-CoA as described above, at least one heterologous fatty acyl-CoA reductase, capable of converting at least part of said desaturated fatty acyl-CoA to a desaturated fatty alcohol as described above, and has reduced activity of Fao1 or of a protein having at least 60% homology to Fao1 (SEQ ID NO: 22), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Fao1 (SEQ ID NO: 22).

Reduced activity of Fao1 or of a protein having at least 60% homology thereto can be obtained by methods known in the art. In one embodiment, reduced activity is total loss of activity. For example, the gene encoding Fao1 or the protein having at least 60% homology thereto can be knocked out, or deleted, or its transcription can be prevented as is known in the art, for example by introducing a repressible promoter upstream of the gene resulting in total inactivation of transcription in the presence of a repressing compound.

In some embodiments, the gene encoding Fao1 or a protein having at least 60% homology thereto is deleted. In one embodiment, the gene is Fao1 (SEQ ID NO: 21) and the oleaginous yeast cell is *Yarrowia lipolytica*.

In one embodiment, the yeast cell expresses:

at least one heterologous desaturase selected from the group consisting of a Δ11 desaturase having at least 60% homology to the Δ11 desaturase from *Amyelois transitella* as set forth in SEQ ID NO: 2, a Δ9 desaturase having at least 60% homology to the Δ9 desaturase from *Drosophila melanogaster* as set forth in SEQ ID NO: 18, a Δ11 desaturase having at least 60% homology to the Δ11 desaturase from *Choristoneura rosaceana* as set forth in SEQ ID NO: 19 and a Δ11 desaturase having at least 60% homology to the Δ11 desaturase from *Choristoneura parallela* as set forth in SEQ ID NO: 20; preferably the at least one heterologous desaturase is a Δ11 desaturase having at least 60% homology to the Δ11 desaturase from *Amyelois transitella* as set forth in SEQ ID NO: 2 or a Δ9 desaturase having at least 60% homology to the Δ9 desaturase from *Drosophila melanogasteras* set forth in SEQ ID NO: 18; and at least one heterologous fatty acyl-CoA reductase selected from the group consisting of a FAR having at least 80% homology to the FAR from *Helicoverpa armigera* as set forth in SEQ ID NO: 14, a FAR having at least 80% homology to the FAR from *Helicoverpa assulta* as set forth in SEQ ID NO: 16, a FAR having at least 80% homology to the FAR from *Heliothis subflexa* as set forth in SEQ ID NO: 12 and a FAR having at least 80% homology to the FAR from *Bicyclus anynana* as set forth in SEQ ID NO: 24; preferably, the FAR is selected from a FAR having at least 80% homology to the FAR derived from *Helicoverpa armigera* as set forth in SEQ ID NO: 14 and a FAR having at least 80% homology to the FAR from *Heliothis subflexa* as set forth in SEQ ID NO: 12; and has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In one embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Helicoverpa armigera* as set forth in SEQ ID NO: 14 and
has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Helicoverpa armigera* as set forth in SEQ ID NO: 14 and
has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Helicoverpa assulta* as set forth in SEQ ID NO: 16; and
has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and at least one heterologous fatty acyl-CoA reductase having at least 80% homology to the FAR from *Helicoverpa assulta* as set forth in SEQ ID NO: 16; and has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ11 desaturase from *Amyelois transitella* as set forth in SEQ ID NO: 2; and at least one heterologous fatty acyl-CoA reductase having at least 80% homology to the FAR from *Heliothis subflexa* as set forth in SEQ ID NO: 12; and has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ9 desaturase from *Drosophila melanogasteras* set forth in SEQ ID NO: 18; and at least one heterologous fatty acyl-CoA reductase having at least 80% homology to the FAR from *Heliothis subflexa* as set forth in SEQ ID NO: 12; and has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ11 desaturase from *Amyelois transitella* as set forth in SEQ ID NO: 2; and at least one heterologous fatty acyl-CoA reductase having at least 80% homology to the FAR from *Bicyclus anynana* as set forth in SEQ ID NO: 24; and has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ9 desaturase from *Drosophila melanogasteras* set forth in SEQ ID NO: 18; and at least one heterologous fatty acyl-CoA reductase having at least 80% homology to the FAR from *Bicyclus anynana* as set forth in SEQ ID NO: 24; and has reduced activity or total loss of activity of Fao1 or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 (SEQ ID NO: 22).

In specific embodiments, the yeast cell also has reduced or total loss of activity of Pex10 or of a protein having at least 60% homology to Pex10 (SEQ ID NO: 8), as described above.

In preferred embodiments, the yeast cell is a *Yarrowia* cell, such as a *Yarrowia lipolytica* cell.

Glycerol-3-phosphate Acyltransferase GPAT

In *Yarrowia lipolytica*, GPAT (YALI0C00209g, SEQ ID NO: 9) encodes a glycerol-3-phosphate acyltransferase (SEQ ID NO: 10). GPAT catalyzes the first reaction towards glycerolipids biosynthesis. The gene is essential in *Yarrowia lipolytica*.

The inventors found that reduced activity of Fao1 resulted in increased titre of desaturated fatty alcohols in *Y. lipolytica*. In specific embodiments, the yeast cell also has reduced or total loss of activity of Pex10 or of a protein having at least 60% homology to Pex10 (SEQ ID NO: 8), as described above.

Accordingly, the oleaginous yeast cell of the present disclosure expresses at least one heterologous desaturase capable of introducing at least one double bond in a fatty acyl-CoA as described above, at least one heterologous fatty acyl-CoA reductase, capable of converting at least part of said desaturated fatty acyl-CoA to a desaturated fatty alcohol as described above, and has reduced activity of Fao1 or of a protein having at least 60% homology to GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of GPAT (SEQ ID NO: 10).

Reduced activity of GPAT or of a protein having at least 60% homology thereto can be obtained by methods known in the art. In one embodiment, reduced activity is partial loss of activity. For example, the gene encoding GPAT or the protein having at least 60% homology thereto can be mutated or its transcription can be reduced as is known in the art, for example by introducing a repressible promoter upstream of the gene resulting in partial inactivation of transcription in the presence of a repressing compound. If the yeast cell is *Yarrowia lipolytica*, GPAT activity is reduced without deleting the gene.

In one embodiment, the yeast cell expresses:
at least one heterologous desaturase selected from the group consisting of a Δ11 desaturase having at least 60% homology to the Δ11 desaturase from *Amyelois transitella* as set forth in SEQ ID NO: 2, a Δ9 desaturase having at least 60% homology to the Δ9 desaturase from *Drosophila melanogaster* as set forth in SEQ ID NO: 18, a Δ11 desaturase having at least 60% homology to the Δ11 desaturase from *Choristoneura rosaceana* as set forth in SEQ ID NO: 19 and a Δ11 desaturase having at least 60% homology to the Δ11 desaturase from *Choristoneura parallela* as set forth in SEQ ID NO: 20; preferably the at least one heterologous desaturase is a Δ11 desaturase having at least 60% homology to the Δ11 desaturase from *Amyelois transitella* as set forth in SEQ ID NO: 2 or a Δ9 desaturase having at least 60% homology to the Δ9 desaturase from *Drosophila melanogasteras* set forth in SEQ ID NO: 18; and
at least one heterologous fatty acyl-CoA reductase selected from the group consisting of a FAR having at least 80% homology to the FAR from *Helicoverpa armigera* as set forth in SEQ ID NO: 14, a FAR having at least 80% homology to the FAR from *Helicoverpa assulta* as set forth in SEQ ID NO: 16, a FAR having at least 80% homology to the FAR from *Heliothis subflexa* as set forth in SEQ ID NO: 12 and a FAR having at least 80% homology to the FAR from *Bicyclus anynana* as set forth in SEQ ID NO: 24; preferably, the FAR is selected from a FAR having at least 80% homology to the FAR derived from *Helicoverpa armigera* as set forth in SEQ ID NO: 14 and a FAR having at least 80% homology to the FAR from *Heliothis subflexa* as set forth in SEQ ID NO: 12; and has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In one embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Helicoverpa armigera* as set forth in SEQ ID NO: 14; and
has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Helicoverpa armigera* as set forth in SEQ ID NO: 14; and has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Helicoverpa assulta* as set forth in SEQ ID NO: 16; and
has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Helicoverpa assulta* as set forth in SEQ ID NO: 16; and
has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and
at least one heterologous fatty acyl-CoA reductase having at least 80% homology to the FAR from *Heliothis subflexa* as set forth in SEQ ID NO: 12; and
has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ9 desaturase from *Drosophila melanogasteras* set forth in SEQ ID NO: 18; and
at least one heterologous fatty acyl-CoA reductase having at least 80% homology to the FAR from *Heliothis subflexa* as set forth in SEQ ID NO: 12; and
has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:
at least one heterologous desaturase having at least 60% homology to the Δ11 desaturase from *Amyelois transitella* as set forth in SEQ ID NO: 2; and at least one heterologous fatty acyl-CoA reductase having at least 80% homology to the FAR from *Bicyclus anynana* as set forth in SEQ ID NO: 24; and has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In another embodiment, the yeast cell expresses:

at least one heterologous desaturase having at least 60% homology to the Δ9 desaturase from *Drosophila melanogasteras* set forth in SEQ ID NO: 18; and at least one heterologous fatty acyl-CoA reductase having at least 80% homology to the FAR from *Bicyclus anynana* as set forth in SEQ ID NO: 24; and has reduced activity or total loss of activity of GPAT or of a protein having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to GPAT (SEQ ID NO: 10).

In specific embodiments, the yeast cell also has reduced or total loss of activity of Pex10 or of a protein having at least 60% homology to Pex10 (SEQ ID NO: 8), as described above.

In preferred embodiments, the yeast cell is a *Yarrowia* cell, such as a *Yarrowia lipolytica* cell.

Reduction of Activity of Two or More of Hfd1, Hfd4, Pex10, Fao1 and GPAT

It may be advantageous to reduce activity of more than one of the above listed proteins. In some embodiments, the yeast cell has reduced or total loss of activity of Pex10 or of a protein having at least 60% homology to Pex10 (SEQ ID NO: 8), as described above, and of one or more of Hfd1, Hfd4, Fao1 and GPAT, or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4, to Hfd4 as set forth in SEQ ID NO: 6, to Fao1 as set forth in SEQ ID NO: 22 or to GPAT as set forth in SEQ ID NO: 10.

Accordingly, in some embodiments the yeast cell has reduced activity of two or more of Hfd1, Hfd4, Pex10, Fao1 and GPAT, or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4, to Hfd4 as set forth in SEQ ID NO: 6, to Pex10 as set forth in SEQ ID NO: 8, to Fao1 as set forth in SEQ ID NO: 22 or to GPAT as set forth in SEQ ID NO: 10.

In one embodiment, the yeast cell expresses at least one heterologous desaturase as described above and at least one fatty acyl-CoA reductase as described above, and has reduced activity of Hfd1 and Hfd4 or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4 or Hfd4 as set forth in SEQ ID NO: 6.

In another embodiment, the yeast cell expresses at least one heterologous desaturase as described above and at least one fatty acyl-CoA reductase as described above, and has reduced activity of Hfd1 and Pex10 or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4 or to Pex10 as set forth in SEQ ID NO: 8.

In another embodiment, the yeast cell expresses at least one heterologous desaturase as described above and at least one fatty acyl-CoA reductase as described above, and has reduced activity of Hfd1 and Fao1 or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4 or to Fao1 as set forth in SEQ ID NO: 22.

In another embodiment, the yeast cell expresses at least one heterologous desaturase as described above and at least one fatty acyl-CoA reductase as described above, and has reduced activity of Hfd1 and GPAT or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4 or to GPAT as set forth in SEQ ID NO: 10.

In another embodiment, the yeast cell expresses at least one heterologous desaturase as described above and at least one fatty acyl-CoA reductase as described above, and has reduced activity of Hfd4 and Pex10 or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 as set forth in SEQ ID NO: 6 or to Pex10 as set forth in SEQ ID NO: 8.

In another embodiment, the yeast cell expresses at least one heterologous desaturase as described above and at least one fatty acyl-CoA reductase as described above, and has reduced activity of Hfd4 and Fao1 or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 as set forth in SEQ ID NO: 6 or to Fao1 as set forth in SEQ ID NO: 22.

In another embodiment, the yeast cell expresses at least one heterologous desaturase as described above and at least one fatty acyl-CoA reductase as described above, and has reduced activity of Hfd4 and GPAT or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd4 as set forth in SEQ ID NO: 6 or to GPAT as set forth in SEQ ID NO: 10.

In another embodiment, the yeast cell expresses at least one heterologous desaturase as described above and at least one fatty acyl-CoA reductase as described above, and has reduced activity of Pex10 and Fao1 or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 as set forth in SEQ ID NO: 8 or to Fao1 as set forth in SEQ ID NO: 22.

In another embodiment, the yeast cell expresses at least one heterologous desaturase as described above and at least one fatty acyl-CoA reductase as described above, and has reduced activity of Pex10 and GPAT or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 as set forth in SEQ ID NO: 8 or to GPAT as set forth in SEQ ID NO: 10.

In another embodiment, the yeast cell expresses at least one heterologous desaturase as described above and at least one fatty acyl-CoA reductase as described above, and has reduced activity of Fao1 and GPAT or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Fao1 as set forth in SEQ ID NO: 22 or to GPAT as set forth in SEQ ID NO: 10.

In other embodiments the yeast cell has reduced activity of three or more of Hfd1, Hfd4, Pex10, Fao1 and GPAT, or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4, to Hfd4 as set forth in SEQ ID NO: 6, to Pex10 as set forth in SEQ ID NO: 8, to Fao1 as set forth in SEQ ID NO: 22 or to GPAT as set forth in SEQ ID NO: 10.

In one embodiment, the yeast cell expresses at least one heterologous desaturase as described above and at least one fatty acyl-CoA reductase as described above, and has reduced activity of Hfd1, Hfd4 and Pex10 or homologues thereof having at least 65% homology thereto.

In another embodiment, the yeast cell expresses at least one heterologous desaturase as described above and at least one fatty acyl-CoA reductase as described above, and has reduced activity of Hfd1, Hfd4 and Fao1 or homologues thereof having at least 65% homology thereto.

In another embodiment, the yeast cell expresses at least one heterologous desaturase as described above and at least one fatty acyl-CoA reductase as described above, and has reduced activity of Hfd1, Hfd4 and GPAT or homologues thereof having at least 65% homology thereto.

In another embodiment, the yeast cell expresses at least one heterologous desaturase as described above and at least one fatty acyl-CoA reductase as described above, and has reduced activity of Hfd1, Pex10 and Fao1 or homologues thereof having at least 65% homology thereto.

In another embodiment, the yeast cell expresses at least one heterologous desaturase as described above and at least one fatty acyl-CoA reductase as described above, and has reduced activity of Hfd1, Pex10 and GPAT or homologues thereof having at least 65% homology thereto.

In another embodiment, the yeast cell expresses at least one heterologous desaturase as described above and at least one fatty acyl-CoA reductase as described above, and has reduced activity of Hfd1, Fao1 and GPAT or homologues thereof having at least 65% homology thereto.

In another embodiment, the yeast cell expresses at least one heterologous desaturase as described above and at least one fatty acyl-CoA reductase as described above, and has reduced activity of Hfd4, Pex10 and Fao1 or homologues thereof having at least 65% homology thereto.

In another embodiment, the yeast cell expresses at least one heterologous desaturase as described above and at least one fatty acyl-CoA reductase as described above, and has reduced activity of Hfd4, Pex10 and GPAT or homologues thereof having at least 65% homology thereto.

In another embodiment, the yeast cell expresses at least one heterologous desaturase as described above and at least one fatty acyl-CoA reductase as described above, and has reduced activity of Hfd4, Fao1 and GPAT or homologues thereof having at least 65% homology thereto.

In another embodiment, the yeast cell expresses at least one heterologous desaturase as described above and at least one fatty acyl-CoA reductase as described above, and has reduced activity of Pex10, Fao1 and GPAT or homologues thereof having at least 65% homology thereto.

In other embodiments the yeast cell has reduced activity of four or more of Hfd1, Hfd4, Pex10, Fao1 and GPAT, or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4, to Hfd4 as set forth in SEQ ID NO: 6, to Pex10 as set forth in SEQ ID NO: 8, to Fao1 as set forth in SEQ ID NO: 22 or to GPAT as set forth in SEQ ID NO: 10.

In one embodiment, the yeast cell expresses at least one heterologous desaturase as described above and at least one fatty acyl-CoA reductase as described above, and has reduced activity of Hfd1, Hfd4, Pex10 and Fao1 or homologues thereof having at least 65% homology thereto.

In another embodiment, the yeast cell expresses at least one heterologous desaturase as described above and at least one fatty acyl-CoA reductase as described above, and has reduced activity of Hfd1, Hfd4, Pex10 and GPAT or homologues thereof having at least 65% homology thereto.

In another embodiment, the yeast cell expresses at least one heterologous desaturase as described above and at least one fatty acyl-CoA reductase as described above, and has reduced activity of Hfd1, Pex10, Fao1 and GPAT or homologues thereof having at least 65% homology thereto.

In another embodiment, the yeast cell expresses at least one heterologous desaturase as described above and at least one fatty acyl-CoA reductase as described above, and has reduced activity of Hfd1, Hfd4, Fao1 and GPAT or homologues thereof having at least 65% homology thereto.

In another embodiment, the yeast cell expresses at least one heterologous desaturase as described above and at least one fatty acyl-CoA reductase as described above, and has reduced activity of Hfd4, Pex10, Fao1 and GPAT or homologues thereof having at least 65% homology thereto.

In other embodiments the yeast cell has reduced activity of all of Hfd1, Hfd4, Pex10, Fao1 and GPAT, or homologues thereof having at least 65% homology thereto, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Hfd1 as set forth in SEQ ID NO:4, to Hfd4 as set forth in SEQ ID NO: 6, to Pex10 as set forth in SEQ ID NO: 8, to Fao1 as set forth in SEQ ID NO: 22 or to GPAT as set forth in SEQ ID NO: 10.

Acetyltransferase (EC 2.3.1.84)

The term "acetyltransferase" refers to enzymes of EC number 2.3.1.84 and can also be termed "alcohol-O-acetyltransferase" or "AcT". It acts on aliphatic alcohols, and catalyses the reaction:

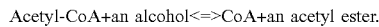
Acetyl-CoA+an alcohol<=>CoA+an acetyl ester.

The yeast cell of the present disclosure may express or overexpress an acetyltransferase. The acetyltransferase may be a native acetyltransferase which the cell to be modified is already capable of expressing, or it may be a heterologous acetyltransferase. If the yeast cell expresses a native acetyltransferase, the yeast cell is preferably modified so that expression of the native acetyltransferase is increased. This can be done by methods known in the art, such as but not limited to introduction of additional copies of the nucleic acid encoding the acetyltransferase in the genome or on a vector, modification of the promoter to a constitutive promoter with a high expression level, or to an inducible promoter which upon induction leads to high expression levels. A heterologous acetyltransferase may be expressed from a nucleic acid introduced in the cell, e.g. on a vector such as a plasmid, or by genomic integration. The nucleic acid may be codon-optimised for any purpose as is known in the art for the specific yeast cell used.

If the yeast cell does not express a native acetyltransferase, a nucleic acid encoding a heterologous acetyltransferase may be introduced in the cell, either in a genomic location or on a vector, to enable expression of the acetyltransferase. Preferably, the acetyltransferase is expressed at a high level, e.g. by introducing multiple copies of the nucleic acid encoding the acetyltransferase, or by taking advantage of a constitutive promoter with a high expression level, or of an inducible promoter which upon induction leads to high expression levels.

The term "overexpress" thus refers to the overexpression of an acetyltransferase in a yeast cell when compared to a yeast cell which has not been modified to overexpress the acetyltransferase, i.e. the parent strain.

In some embodiments, the acetyltransferase is the AcT of SEQ ID NO: 62 (Atf1, the S. cerevisiae AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 62.

In other embodiments, the conversion of at least part of the desaturated fatty alcohols to desaturated fatty acyl acetates is done chemically, as is known to the skilled person. For example, acetyl chloride can be added to the fatty alcohol and the mixture incubated at room temperature after mixing.

Production of Pheromone Compounds

The yeast cells of the present disclosure can be used for the production of compounds which are naturally comprised within pheromones, in particular *Lepidoptera* pheromones. Such compounds are typically not naturally produced by oleaginous yeast cells.

The pheromone compounds comprise desaturated and saturated fatty alcohols, desaturated and saturated fatty acyl acetates, and desaturated and saturated fatty aldehydes. Preferably, the compounds produced by the cells and methods of the present disclosure are desaturated.

The compounds obtainable by the present methods using the present cells may be naturally occurring pheromone compounds of a number of *Lepidoptera* species. The larvae of many lepidopteran species are major pests in agriculture. Some of the major pests include *Tortricidae*, *Noctuidae*, and *Pyralidae*. The larvae of the *Noctuidae* genus *Spodoptera* (armyworms), *Helicoverpa* (corn earworm), or *Pieris brassicae* can cause extensive damage to certain crops. *Helicoverpa zea* larvae (cotton bollworms or tomato fruitworms) are polyphagous, meaning they eat a variety of crops, including tomatoes and cotton.

In some embodiments, the compounds obtainable by the present methods using the present cells may be naturally occurring pheromone compounds of the *Tortricidae*, *Noctuidae*, and *Pyralidae* genera. For example, the compounds are naturally occurring in *Spodoptera* or *Helicoverpa*. In some embodiments, the compounds are naturally occurring in *Tuta absoluta* (tomato moth), *Lobesia botrana* (grapevine moth), *Ectomyelois ceratoniae* (carob moth) or *Epiphyas postvittana* (lightbrown apple moth).

Production of Desaturated Fatty Alcohols

The yeast cells of the present disclosure can be used for the production of desaturated fatty alcohols. Such compounds are naturally comprised within pheromones, in particular *Lepidoptera* pheromones, as detailed above.

The present oleaginous yeast cell expresses at least one heterologous desaturase capable of introducing at least one double bond in a fatty acyl-CoA; and at least one heterologous fatty acyl-CoA reductase, capable of converting at least part of said desaturated fatty acyl-CoA to a desaturated fatty alcohol; and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10). In specific embodiments, the yeast cell also has reduced or total loss of activity of Pex10 or of a protein having at least 60% homology to Pex10 (SEQ ID NO: 8), as described above.

Accordingly, herein is provided a method for producing a desaturated fatty alcohol in an oleaginous yeast cell, said method comprising the steps of providing a yeast cell and incubating said yeast cell in a medium, wherein the yeast cell:
  i) expresses at least one heterologous desaturase capable of introducing at least one double bond in a fatty acyl-CoA, thereby converting at least part of said fatty acyl-CoA to a desaturated fatty acyl-CoA; and
  ii) expresses at least one heterologous fatty acyl-CoA reductase, capable of converting at least part of said desaturated fatty acyl-CoA to a desaturated fatty alcohol, thereby producing said desaturated fatty alcohol; and
  iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8) and at least one of Hfd1, Hfd4, Fao1 or GPAT), as described above.

The yeast cell, the desaturase, the fatty acyl-CoA reductase, Hfd1, Hfd4, Pex10, Fao1 and GPAT or homologues thereof may be as defined herein elsewhere.

The fatty alcohols produced by such methods may be saturated or desaturated. Generally, desaturated fatty alcohols are most desirable, and it is an object of the present disclosure to provide methods for obtaining desaturated fatty alcohols and derivatives thereof with a high titre.

The yeast cell of the present disclosure may thus be used for the production of a range of desaturated fatty alcohols, such as:
  (Z)-Δ3 desaturated fatty alcohols having a carbon chain length of 8, 9, 10, 11, 12, 13, 14, 15, 16, 17, 18, 19, 20, 21 or 22;
  (E)-Δ3 desaturated fatty alcohols having a carbon chain length of 8, 9, 10, 11, 12, 13, 14, 15, 16, 17, 18, 19, 20, 21 or 22;
  (Z)-Δ5 desaturated fatty alcohols having a carbon chain length of 8, 9, 10, 11, 12, 13, 14, 15, 16, 17, 18, 19, 20, 21 or 22;
  (E)-Δ5 desaturated fatty alcohols having a carbon chain length of 8, 9, 10, 11, 12, 13, 14, 15, 16, 17, 18, 19, 20, 21 or 22;
  (Z)-Δ6 desaturated fatty alcohols having a carbon chain length of 8, 9, 10, 11, 12, 13, 14, 15, 16, 17, 18, 19, 20, 21 or 22;
  (E)-Δ6 desaturated fatty alcohols having a carbon chain length of 8, 9, 10, 11, 12, 13, 14, 15, 16, 17, 18, 19, 20, 21 or 22;
  (Z)-Δ7 desaturated fatty alcohols having a carbon chain length of 8, 9, 10, 11, 12, 13, 14, 15, 16, 17, 18, 19, 20, 21 or 22;
  (E)-Δ7 desaturated fatty alcohols having a carbon chain length of 8, 9, 10, 11, 12, 13, 14, 15, 16, 17, 18, 19, 20, 21 or 22;
  (Z)-Δ8 desaturated fatty alcohols having a carbon chain length of 9, 10, 11, 12, 13, 14, 15, 16, 17, 18, 19, 20, 21 or 22;
  (E)-Δ8 desaturated fatty alcohols having a carbon chain length of 9, 10, 11, 12, 13, 14, 15, 16, 17, 18, 19, 20, 21 or 22;
  (Z)-Δ9 desaturated fatty alcohols having a carbon chain length of 10, 11, 12, 13, 14, 15, 16, 17, 18, 19, 20, 21 or 22;
  (E)-Δ9 desaturated fatty alcohols having a carbon chain length of 10, 11, 12, 13, 14, 15, 16, 17, 18, 19, 20, 21 or 22;
  (Z)-Δ10 desaturated fatty alcohols having a carbon chain length of 11, 12, 13, 14, 15, 16, 17, 18, 19, 20, 21 or 22;
  (E)-Δ10 desaturated fatty alcohols having a carbon chain length of 11, 12, 13, 14, 15, 16, 17, 18, 19, 20, 21 or 22;
  (Z)-Δ11 desaturated fatty alcohols having a carbon chain length of 12, 13, 14, 15, 16, 17, 18, 19, 20, 21 or 22;
  (E)-Δ11 desaturated fatty alcohols having a carbon chain length of 12, 13, 14, 15, 16, 17, 18, 19, 20, 21 or 22;
  (Z)-Δ12 desaturated fatty alcohols having a carbon chain length of 13, 14, 15, 16, 17, 18, 19, 20, 21 or 22;
  (E)-Δ12 desaturated fatty alcohols having a carbon chain length of 13, 14, 15, 16, 17, 18, 19, 20, 21 or 22;
  (Z)-Δ13 desaturated fatty alcohols having a carbon chain length of 14, 15, 16, 17, 18, 19, 20, 21 or 22; and
  (E)-Δ13 desaturated fatty alcohols having a carbon chain length of 14, 15, 16, 17, 18, 19, 20, 21 or 22.

In one embodiment, the fatty alcohol has a chain length of 8. In another embodiment, the fatty alcohol has a chain length of 9. In another embodiment, the fatty alcohol has a chain length of 10. In another embodiment, the fatty alcohol has a chain length of 11. In another embodiment, the fatty alcohol has a chain length of 12. In another embodiment, the fatty alcohol has a chain length of 13. In another embodiment, the fatty alcohol has a chain length of 14. In another embodiment, the fatty alcohol has a chain length of 15. In another embodiment, the fatty alcohol has a chain length of 16. In another embodiment, the fatty alcohol has a chain length of 17. In another embodiment, the fatty alcohol has a chain length of 18. In another embodiment, the fatty alcohol has a chain length of 19. In another embodiment, the fatty alcohol has a chain length of 20. In another embodiment, the fatty alcohol has a chain length of 21. In another embodiment, the fatty alcohol has a chain length of 22.

The yeast cell disclosed herein may thus express a heterologous Δ9 desaturase and a fatty acyl-CoA reductase, and be used to produce fatty alcohols harbouring a desaturation in Z conformation at position 9, for example having a carbon chain length of 14 ((Z)9-14:OH). This fatty alcohol is a precursor of (Z)9-C14:OAc, which is an important component of pheromones derived from various species, for example the fall armyworm *Spodoptera frugiperda*.

In other embodiments, the yeast cell expresses a heterologous Δ11 desaturase and a fatty acyl-CoA reductase, and can be used to produce fatty alcohols harbouring a desaturation in Z conformation at position 9. For example, (Z)11-C14:OH may be produced, i.e. a fatty alcohol having a carbon chain length of 14 harbouring a desaturation in Z conformation at position 9. This fatty alcohol is a precursor of (Z)11-C14:OAc, which is an important component of pheromones derived from various species, for example the European corn borer *Ostrinia nubilalis* and the red-banded leafroller *Argyrotaenia velutinana*.

The yeast cell disclosed herein may thus express a heterologous Δ11 desaturase, a fatty acyl-CoA reductase, and acetyltransferase and be used to produce fatty alcohol acetates harbouring a desaturation in Z conformation at position 11, for example having a carbon chain length of 16 ((Z)11-16:OH). This fatty alcohol can be oxidized into (Z)11-16:Ald, which is an important component of pheromones derived from various species, for example the cotton bollworm *Helicoverpa armigera*.

In other embodiments, the yeast cell expresses a heterologous Δ11 desaturase and a fatty acyl-CoA reductase, and can be used to produce fatty alcohols harbouring a desaturation in E conformation at position 9. For example, (E)11-C14:OH may be produced, i.e. a fatty alcohol having a carbon chain length of 14 harbouring a desaturation in E conformation at position 9. This fatty alcohol is a precursor of (E)11-C14:OAc, which is an important component of pheromones derived from various species, for example the lightbrown apple moth *Epiphyas postvittana*.

The desaturated fatty alcohols produced by the present yeast cell may also be desaturated in more than one position. The desaturated fatty alcohols may be desaturated in at least two positions, such as at least three positions, such as four positions.

For example, (E)7, (Z)9 desaturated fatty alcohols may be produced having a carbon chain length of 10, 11, 12, 13, 14, 15, 16, 17, 18, 19, 20, 21 or 22. (E)3, (Z)8, (Z)11 desaturated fatty alcohols may be produced having a carbon chain length of 12, 13, 14, 15, 16, 17, 18, 19, 20, 21 or 22, for example 14. (Z)9, (E)11, (E)13 desaturated fatty alcohols may be produced having a carbon chain length of 14, 15, 16, 17, 18, 19, 20, 21 or 22.

The thus produced desaturated fatty alcohols may be further modified as is known in the art, for example by carbon chain shortening.

In some embodiments, (E)7, (Z)9 desaturated fatty alcohols may be produced having a carbon chain length of 10, 11, 12, 13, 14, 15, 16, 17, 18, 19, 20, 21 or 22. In other embodiments, (E)3, (Z)8, (Z)11 desaturated fatty alcohols may be produced having a carbon chain length of 12, 13, 14, 15, 16, 17, 18, 19, 20, 21 or 22. In yet another embodiment, (Z)9, (E)11, (E)13 desaturated fatty alcohols may be produced having a carbon chain length of 14, 15, 16, 17, 18, 19, 20, 21 or 22.

Production of a Desaturated Fatty Alcohol Acetate

Fatty alcohol acetates, in particular desaturated fatty alcohol acetates, are also naturally comprised within pheromones, in particular pheromones produced by species belonging to the Lepidoptera order. The yeast cells and methods of the present disclosure can also be used to obtain such fatty alcohol acetates.

This can be done by introducing a gene encoding an acetyltransferase, as detailed above, or it can be done by chemicals methods, as is known to the skilled person. For example, acetyl chloride can be added to the fatty alcohol and the mixture incubated at room temperature after mixing.

The yeast cell of the present disclosure may optionally express or overexpress an acetyltransferase capable of converting at least part of the desaturated fatty alcohols produced by the cell in desaturated fatty alcohol acetates, and may thus be used for the production of a range of desaturated fatty acetates having a carbon chain length of 8, 9, 10, 11, 12, 13, 14, 15, 16, 17, 18, 19, 20, 21 or 22, such as:

(Z)-Δ3 desaturated fatty alcohols having a carbon chain length of 8, 9, 10, 11, 12, 13, 14, 15, 16, 17, 18, 19, 20, 21 or 22;

(E)-Δ3 desaturated fatty alcohols having a carbon chain length of 8, 9, 10, 11, 12, 13, 14, 15, 16, 17, 18, 19, 20, 21 or 22;

(Z)-Δ5 desaturated fatty acetates having a carbon chain length of 8, 9, 10, 11, 12, 13, 14, 15, 16, 17, 18, 19, 20, 21 or 22;

(E)-Δ5 desaturated fatty acetates having a carbon chain length of 8, 9, 10, 11, 12, 13, 14, 15, 16, 17, 18, 19, 20, 21 or 22;

(Z)-Δ6 desaturated fatty acetates having a carbon chain length of 8, 9, 10, 11, 12, 13, 14, 15, 16, 17, 18, 19, 20, 21 or 22;

(E)-Δ6 desaturated fatty acetates having a carbon chain length of 8, 9, 10, 11, 12, 13, 14, 15, 16, 17, 18, 19, 20, 21 or 22;

(Z)-Δ7 desaturated fatty acetates having a carbon chain length of 8, 9, 10, 11, 12, 13, 14, 15, 16, 17, 18, 19, 20, 21 or 22;

(E)-Δ7 desaturated fatty acetates having a carbon chain length of 8, 9, 10, 11, 12, 13, 14, 15, 16, 17, 18, 19, 20, 21 or 22;

(Z)-Δ8 desaturated fatty acetates having a carbon chain length of 9, 10, 11, 12, 13, 14, 15, 16, 17, 18, 19, 20, 21 or 22;

(E)-Δ8 desaturated fatty acetates having a carbon chain length of 9, 10, 11, 12, 13, 14, 15, 16, 17, 18, 19, 20, 21 or 22;

(Z)-Δ9 desaturated fatty acetates having a carbon chain length of 10, 11, 12, 13, 14, 15, 16, 17, 18, 19, 20, 21 or 22;

(E)-Δ9 desaturated fatty acetates having a carbon chain length of 10, 11, 12, 13, 14, 15, 16, 17, 18, 19, 20, 21 or 22;

(Z)-Δ10 desaturated fatty acetates having a carbon chain length of 11, 12, 13, 14, 15, 16, 17, 18, 19, 20, 21 or 22;

(E)-Δ10 desaturated fatty acetates having a carbon chain length of 11, 12, 13, 14, 15, 16, 17, 18, 19, 20, 21 or 22;

(Z)-Δ11 desaturated fatty acetates having a carbon chain length of 12, 13, 14, 15, 16, 17, 18, 19, 20, 21 or 22;

(E)-Δ11 desaturated fatty acetates having a carbon chain length of 12, 13, 14, 15, 16, 17, 18, 19, 20, 21 or 22;

(Z)-Δ12 desaturated fatty acetates having a carbon chain length of 13, 14, 15, 16, 17, 18, 19, 20, 21 or 22;

(E)-Δ12 desaturated fatty acetates having a carbon chain length of 13, 14, 15, 16, 17, 18, 19, 20, 21 or 22;

(Z)-Δ13 desaturated fatty acetates having a carbon chain length of 14, 15, 16, 17, 18, 19, 20, 21 or 22; and (E)-Δ13 desaturated fatty acetates having a carbon chain length of 14, 15, 16, 17, 18, 19, 20, 21 or 22.

In one embodiment, the fatty alcohol acetate has a chain length of 8. In another embodiment, the fatty alcohol acetate has a chain length of 9. In another embodiment, the fatty alcohol acetate has a chain length of 10. In another embodiment, the fatty alcohol acetate has a chain length of 11. In another embodiment, the fatty alcohol acetate has a chain length of 12. In another embodiment, the fatty alcohol acetate has a chain length of 13. In another embodiment, the fatty alcohol acetate has a chain length of 14. In another embodiment, the fatty alcohol acetate has a chain length of 15. In another embodiment, the fatty alcohol acetate has a chain length of 16. In another embodiment, the fatty alcohol acetate has a chain length of 17. In another embodiment, the fatty alcohol acetate has a chain length of 18. In another embodiment, the fatty alcohol acetate has a chain length of 19. In another embodiment, the fatty alcohol acetate has a chain length of 20. In another embodiment, the fatty alcohol acetate has a chain length of 21. In another embodiment, the fatty alcohol acetate has a chain length of 22.

Accordingly, in one embodiment, the yeast cell expresses a heterologous Δ9 desaturase, a heterologous FAR and an acetyltransferase, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), and can be used to obtain (Z)9-C14:OAc, i.e. a fatty alcohol acetate having a carbon chain length of 14 harbouring a desaturation in Z conformation at position 9. This fatty alcohol acetate is an important component of pheromones derived from various species, for example the fall armyworm *Spodoptera frugiperda*. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In other embodiments, the yeast cell expresses a heterologous Δ11 desaturase, a heterologous FAR and an acetyltransferase, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), and can be used to produce (Z)11-C14:OAc, i.e. a fatty alcohol acetate having a carbon chain length of 14 harbouring a desaturation in Z conformation at position 9. This fatty alcohol acetate is an important component of pheromones derived from various species, for example the European corn borer *Ostrinia nubilalis* and the red-banded leafroller *Argyrotaenia velutinana*. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell expresses a heterologous Δ11 desaturase, a heterologous FAR, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), and can be used to obtain (Z)11-C16:OH. This fatty alcohol can be oxidized into (Z)11-C16:Ald, which is an important component of pheromones derived from various species, for example the cotton bollworm *Helicoverpa armigera*. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In other embodiments, the yeast cell expresses a heterologous Δ11 desaturase, a heterologous FAR and an acetyltransferase, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), and can be used to produce (E)11-C14:OAc, i.e. a fatty alcohol acetate having a carbon chain length of 14 harbouring a desaturation in E conformation at position 9. This fatty alcohol acetate is an important component of pheromones derived from various species, for example the lightbrown apple moth *Epiphyas postvittana*. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In other embodiments, the yeast cell expresses a heterologous Δ10 desaturase, a heterologous FAR and an acetyltransferase, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), and can be used to produce (Z)10-C14:OAc, i.e. a fatty alcohol acetate having a carbon chain length of 14 harbouring a desaturation in Z conformation at position 10. This compound can be shortened to obtain (Z)8-C12:OAc, which is an important component of pheromones derived from various species, for example the oriental fruit moth *Grapholita molesta*. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

The desaturated fatty acetates produced by the present yeast cell may also be desaturated in more than one position. The desaturated fatty acetates may be desaturated in at least two positions, such as at least three positions, such as four positions.

For example, (E)7, (Z)9 desaturated fatty acetates may be produced having a carbon chain length of 10, 11, 12, 13, 14, 15, 16, 17, 18, 19, 20, 21 or 22. (E)3, (Z)8, (Z)11 desaturated fatty acetates may be produced having a carbon chain length of 12, 13, 14, 15, 16, 17, 18, 19, 20, 21 or 22. (Z)9, (E)11, (E)13 desaturated fatty acetates may be produced having a carbon chain length of 14, 15, 16, 17, 18, 19, 20, 21 or 22.

The thus produced desaturated fatty acetates may be further modified as is known in the art, for example by carbon chain shortening. Thus, (E)7, (Z)9 desaturated fatty acetates may be produced having a carbon chain length of 12 starting from fatty acetates having a carbon chain length of 14, (E)3, (Z)8, (Z)11 desaturated fatty acetates may be produced having a carbon chain length of 12 starting from fatty acetates having a carbon chain length of 14, and (Z)9, (E)11, (E)13 desaturated fatty acetates may be produced having a carbon chain length of 12 starting from fatty acetates having a carbon chain length of 14.

In some embodiments, the yeast cell expresses a heterologous Δ9 desaturase, a Δ11 desaturase, a heterologous FAR and an acetyltransferase, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), and can be used to produce (E)9, (Z)11-C14:OAc, i.e. a fatty alcohol acetate having a carbon chain length of 14 harbouring a desaturation in E conformation at position 9 and a desaturation in Z conformation at position 11. This compound can be shortened to obtain (E)7, (Z)9:OAc, which is an important component of pheromones derived from various species, for example the grapevine moth *Lobesia botrana*. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

Production of a Desaturated Fatty Aldehyde

While the present disclosure provides methods for producing desaturated fatty alcohols and desaturated fatty alcohol acetates, it may be of interest to further convert said fatty alcohols to the corresponding aldehydes. Thus in some embodiments, the method may further comprise the step of converting at least part of the fatty alcohols to fatty aldehydes, thereby producing fatty aldehydes. This can be achieved by chemical methods or by further engineering of the yeast cell.

In some embodiments, the step of converting at least part of the fatty alcohols to the corresponding aldehydes is a step of chemical conversion. The chemical conversion is based on the oxidation of fatty alcohols to the corresponding aldehydes. Methods for performing this conversion are known in the art. Preferred methods are environmentally friendly and minimize the amount of hazardous waste. In some embodiments, the method comprises a Copper(I)/ABNO-catalysed aerobic alcohol oxidation reaction (Steves & Stahl, 2013).

Thus in some embodiments, the chemical conversion may be metal free, avoiding toxic heavy metal based reagents such as manganese oxides, chromium oxides (Jones ox. PDC, PCC) or ruthenium compounds (TPAP, Ley-Griffith ox.) In some embodiments, the conversion does not involve reactions with activated dimethyl sulfoxide such as the Swern oxidation or the Pfitzner-Moffat type. Such reactions may involve the stereotypic formation of traces of intensively smelling organic sulfur compounds such as dimethyl sulfide which can be difficult to remove from the target product.

In some embodiments, the method comprises a Dess-Martin reaction (Yadav et al., 2004, Meyer et al., 1994).

In other embodiments, the chemical conversion comprises the oxidation with sodium hypochlorite under aqueous/organic two phase conditions (Okada et al., 2014; Tamura et al., 2012; Li et al., 2009).

In some embodiments, the chemical oxidation can be performed with 1-chlorobenzotriazole in a medium of methylene chloride containing 25% pyridine (Ferrell and Yao, 1972).

Alternatively, the oxidation of a fatty alcohol to the corresponding fatty aldehyde can be performed enzymatically by alcohol dehydrogenases. The skilled person will know how to carry out enzymatic oxidation. For example, enzymatic oxidation can be carried out by contacting purified enzymes, cell extracts or whole cells, with the fatty alcohol.

The fatty alcohols obtainable by the cells and methods described herein can be further converted in fatty aldehydes by introducing a gene encoding an aldehyde-forming fatty acyl-CoA reductase EC 1.2.1.50 (FAR'). In this way, at least part of the desaturated fatty acyl-CoA can be converted to the corresponding fatty aldehyde by an aldehyde-forming fatty acyl-CoA reductase (FAR'). The enzymes capable of catalyzing this conversion can catalyse a reduction reaction, where the fatty acyl-CoA is reduced to a fatty aldehyde. Such enzymes are aldehyde-forming fatty acyl-CoA reductases, herein also referred to as FAR' or "aldehyde-forming FAR'", with an EC number 1.2.1.50. They catalyse the following reaction:

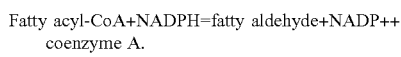
Fatty acyl-CoA+NADPH=fatty aldehyde+NADP++ coenzyme A.

In some embodiments, expression of the aldehyde-forming FAR' can be induced, for example if the genes encoding this enzyme is under the control of inducible promoters, as is known in the art. The yeast cell is incubated under suitable conditions, such as in an appropriate medium and at an appropriate temperature as is known to a person of skill in the art. Suitable media supporting yeast growth are known in the art and include, but are not limited to: undefined, complete media such as YEPD (or YPD, Yeast Extract Peptone Dextrose), defined, complete medium such as SC (Synthetic Complete), or defined, drop-out medium such as SD (Synthetic Dextrose) lacking one or more elements such as an amino acid or an inducer.

Thus, the following desaturated fatty aldehydes can be obtained:

(Z)-Δ3 desaturated fatty alcohols having a carbon chain length of 8, 9, 10, 11, 12, 13, 14, 15, 16, 17, 18, 19, 20, 21 or 22;

(E)-Δ3 desaturated fatty alcohols having a carbon chain length of 8, 9, 10, 11, 12, 13, 14, 15, 16, 17, 18, 19, 20, 21 or 22;

(Z)-Δ5 desaturated fatty aldehydes having a carbon chain length of 8, 9, 10, 11, 12, 13, 14, 15, 16, 17, 18, 19, 20, 21 or 22;

(E)-Δ5 desaturated fatty aldehydes having a carbon chain length of 8, 9, 10, 11, 12, 13, 14, 15, 16, 17, 18, 19, 20, 21 or 22;

(Z)-Δ6 desaturated fatty aldehydes having a carbon chain length of 8, 9, 10, 11, 12, 13, 14, 15, 16, 17, 18, 19, 20, 21 or 22;

(E)-Δ6 desaturated fatty aldehydes having a carbon chain length of 8, 9, 10, 11, 12, 13, 14, 15, 16, 17, 18, 19, 20, 21 or 22;

(Z)-Δ7 desaturated fatty aldehydes having a carbon chain length of 8, 9, 10, 11, 12, 13, 14, 15, 16, 17, 18, 19, 20, 21 or 22;

(E)-Δ7 desaturated fatty aldehydes having a carbon chain length of 8, 9, 10, 11, 12, 13, 14, 15, 16, 17, 18, 19, 20, 21 or 22;

(Z)-Δ8 desaturated fatty aldehydes having a carbon chain length of 9, 10, 11, 12, 13, 14, 15, 16, 17, 18, 19, 20, 21 or 22;

(E)-Δ8 desaturated fatty aldehydes having a carbon chain length of 9, 10, 11, 12, 13, 14, 15, 16, 17, 18, 19, 20, 21 or 22;

(Z)-Δ9 desaturated fatty aldehydes having a carbon chain length of 10, 11, 12, 13, 14, 15, 16, 17, 18, 19, 20, 21 or 22;

(E)-Δ9 desaturated fatty aldehydes having a carbon chain length of 10, 11, 12, 13, 14, 15, 16, 17, 18, 19, 20, 21 or 22;

(Z)-Δ10 desaturated fatty aldehydes having a carbon chain length of 11, 12, 13, 14, 15, 16, 17, 18, 19, 20, 21 or 22;
(E)-Δ10 desaturated fatty aldehydes having a carbon chain length of 11, 12, 13, 14, 15, 16, 17, 18, 19, 20, 21 or 22;
(Z)-Δ11 desaturated fatty aldehydes having a carbon chain length of 12, 13, 14, 15, 16, 17, 18, 19, 20, 21 or 22;
(E)-Δ11 desaturated fatty aldehydes having a carbon chain length of 12, 13, 14, 15, 16, 17, 18, 19, 20, 21 or 22;
(Z)-Δ12 desaturated fatty aldehydes having a carbon chain length of 13, 14, 15, 16, 17, 18, 19, 20, 21 or 22;
(E)-Δ12 desaturated fatty aldehydes having a carbon chain length of 13, 14, 15, 16, 17, 18, 19, 20, 21 or 22;
(Z)-Δ13 desaturated fatty aldehydes having a carbon chain length of 14, 15, 16, 17, 18, 19, 20, 21 or 22; and
(E)-Δ13 desaturated fatty aldehydes having a carbon chain length of 14, 15, 16, 17, 18, 19, 20, 21 or 22.

In one embodiment, the fatty acyl aldehyde has a chain length of 8. In another embodiment, the fatty acyl aldehyde has a chain length of 9. In another embodiment, the fatty acyl aldehyde has a chain length of 10. In another embodiment, the fatty acyl aldehyde has a chain length of 11. In another embodiment, the fatty acyl aldehyde has a chain length of 12. In another embodiment, the fatty acyl aldehyde has a chain length of 13. In another embodiment, the fatty acyl aldehyde has a chain length of 14. In another embodiment, the fatty acyl aldehyde has a chain length of 15. In another embodiment, the fatty acyl aldehyde has a chain length of 16. In another embodiment, the fatty acyl aldehyde has a chain length of 17. In another embodiment, the fatty acyl aldehyde has a chain length of 18. In another embodiment, the fatty acyl aldehyde has a chain length of 19. In another embodiment, the fatty acyl aldehyde has a chain length of 20. In another embodiment, the fatty acyl aldehyde has a chain length of 21. In another embodiment, the fatty acyl aldehyde has a chain length of 22.

The desaturated fatty aldehydes produced by the present yeast cell may also be desaturated in more than one position. The desaturated fatty aldehydes may be desaturated in at least two positions, such as at least three positions, such as four positions.

For example, (E)7, (Z)9 desaturated fatty aldehydes may be produced having a carbon chain length of 10, 11, 12, 13, 14, 15, 16, 17, 18, 19, 20, 21 or 22, such as 14. (E)3, (Z)8, (Z)11 desaturated fatty aldehydes may be produced having a carbon chain length of 14. (Z)9, (E)11, (E)13 desaturated fatty aldehydes may be produced having a carbon chain length of 14, 15, 16, 17, 18, 19, 20, 21 or 22, such as 14.

The thus produced desaturated fatty aldehydes may be further modified as is known in the art, for example by carbon chain shortening. Thus, (E)7, (Z)9 desaturated fatty aldehydes may be produced having a carbon chain length of 12 starting from fatty aldehydes having a carbon chain length of 14, (E)3, (Z)8, (Z)11 desaturated fatty aldehydes may be produced having a carbon chain length of 12 starting from fatty aldehydes having a carbon chain length of 14, and (Z)9, (E)11, (E)13 desaturated fatty aldehydes may be produced having a carbon chain length of 12 starting from fatty aldehydes having a carbon chain length of 14.

Fatty acyl-CoA

In order for the yeast cell to produce desaturated fatty alcohols and desaturated fatty alcohol acetates as described herein, the yeast cell needs fatty acyl-CoAs as a substrate. Preferably, the fatty acyl-CoA has a carbon chain length of 8, 9, 10, 11, 12, 13, 14, 15, 16, 17, 18, 19, 20, 21 or 22. In one embodiment, the fatty acyl-CoA has a carbon chain length of 8. In another embodiment, the fatty acyl-CoA has a carbon chain length of 9. In another embodiment, the fatty acyl-CoA has a carbon chain length of 10. In another embodiment, the fatty acyl-CoA has a carbon chain length of 11. In another embodiment, the fatty acyl-CoA has a carbon chain length of 12. In another embodiment, the fatty acyl-CoA has a carbon chain length of 13. In another embodiment, the fatty acyl-CoA has a carbon chain length of 14. In another embodiment, the fatty acyl-CoA has a carbon chain length of 15. In another embodiment, the fatty acyl-CoA has a carbon chain length of 16. In another embodiment, the fatty acyl-CoA has a carbon chain length of 17. In another embodiment, the fatty acyl-CoA has a carbon chain length of 18. In another embodiment, the fatty acyl-CoA has a carbon chain length of 19. In another embodiment, the fatty acyl-CoA has a carbon chain length of 20. In another embodiment, the fatty acyl-CoA has a carbon chain length of 21. In another embodiment, the fatty acyl-CoA has a carbon chain length of 22. In some embodiments a mixture of fatty acyl-CoAs having different carbon chain lengths is provided.

Such fatty acyl-CoAs can either be provided in the medium in which the yeast cell is incubated, or the yeast cell may be naturally able to produce such fatty acyl-CoA, or the yeast cell may be engineered in order to produce or to increase production of such fatty acyl-CoAs.

In some embodiments, the yeast cell is not naturally capable of producing a fatty acyl-CoA having a carbon chain length of 8, 9, 10, 11, 12, 13, 14, 15, 16, 17, 18, 19, 20, 21 or 22, or a mixture thereof. The yeast cell may in this case be engineered as is known in the art, for example by the introduction of a heterologous thioesterase. Thus in some embodiments, a nucleic acid encoding a thioesterase is introduced in the yeast cell, on a vector or by genomic integration. The thioesterase gene may be under the control of an inducible promoter, or under the control of a constitutive promoter. The nucleic acid encoding a thioesterase may be codon-optimised for any purpose for the yeast cell, as is known in the art. In particular, the nucleic acid may be codon-optimised for any purpose for a *Yarrowia* cell, such as a *Yarrowia lipolytica* cell.

In some embodiments, the thioesterase is derived from an organism selected from *Cuphea palustris, Cuphea hookeriana, Cinnamomum camphora*, or from *Escherichia coli*.

Yeast Cell

The present disclosure provides a yeast cell which has been modified to produce a desaturated fatty alcohol, and optionally a desaturated fatty alcohol acetate. Desaturated fatty alcohols and desaturated fatty alcohol acetates are components of pheromones, in particular of moth pheromones. The yeast cell disclosed herein thus provides a platform for environment-friendly moth pheromone production.

In some embodiments, the cell has been modified at the genomic level, e.g. by gene editing in the genome. The cell may also be modified by insertion of at least one nucleic acid construct such as at least one vector. The vector may be designed as is known to the skilled person to either enable integration of nucleic acid sequences in the genome, or to enable expression of a polypeptide encoded by a nucleic acid sequence comprised in the vector without genome integration.

In certain embodiments of the disclosure, yeast or fungi of genera including, but not limited to, *Blakeslea, Candida, Cryptococcus, Cunninghamella, Lipomyces, Mortierella,*

*Mucor, Phycomyces, Pythium, Rhodosporidium, Rhodotorula, Trichosporon*, and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutinis, R. gracilis, R. graminis, R. mucilaginosa, R. pinicola, Trichosporon pullans, T. cutaneum*, and *Yarrowia lipolytica* are used. In a preferred embodiment, the oleaginous yeast cell is a *Yarrowia lipolytica* cell.

The yeast cell to be modified, which will also be referred to as the host cell, may express native enzymes which are of the same class than the enzymes which are necessary for the production of desaturated fatty alcohols and desaturated fatty alcohol acetates. In some cases, however, such native enzymes may have a negative impact on the titre of desaturated fatty alcohols and/or desaturated fatty alcohol acetates which can be obtained; the native enzymes may thus be inactivated by methods known in the art, such as gene editing. For example, the genes encoding the native enzymes having a negative impact on the titre may be deleted or mutated so as to lead to total or partial loss of activity of the native enzyme.

The yeast cell of the present disclosure express at least one heterologous desaturase capable of introducing at least one double bond in a fatty acyl-CoA having a carbon chain length of 8, 9, 10, 11, 12, 13, 14, 15, 16, 17, 18, 19, 20, 21 or 22 as described herein, at least one heterologous fatty acyl-CoA reductase capable of converting at least part of said desaturated fatty acyl-CoA to a desaturated fatty alcohol as described herein, and optionally an acetyltransferase capable of converting at least part of said desaturated fatty alcohol to a desaturated fatty alcohol acetate, and has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10). In some embodiments, the yeast cell also expresses an acetyltransferase. In some embodiments, the yeast cell also expresses a thioesterase. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In one embodiment, the yeast cell:
i) expresses at least one heterologous desaturase capable of introducing at least one double bond in a fatty acyl-CoA, and is thereby capable of converting at least part of said fatty acyl-CoA to a desaturated fatty acyl-CoA; and
ii) expresses at least one heterologous fatty acyl-CoA reductase, capable of converting at least part of said desaturated fatty acyl-CoA to a desaturated fatty alcohol, thereby producing said desaturated fatty alcohol, and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In one embodiment, the yeast cell:
i) expresses at least one heterologous Δ3 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ5 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ6 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ7 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ8 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ9 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In a particular embodiment, the Δ9 desaturase has at least 60% homology to the Δ9 desaturase from *Drosophila melanogasteras* set forth in SEQ ID NO: 18.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ10 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ11 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In a particular embodiment, the desaturase has at least 60% homology to the Δ11 desaturase from *Amyelois transitella* as set forth in SEQ ID NO: 2. In another particular embodiment, the desaturase has at least 60% homology to the Δ11 desaturase from *Choristoneura rosaceana* as set forth in SEQ ID NO: 19. In another particular embodiment, the desaturase has at least 60% homology to the Δ11 desaturase from *Choristoneura parallela* as set forth in SEQ ID NO: 20.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ12 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ13 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In another embodiment, the yeast cell:
i) expresses at least one heterologous Δ14 desaturase capable of introducing at least one double bond in a fatty acyl-CoA; and
ii) expresses at least one heterologous fatty acyl-CoA reductase; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the FAR has at least 80% homology to the FAR from *Helicoverpa armigera* as set forth in SEQ ID NO: 14. In other embodiments, the FAR has at least 80% homology to the FAR from *Helicoverpa assulta* as set forth in SEQ ID NO: 16. In other embodiments, the FAR has at least 80% homology to the FAR from *Heliothis subflexa* as set forth in SEQ ID NO: 12. In other embodiments, the FAR has at least 80% homology to the FAR from *Bicyclus anynana* as set forth in SEQ ID NO: 24.

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

Nucleic Acids

It will be understood that throughout the present disclosure, the term 'nucleic acid encoding an activity' shall refer to a nucleic acid molecule capable of encoding a peptide, a protein or a fragment thereof having said activity. Such nucleic acid molecules may be open reading frames or genes or fragments thereof. The nucleic acid construct may also be a group of nucleic acid molecules, which together may encode several peptides, proteins or fragments thereof having an activity of interest. The term 'activity of interest' refers to one of the following activities: a desaturase as described herein, a fatty acyl-CoA reductase, an aldehyde-forming fatty acyl-CoA reductase, a thioesterase and/or an acetyltransferase activity. The nature of the one or more activity of interest will depend on the nature of the desired product one wishes to obtain with the present methods.

In some embodiments of the present methods, each of the nucleic acids encoding each of the present activities, i.e. a desaturase as described herein, a fatty acyl-CoA reductase, an aldehyde-forming fatty acyl coA reductase, a thioesterase and/or an acetyltransferase, may be comprised within the genome of the yeast cell or within a vector comprised within yeast cell.

In some embodiments, each of the nucleic acids encoding each of the present activities may be present in the genome of said yeast cell, either because the nucleic acid encodes a native protein, or because it has been integrated therein by genome engineering or genome editing or by crossing yeast cells of different mating types. Methods for integrating a nucleic acid are well known in the art. Thus in some embodiments the activity of interest is encoded by introduction of a heterologous nucleic acid in the yeast cell. The heterologous nucleic acid encoding said activity may be codon-optimised for any purpose, or may comprise features that can help improve the activity. For example, the heterologous nucleic acid may be modified so as to encode a modified protein. Such modifications include, but are not limited to, the introduction of localisation signals, gain-of-function or loss-of-function mutations, fusion of the protein to a marker or a tag such as fluorescent tag, insertion of an inducible promoter, introduction of modifications conferring increased stability and/or half-life.

The introduction of the heterologous nucleic acid encoding the activity of interest can be performed by methods known in the art. The skilled person will recognise that such methods include, but are not limited to: cloning and homologous recombination-based methods. Cloning methods may involve the design and construction of a plasmid in an organism such as *Escherichia coli*. The plasmid may be an integrative or a non-integrative vector. Cloning-free methods comprise homologous recombination-based methods such as adaptamer-mediated PCR or gap repair. Such methods often result in integration of the heterologous nucleic acid in the genome of the yeast cell.

The nucleic acids encoding the activities of interest may be present in high copy number.

Methods for Production of a Fatty Alcohol, a Fatty Alcohol Acetate or a Fatty Aldehyde The yeast cells of the present disclosure can be used for the production of a desaturated fatty alcohol and optionally derivatives thereof, such as a desaturated fatty alcohol acetate and/or a desaturated fatty aldehyde. Accordingly, also provided herein is a method of producing a fatty alcohol in an oleaginous yeast cell, said method comprising the steps of providing a yeast cell and incubating said yeast cell in a medium, wherein the yeast cell:
i) expresses at least one heterologous desaturase capable of introducing at least one double bond in a fatty acyl-CoA, thereby converting at least part of said fatty acyl-CoA to a desaturated fatty acyl-CoA; and
ii) expresses at least one heterologous fatty acyl-CoA reductase, capable of converting at least part of said desaturated fatty acyl-CoA to a desaturated fatty alcohol, thereby producing said desaturated fatty alcohol; and
iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), or having reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the yeast cell is capable of producing fatty alcohols with a total titre of at least 1 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L, wherein the total titre is the sum of the titre of desaturated fatty alcohols and the titre of saturated fatty alcohols.

In some embodiments, the yeast cell is capable of producing desaturated fatty alcohols with a titre of at least 1 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L.

In one embodiment, the present methods enable production of fatty alcohols, wherein the desaturated fatty alcohols produced by the cell represent at least 20% of the total fatty alcohols produced by the cell, such as at least 30%, such as at least 40%, such as at least 50%, such as at least 60%, such as at least 70%, such as at least 80%, such as at least 90% of the total fatty alcohols produced by the cell.

In a particular embodiment, the cell is capable of producing (Z)11-C16:OH with a titre of at least 0.5 mg/L, such as at least 1 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L (Z)11-C16:OH.

In another embodiment, the (Z)11-C16:OH produced by the cell represents at least 20% of the total fatty alcohols produced by the cell, such as at least 30%, such as at least 40%, such as at least 50%, such as at least 60%, such as at least 70%, such as at least 80%, such as at least 90% of the total fatty alcohols produced by the cell.

In yet another embodiment, the (Z)11-C16:OH produced by the cell represents at least 20% of the total desaturated fatty alcohols produced by the cell, such as at least 30%, such as at least 40%, such as at least 50%, such as at least 60%, such as at least 70%, such as at least 80%, such as at least 90% of the total desaturated fatty alcohols produced by the cell.

In preferred embodiments, the fatty alcohol is a fatty alcohol which is naturally found in pheromones produced by species of the Lepidoptera order.

The yeast cell may be as described herein. In some embodiments, the yeast cell is a *Yarrowia* cell, such as a *Yarrowia lipolytica* cell.

Recovery

It may be desirable to recover the products obtained by the methods disclosed herein. Thus the present methods may comprise a further step of recovering the desaturated fatty alcohol and/or the desaturated fatty alcohol acetate and/or desaturated fatty aldehyde produced by the present yeast cells.

In some embodiments, the method comprises a step of recovering the desaturated fatty alcohols. In a particular embodiment, the method comprises a step of recovering the desaturated fatty alcohols having a carbon chain length of 8, 9, 10, 11, 12, 13, 14, 15, 16, 17, 18, 19, 20, 21 or 22. In other embodiments, the method comprises a step of recovering the fatty alcohol acetates having a carbon chain length of 8, 9, 10, 11, 12, 13, 14, 15, 16, 17, 18, 19, 20, 21 or 22. In a particular embodiment, the method comprises a step of recovering the fatty alcohol acetates having a carbon chain length of 8, 9, 10, 11, 12, 13, 14, 15, 16, 17, 18, 19, 20, 21 or 22.

Methods for recovering the products obtained by the present invention are known in the art and may comprise an extraction with a hydrophobic solvent such as decane, hexane or a vegetable oil.

The recovered products may be modified further, for example desaturated fatty alcohols may be converted to the corresponding desaturated fatty aldehydes as described herein above.

The recovered products, i.e. the desaturated fatty alcohols and/or desaturated fatty alcohol acetates, may also be formulated into a pheromone composition. The composition may further comprise one or more additional compounds such as a liquid or solid carrier or substrate. Fatty aldehydes obtained from said desaturated fatty alcohols may also be comprised in such compositions.

Kit

Provided herein is a kit of parts for performing the present methods. The kit of parts may comprise an oleaginous yeast cell "ready to use" as described herein. In one embodiment, the yeast cell is a *Yarrowia* cell, such as a *Yarrowia lipolytica* cell.

In another embodiment, the kit of parts comprises a nucleic acid construct encoding the activities of interest to be introduced in the yeast cell. The kit of parts may comprise a nucleic acid construct for reducing activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10). The nucleic acid construct may be provided as a plurality of nucleic acid constructs, such as a plurality of vectors, wherein each vector encodes one or several of the desired activities, or wherein each vector allows reduction of the activity of one or more of Hfd1, Hfd4, Pex10, Fao1 and GPAT. In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

The kit of parts may optionally comprise the yeast cell to be modified. In some embodiments, the yeast cell to be modified already has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10). In specific embodiments, the yeast cell has reduced or total loss of activity of at least Pex10 or a protein having at least 60% homology to Pex10 (SEQ ID NO: 8 and at least one of Hfd1, Hfd4, Fao1 or GPAT), as described above.

In some embodiments, the kit of parts comprises all of the above.

Pheromone Composition

The present disclosure thus provides compounds, in particular desaturated fatty alcohols and fatty alcohol acetates, as well as derivatives thereof, and their use. In particular, the compounds obtainable using the present cells and methods are useful as components of pheromone compositions. Such pheromone compositions may be useful for integrated pest management. They can be used as is known in the art for e.g. mating disruption.

The desaturated fatty alcohols and desaturated fatty alcohol acetates obtainable by the present methods or using the present yeast cells may be formulated in a pheromone composition.

Such pheromone compositions may be used as integrated pest management products, which can be used in a method of monitoring the presence of pest or in a method of disrupting the mating of pest.

Pheromone compositions as disclosed herein may be used as biopesticides. Such compositions can be sprayed or dispensed on a culture, in a field or in an orchard. They can also, as is known in the art, be soaked e.g. onto a rubber septa, or mixed with other components. This can result in mating disruption, thereby preventing pest reproduction, or it can be used in combination with a trapping device to entrap the pests. Non-limiting examples of pests against which the present pheromone compositions can be used are: cotton bollworm (*Helicoverpa armigera*), striped stemborer (*Chilo suppressalis*), diamond back moth (*Plutella xylostella*), cabbage moth (*Mamestra brassicae*), large cabbage-heart caterpillar (*Crocidolomia binotalis*), European corn stalk borer (*Sesamia nonagrioides*), currant clearwing (*Synanthedon tipuliformis*) and artichoke plume moth (*Platyptilia carduidactyla*). Accordingly, use of the present compositions on a culture can lead to increased crop yield, with substantially no environmental impact.

The relative amounts of fatty alcohols and fatty alcohol acetates in the present pheromone compositions may vary depending on the nature of the crop and/or of the pest to be controlled; geographical variations may also exist. Determining the optimal relative amounts may thus require routine optimisation. The pheromone compositions may also comprise fatty aldehydes.

Examples of compositions used as repellents can be found in Kehat & Dunkelblum, 1993, for *H. armigera*, in Alfaro et al., 2009, for *C. suppressalis*, in Eizaguirre et al., 2002, for *S. nonagrioides*; in Wu et al., 2012, for *P. xylostella*; in Bari et al., 2003, for *P. carduidactyla*

In some embodiments, the pheromone composition may further comprise one or more additional compounds such as a liquid or solid carrier or substrate. For example, suitable carriers or substrate include vegetable oils, refined mineral oils or fractions thereof, rubbers, plastics, silica, diatomaceous earth, wax matrix and cellulose powder.

The pheromone composition may be formulated as is known in the art. For example, it may be in the form of a solution, a gel, a powder. The pheromone composition may be formulated so that it can be easily dispensed, as is known in the art.

EXAMPLES

Example 1: Construction of Plasmids

All BioBricks were amplified by PCR to obtain the DNA fragments for cloning into vectors and for gene knockouts. The primers are listed in Table 1 and the resulting DNA fragments are listed in Table 2. The PCR products were separated on a 1%-agarose gel containing Safe-Red® (iNtRON Biotechnology). PCR products of the correct size were excised from the gel and purified using the Nucleospin® Gel and PCR Clean-up kit (Macherey-Nagel).

TABLE 1

Primers.

| Primer name | Primer sequence, 5'->3' | SEQ ID NO: |
|---|---|---|
| PR-141 | agaacagcUgaagcttcgtacg | 25 |
| PR-142 | AGGCCACUAGTGGATCTGATATCAC | 26 |
| PR-10851 (Atrd11 expression cassette_fw) | agtgcaggUgacgcagtaggatgtcctgc | 27 |
| PR-10853 (Hs_ Far expression cassette_fw) | acctgcacUagagaccgggttgg | 28 |
| PR-10655 (EpiVecYL_fw) | acccattgcUgtagatatgtcttgtgtgtaagg | 29 |
| PR-10656 (EpiVecYL_rev) | atcatgtaaUtagttatgtcacgcttacattc | 30 |
| PR-10702 (Δpex10YL_up_fw) | cattgtaactagtcctggaggg | 31 |
| PR-10703 (Δpex10YL_up_rev) | acgaagttaUtttgagccgaggcagatttg | 32 |
| PR-10704 (Δpex10YL_down_fw) | acgaagttatUtgacgaggtctggatggaag | 33 |
| PR-10705 (Δpex10YL_down_rev) | cattgctaagaatccaaactggag | 34 |
| PR-10767 (NatMxSynYL-start_rev_new) | tcatggacatggcatagac | 35 |
| PR-11047 (NatMxSynYL-end_rev_new) | aataacttcgUatagcatacattatacgaagttatcgagcgtcccaaaacc | 36 |
| PR-11110 (*E.coli* backboneUSER_fw) | atcgcgtgcattcgcggccgcatttaaatcc | 37 |

TABLE 1-continued

Primers.

| Primer name | Primer sequence, 5'->3' | SEQ ID NO: |
|---|---|---|
| PR-11111 (E.coli backboneUSER_rev) | tcgcacgcattcgcggccgcaaatttaaataaaatg | 38 |
| PR-11138 (Hphsyn_fw) | agcaatgggUaaaaagcctgaactcaccgc | 39 |
| PR-11139 (Hphsyn_rev) | attacatgaUtattcctttgccctcggacg | 40 |
| PR-11694 (GPAT_up_USER_fw) | CGTGCGAUgcatctaggagctccattcagc | 41 |
| PR-11695 (GPAT_down_USER_rev) | CACGCGAUggacgagcagaccacg | 42 |
| PR-13494 (Nat-Tcyc-loxP_fw) | agggtacUactttggatgatactgc | 43 |
| PR-13549 (loxP-PrTefIntron_fw) | ataacttcgUataatgtatgctatacgaagttatagagaccggttggcggcgc | 44 |
| PR-14269 (UraYL_fw) | atgccctcctacgaggcccg | 45 |
| PR-14270 (UraYL_rev) | ctagcagttgatcttctggtag | 46 |
| PR-15426 (Δhfd1_up_fw) | CGTGCGAUataagaaaaaaaacag | 47 |
| PR-15427 (Δhfd1_up_rev) | AGCTGTTCUactaaccctacttcctc | 48 |
| PR-15428 (Δhfd1_down_fw) | AGTGGCCUttttattggtggtgtg | 49 |
| PR-15429 (Δhfd1_down_rev) | CACGCGAUgcatagtgcttttcatattc | 50 |
| PR-15438 (Δhfd4_up_fw) | CGTGCGAUagtatcgctactgtactaaaattg | 51 |
| PR-15439 (Δhfd4_up_rev) | AGCTGTTCUagcggacaagtgtcaatgtt | 52 |
| PR-15440 (Δhfd4_down_fw) | AGTGGCCUatgtattttatcagtagtatctc | 53 |
| PR-15441 (Δhfd4_down_rev) | CACGCGAUattggataatacatttccta | 54 |
| PR-16463 (Δfao1YL_up_fw) | CGTGCGAUTGGGGGAGGATTGCGATGGG | 55 |
| PR-16464 (Δfao1YL_up_rev) | AGCTGTTCUTGTCAAGTAATCAAGCTAATGC | 56 |
| PR-16465 (Δfao1YL_down_fw) | AGTGGCCUGCAAGAGACGAGTTTAGAAATAG | 57 |
| PR-16466 (Δfao1YL_down_rev) | CACGCGAUGTGTTAGTTCCTTGTAGTGTG | 58 |
| PR-16696 (GPAT_up_rev) | agctgttcUTACCGCACTTCCGGAACATC | 59 |
| PR-16698 (GPAT_100bpPr_down_fw) | agtggccUCCGATACTTGTTTGTGTGAC | 60 |
| PR-10714 | ttgcttgcgaacctaattcc | 71 |
| PR-10766 | ataacttcgUataatgtatgctatacgaagttataaggagtttggcgcccg | 72 |
| PR-10767 | tcatggacatggcatagac | 73 |
| PR-11047 | aataacttcgUatagcatacattatacgaagttatcgagcgtcccaaaacc | 74 |
| PR-13338 | ACCTGCACUgttgatgtgtgtttaattc | 75 |
| PR-141 | agaacagcUgaagcttcgtacg | 76 |
| PR-14148 | acgtgcaacgctUacgcaactaacatgaatg | 77 |
| PR-14149 | TGACTTCAACATTATATCGCTCTGA | 78 |
| PR-14279 | cgtgcgaUagagaccgggtt | 101 |
| PR-16618 | AGCCTGCGGUTAGTACTGCAAAAAGTGCTG | 102 |
| PR-142 | AGGCCACUAGTGGATCTGATATCAC | 79 |
| PR-14395 | cgtgcgaUttgatatggtgtaacaatg | 103 |
| PR-14396 | aagcgttgcacgUaagcactatcctctgctgcg | 104 |

TABLE 1-continued

Primers.

| Primer name | Primer sequence, 5'->3' | SEQ ID NO: |
|---|---|---|
| PR-14397 | agtggccUccgagcgtcgacaagcatac | 105 |
| PR-14398 | cacgcgaUgttagaagcaattggagaag | 106 |
| PR-14565 | agtggccUGGGGCTGGCGTGTGAAGGAG | 80 |
| PR-14566 | acgcgaUCAGACCTCTCACACGGCATC | 81 |
| PR-14567 | TAATACGACTCACTATAGGGC | 82 |
| PR-14568 | cacgcgaUCCTTGAGACGTTACCAGAGC | 83 |
| PR-14589 | cgtgcgaUGCGGAGGAGCAATAGACATACGATTTGAC | 84 |
| PR-14590 | aagcgttgcacgUTCCCCTCCCCACGGTG | 85 |
| PR-14591 | agtggccUCACCGAGGGATAGGGAACAC | 86 |
| PR-14592 | acgcgaUTTAACACTGGACCGTACTGC | 87 |
| PR-15430 | CGTGCGAUggttctatacgatgg | 88 |
| PR-15431 | AGCTGTTCUtatgatattttactaacc | 89 |
| PR-15432 | AGTGGCCUgattggcgttgtgttcaaatg | 90 |
| PR-15433 | CACGCGAUttgctcattcaccagaaaag | 91 |
| PR-15434 | CGTGCGAUatgtacaagtatttctattg | 92 |
| PR-15435 | AGCTGTTCUgaatgataaagagataacag | 93 |
| PR-15436 | AGTGGCCUtgtggcggaagttgtacacc | 94 |
| PR-15437 | CACGCGAUggacaacaggccgatagaac | 95 |
| PR-15521 | cgtgcgaUaaggagtttggcgcccgtt | 107 |
| PR-15522 | atgacagaUgctgtagatatgtcttgt | 108 |
| PR-15930 | acctgcggtUagtactgcaaaaagtgctgg | 96 |
| PR-16592 | AGTGCAGGUGCCACAATGGTGCCCAACAAGGGTTC | 97 |
| PR-16593 | CGTGCGAUCTATCGCTTTCGTCCCCAC | 98 |
| PR-16594 | aaccgcaggUGGTCCTGACCTCTAAG | 99 |
| PR-16595 | CACGCGAUCTACTCGTAGGACTTCTTCTC | 100 |
| PR-18486 | AGTGCAGGUGCCACAATGAACGAGATC | 109 |
| PR-18487 | CGTGCGAUTTAGGGGCCCAG | 110 |
| PR-18490 | ACCGCAGGCUCCCTACTCTCGAA | 111 |
| PR-18489 | CACGCGAUTTATCGAGACTTGTCC | 112 |
| PR-18499 | ATCTGTCAUGCCACAATGGCTCCCA | 113 |
| PR-18500 | CACGCGAUTTAGTCGTCCTTGGGG | 114 |

TABLE 2

DNA fragments obtained by PCR using the indicated template and primers.

| DNA fragment ID and name | Description | Fw_primer | Rv_primer | Template DNA |
|---|---|---|---|---|
| BB1135 | Vector backbone for propagation in E. coli | PR-11110 (E. coli backboneUSER_fw) | PR-11111 (E. coli backboneUSER_rev) | pCfB2196 (Stovicek et al., 2015) |
| BB01005 | Hygromycin resistance gene | PR-11138 (Hphsyn_fw) | PR-11139 (Hphsyn_rev) | Hygromycin resistance gene |
| BB1131 | Hs_FAR expression cassette | PR-10853 (Hs_Far expression cassette_fw) | PR-10655 (EpiVecYL_fw) | pCfB3465 |
| BB1132 | Part of pCfB3465 vector | PR-10656 (EpiVecYL_rev) | PR-10851 (Atrd11 expression cassette_fw) | pCfB3465 |
| BB1144 | Genomic region upstream of pex10 | PR-10702 (Δpex10YL_up_fw) | PR-10703 (Δpex10YL_up_rev) | Genomic DNA Yarrowia lipolytica GB20 |
| BB1145 | Genomic region downstream of pex10 | PR-10704 (Δpex10YL_down_fw) | PR-10705 (Δpex10YL_down_rev) | Genomic DNA Yarrowia lipolytica GB20 |
| BB1338 | Hygromycin resistance marker | PR-141 | PR-142 | Hygromycin resistance marker |
| BB1346 | Nourseothricin resistance marker | PR-141 | PR-142 | Nourseothricin resistance marker |
| BB1347 | 2/3 Start of nourseothricin resistance cassette | PR-13549 (loxP-PrTefIntron_fw) | PR-10767 (NatMxSynYL-start_rev_new) | BB1346 |
| BB1348 | 2/3 end of nourseothricin resistance cassette | PR-13494 (Nat-Tcyc-loxP_fw) | PR-11047 (NatMxSynYL-end_rev_new) | BB1346 |
| BB1349 | Genomic region upstream of pex10 fused to 2/3 Start of nourseothricin resistance cassette | PR-10702 (Δpex10YL_up_fw) | PR-10767 (NatMxSynYL-start_rev_new) | BB1144/BB1347 |
| BB1350 | Genomic region downstream of pex10 fused to 2/3 end of nourseothricin resistance cassette | PR-13494 (Nat-Tcyc-loxP_fw) | PR-10705 (Δpex10YL_down_rev) | BB1348/BB1145 |
| BB1427 | Ura3 marker cassette | PR-141 | PR-142 | Ura3 marker cassette |
| BB1543 | Genomic region upstream of hfd1 | PR-15426 (Δhfd1_up_fw) | PR-15427 (Δhfd1_up_rev) | Genomic DNA Yarrowia lipolytica GB20 |
| BB1544 | Genomic region downstream of hfd1 | PR-15428 (Δhfd1_down_fw) | PR-15429 (Δhfd1_down_rev) | Genomic DNA Yarrowia lipolytica GB20 |
| BB1549 | Genomic region upstream of hfd4 | PR-15438 (Δhfd4_up_fw) | PR-15439 (Δhfd4_up_rev) | Genomic DNA Yarrowia lipolytica GB20 |
| BB1550 | Genomic region downstream of hfd4 | PR-15440 (Δhfd4_down_fw) | PR-15441 (Δhfd4_down_rev) | Genomic DNA Yarrowia lipolytica GB20 |
| BB1725 | Genomic region upstream of fao1 | PR-16463 (Δfao1YL_up_fw) | PR-16464 (Δfao1YL_up_rev) | Genomic DNA Yarrowia lipolytica GB20 |
| BB1726 | Genomic region downstream of fao1 | PR-16465 (Δfao1YL_down_fw) | PR-16466 (Δfao1YL_down_rev) | Genomic DNA Yarrowia lipolytica GB20 |
| BB1757 | Genomic region upstream of fao1 fused to 2/3 start of Ura3 cassette | PR-16463 (Δfao1YL_up_fw) | PR-14270 (UraYL_rev) | BB1725/BB1427 |

TABLE 2-continued

DNA fragments obtained by PCR using the indicated template and primers.

Figure 2:
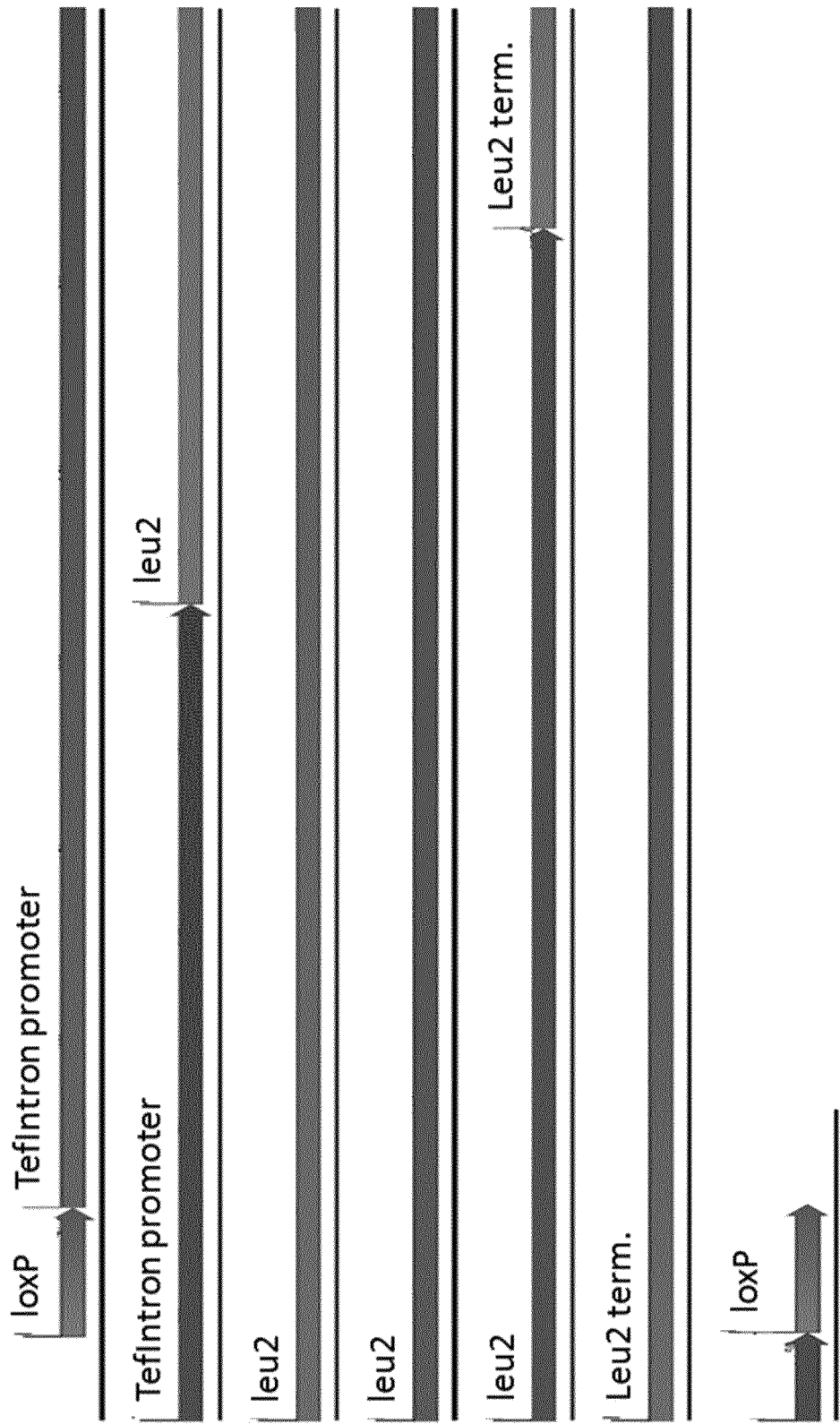
FIG. 2: map of B1963 (LEU2 selection marker cassette). Leu2 term.: Leu2 terminator.
Figure 3:
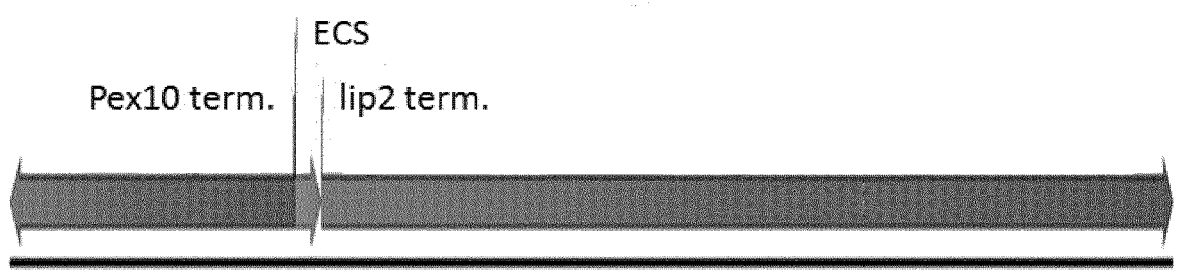
FIG. 3: map of BB1360 (pex10 and lip2 terminator). ECS: Easy Cloning Site. pex10 term.: pex10 terminator. lip2 term.: lip2 terminator.

| DNA fragment ID and name | Description | Fw_primer | Rv_primer | Template DNA |
|---|---|---|---|---|
| BB1758 | Genomic region downstream of fao1 fused to 2/3 end of Ura3 cassette | PR-14269 (UraYL_fw) | PR-16466 (Δfao1YL_down_rev), | BB1726/BB1427 |
| BB1782 | Genomic region upstream of pex10 | PR-11694 (GPAT_up_USER_fw) | PR-16696 (GPAT_up_rev) | Genomic DNA *Yarrowia lipolytica* GB20 |
| BB1784 | Genomic region downstream of pex10 | PR-16698 (GPAT_100bpPr_down_fw) | PR-11695 (GPAT_down_USER_rev) | Genomic DNA *Yarrowia lipolytica* GB20 |
| BB1014 | NatSyn | PR-10766 | PR-10767 | pCfB3405 |
| BB1144 | Genomic region upstream of pex10 | PR-10702 | PR-10703 | Genomic DNA *Yarrowia lipolytica* GB20 |
| BB1145 | Genomic region downstream of pex10 | PR-10704 | PR-10705 | Genomic DNA *Yarrowia lipolytica* GB20 |
| BB1351 | NatSyn | PR-10714 | PR-11047 | pCfB3405 |
| BB1352 | Pex10_up-NatSyn | PR-10702 | PR-10767 | BB1144/BB1014 |
| BB1353 | NatSyn-Pex10_down | PR-10714 | PR-10705 | BB1351/BB1145 |
| BB1360 | pex20 and lip2 terminator | PR-14148 | PR-14149 | FIG. 3 |
| BB1439 | Genomic region upstream of intergenic region IntE_1 | PR-14395 | PR-14397 | Genomic DNA *Yarrowia lipolytica* GB20 |
| BB1440 | Genomic region downstream of intergenic region IntE_1 | PR-14397 | PR-14398 | Genomic DNA *Yarrowia lipolytica* GB20 |
| BB1471 | Genomic region upstream of intergenic region IntC_1 | PR-14565 | PR-14566 | Genomic DNA *Yarrowia lipolytica* GB20 |
| BB1472 | Genomic region downstream of intergenic region IntC_1 | PR-14567 | PR-14568 | Genomic DNA *Yarrowia lipolytica* GB20 |
| BB1483 | Genomic region upstream of intergenic region IntE_4 | PR-14589 | PR-14590 | Genomic DNA *Yarrowia lipolytica* GB20 |
| BB1484 | Genomic region downstream of intergenic region IntE_4 | PR-14591 | PR-14592 | Genomic DNA *Yarrowia lipolytica* GB20 |
| BB1558 | EXP promoter | PR-15521 | PR-15522 | Genomic DNA *Yarrowia lipolytica* GB20 |
| BB1687 | GPD promoter fused to Tefintron promoter | PR-13338 | PR-15930 | pCfB3465 |
| BB1739 | Δ11 desaturase A. segetum | PR-16592 | PR-16593 | Seq ID NO: 67 |
| BB1740 | FAR H. armigera | PR-16594 | PR-16595 | Seq ID NO: 14 |
| BB1741 | Tefintron promoter | PR-14279 | PR-16618 | Genomic DNA *Yarrowia lipolytica* GB20 |
| BB1963 | Leu2 selection marker cassette | PR-141 | PR-142 | FIG. 2 |
| BB2601 | SliDes11 | PR-18499 | PR-18500 | SEQ ID NO: 65 |
| BB2602 | Dmd9 | PR-18490 | PR-18489 | SEQ ID NO: 63 |
| BB2603 | ScAft1 | PR-18486 | PR-18487 | SEQ ID NO: 62 |

The BioBrick BB1135 was treated with the nicking endonuclease Nb.BsmI (New England Biolabs) according to the manufactures instructions and purified using Nucleospin® Gel and PCR Clean-up kit (Macherey-Nagel) prior to use. The DNA fragments were assembled by USER-cloning via the following protocol: 1-1.3 μl of each BioBrick (listed in Table 3), 0.5 µl CutSmart® (New England BioLabs), and 0.5 µl USER enzyme (New England Biolabs) were mixed and incubated at 37° C. for 25 min and at 25° C. for 25 min. The reaction was transformed into chemically competent *E. coli* DHalpha cells and the cells were plated on Lysogeny Broth (LE) agar plates with 100 mg/L ampicillin. The plates were incubated overnight at 37° C. and the resulting colonies were screened by colony PCR. The plasmids were purified from overnight *E. coli* cultures and the correct cloning was confirmed by sequencing. The constructed vectors are listed in Table 3.

The parent plasmids pCfB4778, pCfB5219 and pCfB4781 were digested as described in Jensen et al., 2014 before assembly by USER-cloning. The DNA fragments were assembled by USER-cloning via the following protocol: 1-1.3 µl of each BioBrick (listed in Table 8), 0.5 µl Cut-Smart® (New England BioLabs), and 0.5 µl USER enzyme (New England Biolabs) were mixed and incubated at 37° C. for 25 min and at 25° C. for 25 min. The reaction was transformed into chemically competent *E. coli* DHalpha cells and the cells were plated on Lysogeny Broth (LB) agar plates with 100 mg/L ampicillin. The plates were incubated overnight at 37° C. and the resulting colonies were screened by colony PCR. The plasmids were purified from overnight *E. coli* cultures and the correct cloning was confirmed by sequencing. The constructed vectors are listed in Table 3.

TABLE 3

Vectors.

| Vector name | Selection marker | DNA fragments assembled |
|---|---|---|
| pCfB3465 | Ura3 | |
| pCfB5110 | NatSyn | BB1135, BB1346, BB1543, BB1544 |
| pCfB5113 | HphSyn | BB1135, BB1338, BB1549, BB1550 |
| pCfB3516 | HphSyn | BB01005, BB1131, BB1132 |
| pCfB5573 | HphSyn | BB1135, BB1338, BB1757, BB1758 |
| pCfB5750 | Ura3 | BB1135, BB1427, BB1782, BB1784 |
| pCfB4158 | Leu2 | |
| pCfB4781 | NatSyn | BB1135, BB1360, BB1346, BB1471, BB1472 |
| pCfB4778 | Ura3 | BB1135, BB1360, BB1439, BB1440, BB1427 |
| pCfB5219 | HphSyn | BB1135, BB1360, BB1338, BB1483, BB1484 |
| pCfB5574 | NatSyn | BB1135, BB1346, BB1725, BB1726 |
| pCfB5929 | HphSyn | pCfB5219, BB1687, BB1739, BB1740 |
| pCfB5930 | NatSyn | pCfB4781, BB1687, BB1739, BB1740 |
| pCfB6397 | Leu2 | BB1135, BB1963, BB1782, BB1784 |
| pCfB7235 | Ura3 | pCfB4778, BB2603, BB1687, BB1740 |
| pCfB7239 | HphSyn | pCfB5219, BB2602, BB1741 |
| pCfB7240 | HphSyn | pCfB5219, BB1558, BB2601 |
| pCfB7681 | HphSyn | BB1135, BB1338, BB1782, BB1784 |
| pCfB7681 | HphSyn | BB1135, BB1338, BB1782, BB1784 |
| pCfB7682 | Ura3 | BB1135, BB1427, BB1725, BB1726 |
| pCfB7725 | NatSyn | BB1135, BB1346, BB1782, BB1784 |
| pCfB7869 | NatSyn | BB1135, BB1346, BB1549, BB1550 |

Example 2: Construction of Strains

The constructed strains are listed in Tables 4 and 5. Prior to transformation into *Y. lipolytica*, the expression plasmids were linearised with NotI. The linearised plasmid or Bio-Bricks were transformed into *Y. lipolytica* GB 20 (Angerer, 2014) using a lithium-acetate-based protocol (Chen, 1997). After transformation the cells were recovered in 500 µl YPD medium for 2 hours at 30° C. Positive transformants were selected on synthetic complete (SC) medium (Sigma-Aldrich) lacking either uracil or leucine or on YPD medium containing hygromycin (50 mg/L) or nourseothricin (250 mg/L). The integration of the knockout constructs into the *Y. lipolytica* genome was confirmed by colony PCR.

The Ura3, NatSyn, HphSyn marker cassettes, which were flanked by loxP sites, were removed from strain ST5255 using a Cre recombinase-based system like following. Strain 5255 was transformed with the vector pCfB4158, expressing the Cre recombinase using a lithium-acetate-based protocol (Chen, 1997). After transformation, the cells were recovered in 500 µl YPD medium for 2 hours at 30° C. and plated on SC medium without leucine. Colonies were screened for successful marker removal by replica plating on SC medium without uracil and YPD supplemented with either hygromycin or nourseothricin. No cell growth on these plates indicated successful marker removal.

Strain ST6527 expresses Atrd11 and HarFAR from an intergenic region on chromosome C. The gene expression cassettes are the same as in to pCfB5929. Additionally, the open-reading frame of genes HFD4 (YALI0B01298g) and HFD1 (YAL10F23793g), as well as nucleotides −1130 to −100 upstream of the coding sequence of GPAT (YALI0C000209g) were deleted. A premature Stop-codon and frame-shift were introduced into open reading frames of PEX10 (YALI0C001023g) and FAO1 ((YALI0B14014g) resulting in non-functional genes.

Figure 4:
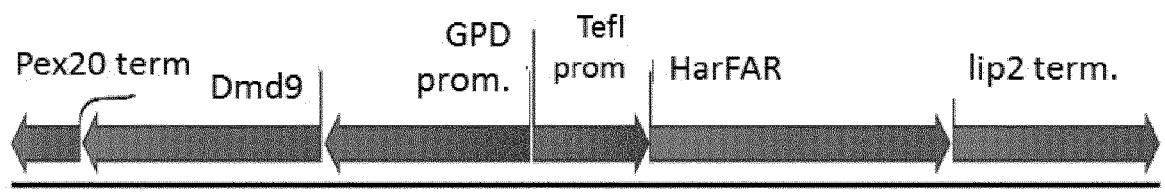
FIG. 4: map of expression cassette of Dmd9 and HarFAR. pex20 term: pex20 terminator. TefI prom.: Tefintron promoter. lip2 term.; lip2 terminator.

Strain ST7394 expresses Dmd9, HarFAR and Atf1 as described in pCfB6969 and pCfB7600 from intergenic regions on chromosomes C and D (FIG. 4). Additionally, the open-reading frame of genes HFD4, HFD2, HFD3 and HFD1, as well as nucleotides −1130 to −100 upstream of the coding sequence of GPAT (YALI0000209g) were deleted. A premature Stop-codon and frame-shift was introduced into PEX10 and FAO1 resulting in non-functional genes.

TABLE 4

Strains. Atrd11 = Δ11 desaturase from *Amyelois transitella*; HsFAR = fatty acyl-CoA reductase from *Heliothis subflexa*

| Strain name | Strain description | Parent strain | Plasmids/ BioBricks |
|---|---|---|---|
| ST3683 | *Yarrowia lipolytica* GB20 | — | — |
| ST3737 | Δpex10 | ST3683 | BB1352/ BB1353 |
| ST3842 | Δpex10 Atrd11 Hs_FAR | ST3737 | pCfB3516 |
| ST3844 | Atrd11 Hs_FAR | ST3683 | pCfB3465 |
| ST5107 | Atrd11 Hs_FAR Δhfd1 | ST3844 | pCfB5110 |
| ST5110 | Atrd11 Hs_FAR Δhfd4 | ST3844 | pCfB5113 |
| ST5255 | Atrd11 Hs_FAR Δhfd1 Δhfd4 | ST5107 | pCfB5113 |
| ST5791 | Atrd11 Hs_FAR Δhfd1 Δhfd4 Δpex10 Δfao1 GPAT_100bpPr | ST5789 | pCfB5750 |
| ST6277 | Atrd11 Hs_FAR Δhfd1 Δhfd4 Δpex10 Δfao1 GPAT_100bpPr | ST5789 | pCfB6397 |
| ST6289 | Atrd11 Hs_FAR Δhfd1 Δhfd4 Δpex10 Δfao1 GPAT_100bpPr Atrd11 HarFAR | ST6277 | pCfB5929 |
| ST6360 | Δhfd4 Δhfd1 Δpex10 Δfao1 Atrd11 Des11 HsFAR HarFAR Atf1 | ST5789 | pCfB7235 pCfB7240 |
| ST6379 | Atrd11 Hs_FAR Δhfd1 Δhfd4 Δpex10 Δfao1 GPAT_100bpPr Atrd11 HarFAR Atrd11 HarFAR | ST6289 | pCfB5930 |
| ST7458 | Atrd11 HsFAR 100bp_PrGPAT | ST3844 | pCfB7681 |
| ST7509 | Δpex10 Atrd11 HsFAR Δfao1 | ST3842 | pCfB7682 |

TABLE 4-continued

Strains. Atrd11 = Δ11 desaturase from *Amyelois transitella*;
HsFAR = fatty acyl-CoA reductase from *Heliothis subflexa*

| Strain name | Strain description | Parent strain | Plasmids/ BioBricks |
|---|---|---|---|
| ST7510 | Atrd11 HsFAR Δhfd1 100bp_PrGPAT | ST5107 | pCfB7681 |
| ST7511 | Atrd11 HsFAR Δhfd4 100bp_PrGPAT | ST5110 | pCfB7725 |
| ST7514 | Δpex10 Atrd11 HsFAR 100bp_PrGPAT | ST3842 | pCfB5750 |
| ST7787 | Atrd11 HsFAR Δfao1 | ST3844 | pCfB5573 |
| ST7929 | Atrd11 HsFAR Δfao1 Δhfd4 | ST7787 | pCfB7869 |

TABLE 5

Strains and fatty alcohol production

| Strain name | Strain description | Parent strain | Plasmids/ BioBricks integrated | Z11-C16:OH [mg/L] | Total fatty alcohols [mg/L] | Percent Z11-C16:OH of total fatty alcohols |
|---|---|---|---|---|---|---|
| *Yarrowia lipolytica* GB20 | Negative control | N/A | N/A | 0 ± 0 | 0 ± 0 | 0 ± 0 |
| ST3844 | Atrd11 Hs_FAR | *Yarrowia lipolytica* GB20 | pCfB3465 | 0.78 ± 0.07 | 1.25 ± 0.11 | 62 ± 2 |
| ST5107 | Atrd11 Hs_FAR Δhfd1 | ST3844 | pCfB5110 | 2.39 ± 0.5 | 3.93 ± 0.96 | 61 ± 5 |
| ST5110 | Atrd11 Hs_FAR Δhfd4 | ST3844 | pCfB5113 | 1.54 ± 0.70 | 2.31 ± 0.93 | 65 ± 6 |
| ST3842 | Atrd11 Hs_FAR Δpex10 | ST3737 | pCfB3516 | 1.38 ± 0.36 | 6.04 ± 2.62 | 24 ± 4 |
| ST5255 | Atrd11 Hs_FAR Δhfd1 Δhfd4 | ST5107 | pCfB5113 | 3.46 ± 0.96 | 7.61 ± 2.13 | 45 ± 0 |
| ST5452 | Atrd11 Hs_FAR Δhfd1 Δhfd4 Δpex10 | ST5450 | BB1349/ BB1350 | 4.79 ± 0.47 | 11.40 ± 0.91 | 42 ± 4 |
| ST5789 | Atrd11 Hs_FAR Δhfd1 Δhfd4 Δpex10 Δfao1 | ST5452 | pCfB5573 | 14.93 ± 3.60 | 64.46 ± 6.29 | 23 ± 4 |
| ST5791 | Atrd11 Hs_FAR Δhfd1 Δhfd4 Δpex10 Δfao1 ΔPrGPAT | ST5789 | pCfB5750 | 26.20 ± 8.85 | 57.37 ± 19.5 | 46 ± 1 |

Example 3: Production of Fatty Alcohols by Yeast

One individual clone of each strain was inoculated into 5 ml YPD medium with 8% glucose (10 g/L yeast extract, 20 g/L peptone, 80 g/L dextrose) in 12-ml glass tubes (Duran, Wertheim, Germany) with metal labocap lids (Lüdiswiss, Flawil, Switzerland) and incubated overnight at 30° C. with shaking at 250 rpm. The following day the overnight culture was centrifuged, the supernatant was discarded and the pellet was resuspended in 2 ml nitrogen-limited medium (2.9 g/L (NH4)2SO4, 1.7 g/L YNB (without amino acids and ammonium sulfate), 240 mg/L leucine, 76 mg/L lysine, 20 mg/L uracil and 60 g/L glucose). The cultures were incubated for 48 hours at 30° C. and shaken at 250 rpm.

For extraction, 1 mL of culture was transferred into a 4-mL glass vial and 10 μL of internal standard stock (1 μg/μL (Z)-10-heptan-1-yl methyl ester in 100% ethanol) was added. The vials were covered with small pieces of aluminum foil and we used a needle to pierce small holes in the foil covers. The samples were vortexed and placed at −80° C. for storage until analysis. The samples were freeze-dried in a freeze dry system (Freezone6 and Stoppening tray dryer, Labconco, Kansas City, USA) at −40° C., then 1 mL chloroform:methanol 2:1 was added to disrupt the cells. The mix was vortexed for 45 s and left at room temperature for 4 hours. The organic solvents were evaporated slowly under a nitrogen stream. 1 ml of hexane was added, the samples were vortexed for 10 s, centrifuged and 200 μl were transferred to a new glass vial.

GC-MS analyses were performed on a Hewlett Packard 6890 GC coupled to a mass selective detector HP 5973. The GC was equipped with an INNOWax column (30 m×0.25 mm×0.25 μm), and helium was used as carrier gas (average velocity: 33 cm/s). The MS was operated in electron impact mode (70 eV), scanning between m/z 30 and 400, and the injector was configured in splitless mode at 220° C. The oven temperature was set to 80° C. for 1 min, then increased at a rate of 10° C./min to 210° C., followed by a hold at 210° C. for 15 min, and then increased at a rate of 10 C/min to 230° C. followed by a hold at 230° C. for 20 min. Compounds were identified by comparison of retention times and mass spectra with those of reference compounds available in laboratory collection. Compounds were quantified by the Total Ion Current (TIC) recorded. Data were analyzed by the Agilent ChemStation software and iWork Numbers. The concentrations of fatty alcohols were calculated based on internal standard (Table 4).

Deletion of genes potentially implicated in fatty alcohol degradation (HFD1, HFD4, FAO1, PEX10), improved the production of total fatty alcohols, but decreased the ratio of desaturated alcohol to the total fatty alcohols (Table 5). Decreasing the expression of the gene encoding for glycerol-3-phosphate acyltransferase (GPAT), which catalyzes the first reaction towards glycerolipids biosynthesis, increased the production of desaturated alcohol, increasing the ratio of desaturated alcohol (Z11-16:01-1) to the total alcohols from 23 to 46%. At the same time, the concentration of lipids and free fatty acids (measured as total fatty acid methyl esters) decreased from 1.8 to 0.9 g/L.

Figure 6:
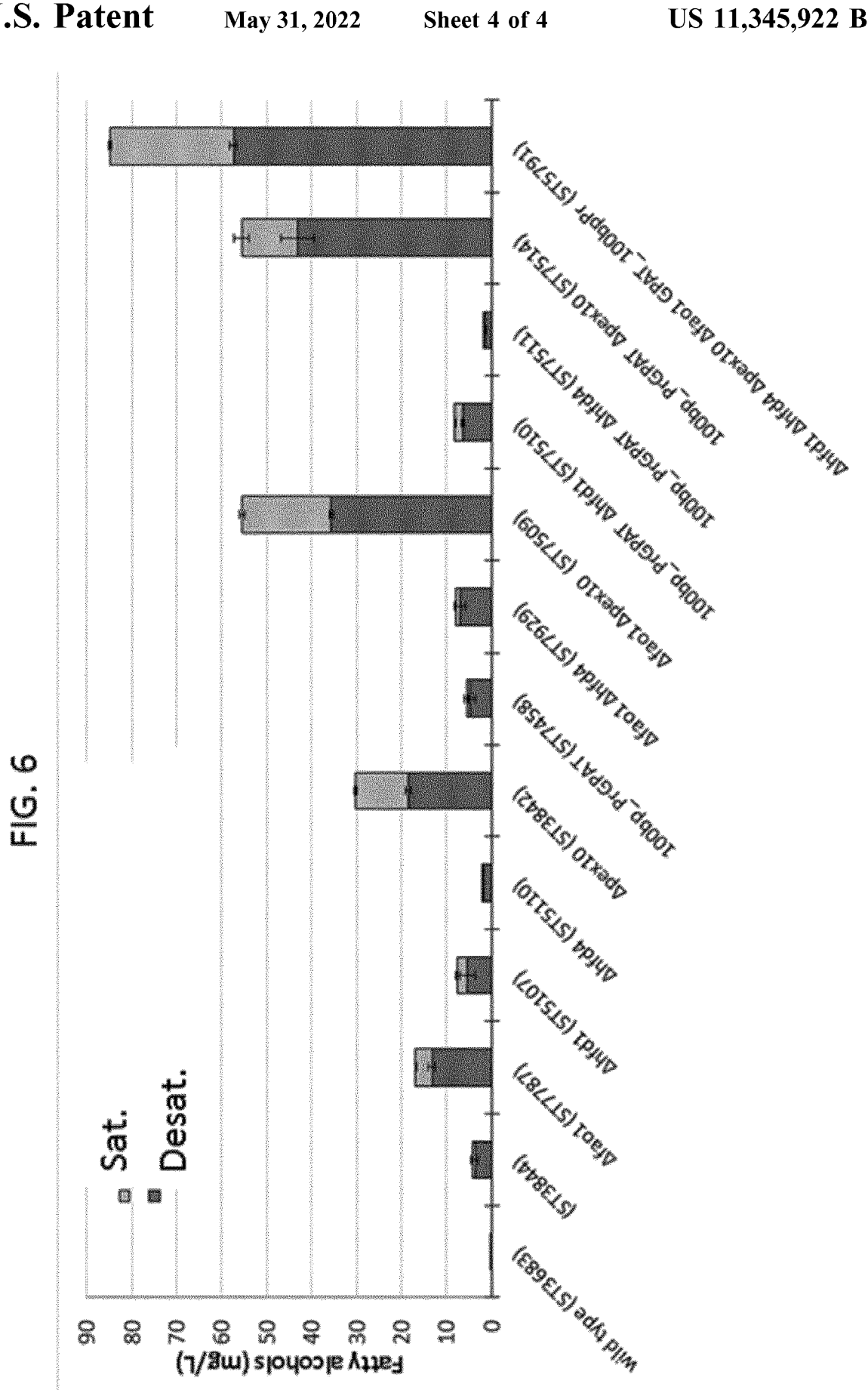
FIG. 6: production of fatty alcohols in various *Y. lipolytica* strains; beyond the genotype indicated on the X axis, the strains also all express the *Amyelois transitella* Δ11 desaturase and the *Heliothis subflexa* reductase (Hs_FAR). Sat.: saturated fatty alcohols (15:OH and 16:OH). Desat.: desaturated fatty alcohols ((Z)9-16:OH and (Z)11-16:OH).

Strains from Table 4 were inoculated into 3 mL mineral medium to an optical density (600 nm) of 1 in 24-deep well plates (EnzyScreen, NL). The composition of the mineral medium was as in Jensen et al, 2014, but glucose was replaced by 70 g/L glycerol. The medium was supplemented with 760 mg/L lysine, 760 mg/L leucine and 200 mg/L uracil. The cultures were incubated for 67 hours at 30° C. shaken at 250 rpm. For fatty alcohol extraction, 1 mL of culture was transferred into a 4-mL glass vial and 10 µL of internal standard solution (2 µg/µL (Z)-10-heptan-1-yl methyl ester in 100% ethanol) was added. The vials were covered with small pieces of aluminum foil and a needle was used to pierce small holes in the foil covers. The samples were vortexed and placed at −80° C. for storage until analysis. The samples were freeze-dried in a freeze dry system (Freezone6 and Stoppening tray dryer, Labconco, Kansas City, USA) at −40° C., then 1 mL chloroform:methanol 2:1 was added to disrupt the cells. The mix was vortexed for 45 s and left at room temperature for 4 hours. The organic solvents were evaporated slowly under a nitrogen stream. 1 ml of hexane was added, the samples were vortexed for 10 s, centrifuged and 200 µl were transferred to a new glass vial. Quantification was performed with a SCION TQ GC-MS (Bruker), equipped with an INNOWax 30 m×0.25 mm×0.25 µm column, with helium as carrier gas. The injector was configured in splitless mode at 250° C., the oven temperature was set to 80° C. for 1 min, then increased at a rate of 10° C./min to 210° C., followed by a hold at 210° C. for 10 min, and then increased at a rate of 10 C/min to 230° C. followed by a hold at 230° C. for 5 min. The MS was operated in electron impact mode (70 eV), scanning between m/z 30 and 350. Compounds were identified by comparison of retention times and mass spectra with those of reference compounds. Compounds were quantified by the Total Ion Current (TIC) recorded. Data were analyzed by the BrukerMSWorkstation software. The concentrations of fatty alcohols were calculated based on internal standards (FIG. 6).

All strains expressing the Δ11 desaturase from Δ11 desaturase from *Amyelois transitella* (Atrd11) and the fatty acyl-CoA reductase from *Heliothis subflexa* (HsFAR) produced (Z)11-16:OH. When studying the single gene knock-outs, the most prominent effects were observed for FAO1 and PEX10 knock-outs (265 and 406% improvement in desaturated fatty alcohols). Double deletions were much more effective, e.g, knocking out both FAO1 and PEX10 gave 877% increase in desaturated fatty alcohol titer, while the combination of GPAT downregulation and PEX10 knock-out gave a 1083% increase. Combining several of the successful treatments led to 1475% increase in the titer of desaturated fatty alcohols.

Example 4: Production of Fatty Alcohols in Controlled Fermentations

The fermentations were carried out in a BioFlo 415 bioreactor (Eppendorf/New Brunswick), equipped with a 14 L vessel (10 L max working volume). pH was controlled at 5.0±0.1 with automated addition of a 2N solution of $H_2SO_4$ and a 4N solution of NaOH. Dissolved oxygen was measured using a polarographic electrode and automatically controlled at 20% saturation by changing the stirring speed of three 6-blade Rushton turbines. Strain *Yarrowia lipolytica* ST6379 was inoculated into the fermentation medium (2 g/L yeast extract, 13.4 g/L yeast nitrogen base, 0.76 g/L lysine, 0.76 g/L uracil, 0.024 mg/L thiamine, 0.002 g/L biotin, and 50 g/L glycerol). After 25 hours of fermentation, the fermentation medium (6 L) was supplemented with 750 ml nutrient-rich feed (which was composed of 16.2 g/L yeast extract, 108.6 g/L yeast nitrogen base, 6.2 g/L lysine, 0.2 mg/L thiamine, 0.02 g/L biotin, and 326 g/L glycerol), followed by a pulse of glycerol to a concentration of 50 g/L in the reactor at 32 h. From 36 hours glycerol was fed continuously keeping a steady glycerol concentration of 20-30 g/L. The fermentation lasted a total of 48 hours. The fatty alcohol concentrations at the end of the fermentation are given in Table 6.

In total 2.86 g/L desaturated fatty alcohols were produced.

TABLE 6

Production of fatty alcohols by strain ST6379

| Strain | Fatty alcohols (g/L) | | | |
|---|---|---|---|---|
|  | 14:OH | 16:OH | (Z)9-16:OH | (Z)11-16:OH |
| ST6379 | 0.116 | 2.265 | 0.290 | 2.570 |

Example 5: Method to Produce *Lepidoptera* Pheromones

Strains ST6527, ST6360 and ST7394 were cultivated in minimal medium as described in Example 3. The medium for strain ST7394 was additionally supplemented with 1 g/L methyl myristate.

By expressing different desaturases and fatty alcohol reductases, the platform yeast strain could be used to produce different desaturated fatty alcohols (Table 7).

TABLE 7

| Strain name | Strain description | Fatty-acyl-CoA desaturase | Fatty-acyl-CoA reductase | Acetyltransferase | Product |
|---|---|---|---|---|---|
| ST6527 | Δhfd4 Δhfd1 Δpex10 Δfao1 | Atrd11 | Har_FAR | none | 46.1 ± 1.4 mg/L Z11-hexadecen-1-ol |
| ST7394 | Δhfd4 Δhfd1 Δpex10 Δfao1 Δhfd2 Δhfd3 GPAT↓ | Dmd9 | Har_FAR | Acetyltransferase Atf1 from *S. cerevisiae* | 24.9 ± 2.5 mg/L Z9-tetradecen-1-yl acetate |

TABLE 7-continued

| Strain name | Strain description | Fatty-acyl-CoA desaturase | Fatty-acyl-CoA reductase | Acetyltransferase | Product |
|---|---|---|---|---|---|
| ST6360 | Δhfd4 Δhfd1 Δpex10 Δfao1 | Atrd11 desaturase from Spodoptera litura | Har_FAR Hs_FAR | Acetyltransferase Atf1 from S. cerevisiae | 27.5 ± 0.9 mg/L Z9-tetradecenanol 15.2 ± 0.8 mg/L Z9-tetradecen-1-yl acetate 25.2 ± 2.0 mg/L Z11-hexadecen-1-ol |

Example 6: Method to Produce Lepidoptera Pheromones

A gene encoding a fatty-acyl-CoA desaturase and a gene encoding a fatty-acyl-CoA reductase are expressed in a *Y. lipolytica* cell with deletions in PEX10, HFD1, HFD4 and FAO1 genes, and with reduced expression of GPAT. The resulting cell, when cultivated in fermentation medium, produces desaturated fatty alcohols. These fatty alcohols are recovered from the broth and chemically oxidised into the corresponding fatty aldehydes.

A gene, encoding a fatty-acyl-CoA desaturase, a gene encoding a fatty-acyl-CoA reductase, are expressed in a *Y. lipolytica* cell overexpressing an acetyltransferase, and having deletions in PEX10, HFD1, HFD4 and FAO1 genes, and with reduced expression of GPAT. The resulting cell, when cultivated in fermentation medium, produces desaturated fatty alcohol acetates.

TABLE 8

Examples of gene combinations and resulting products.

Figure 5:
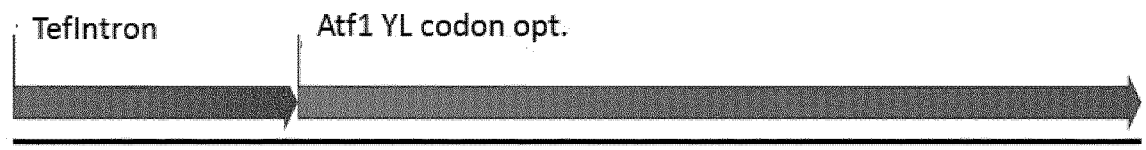
FIG. 5: expression cassette of Atf1. Atf1 YL codon opt: Atf1 codon optimised for *Yarrowia lipolytica*

| Fatty-acyl-CoA desaturase | Fatty-acyl-CoA reductase | Acetyltransferase | Product |
|---|---|---|---|
| Δ11 desaturase from *Amyelois transitella* | Reductase from *Helicoverpa armigera* | none | Z11-hexadecen-1-ol |
| Δ9 desaturase from *Drosophila melanogaster* (FIG. 4) | Reductase from *Helicoverpa armigera* (FIG. 4) | Acetyltransferase Atf1 from *S. cerevisiae* (FIG. 5) | Z9-tetradecen-1-yl acetate |
| Δ11 desaturase from *Choristoneura rosaceana* | Reductase from *Helicoverpa armigera* | Acetyltransferase Atf1 from *S. cerevisiae* | Z11-tetradecen-1-yl acetate |
| Δ11 desaturase from *Choristoneura parallela* | Reductase from *Helicoverpa armigera* | Acetyltransferase Atf1 from *S. cerevisiae* | E11-tetradecen-1-yl acetate |

Sequences

SEQ ID NO: 1—*S. cerevisiae*-codon-optimised nucleotide sequence of *A. transitella* Δ11-desaturase; mRNA-coding sequence.

SEQ ID NO: 2—Amino acid sequence of *A. transitella* delta-11-desaturase (translation)

SEQ ID NO: 3 Nucleotide sequence of *Y. lipolytica* fatty aldehyde dehydrogenase hfd1 (YALI0F23793g)

SEQ ID NO: 4: Amino acid sequence of *Y. lipolytica* fatty aldehyde dehydrogenase HFD1

SEQ ID NO: 5: Nucleotide sequence of *Y. lipolytica* fatty aldehyde dehydrogenase hfd4 (YALI0B01298g)

SEQ ID NO: 6 Amino acid sequence of *Y. lipolytica* fatty aldehyde dehydrogenase HFD4

SEQ ID NO: 7 Nucleotide sequence of *Y. lipolytica* peroxisome biogenesis factor pex10 (YALI0C01023g) PEX10

SEQ ID NO: 8 Amino acid sequence of *Y. lipolytica* peroxisome biogenesis factor PEX10

SEQ ID NO: 9 Nucleotide sequence of *Y. lipolytica* glycerol-3-phosphate o-acyltransferase gpat (YALI0C00209g)

SEQ ID NO: 10 Amino acid sequence of *Y. lipolytica* glycerol-3-phosphate o-acyltransferase GPAT SEQ ID NO: 11—*S. cerevisiae*-codon-optimised nucleotide sequence of *H. subflexa* fatty acyl reductase; mRNA-coding sequence.

SEQ ID NO: 12—Amino acid of *H. subflexa* fatty acyl reductase

SEQ ID NO: 13: HarFAR DNA

SEQ ID NO: 14: HarFAR

SEQ ID NO: 15: HasFAR DNA

SEQ ID NO: 16: HasFAR

SEQ ID NO: 17: Dmed9 DNA

SEQ ID NO: 18: Dmed9

SEQ ID NO: 19: Cro_delta11Z

SEQ ID NO: 20: Cpa_delta11E

SEQ ID NO: 21 FAO1 DNA

SEQ ID NO: 22 Fao1 protein

SEQ ID NO: 23: Ban_FAR DNA

SEQ ID NO: 24: Ban_FAR

SEQ ID NO: 25 PR-141

SEQ ID NO: 26 PR-142

SEQ ID NO: 27 PR-10851 (Atrd11 expression cassette_fw)

SEQ ID NO: 28 PR-10853 (Hs_Far expression cassette_fw)

SEQ ID NO: 29 PR-10655 (EpiVecYL_fw)

SEQ ID NO: 30 PR-10656 (EpiVecYL_rev)

SEQ ID NO: 31 PR-10702 (Apex10YL_up_fw)

SEQ ID NO: 32 PR-10703 (Apex10YL_up_rev)

SEQ ID NO: 33 PR-10704 (Apex10YL_down_fw)

SEQ ID NO: 34 PR-10705 (Apex10YL_down_rev)

SEQ ID NO: 35 PR-10767 (NatMxSynYL-start_rev_new)

SEQ ID NO: 36 PR-11047 (NatMxSynYL-end_rev_new)

SEQ ID NO: 37 PR-11110 (*E. coli* backboneUSER_fw)

SEQ ID NO: 38 PR-11111 (*E. coli* backboneUSER_rev)

SEQ ID NO: 39 PR-11138 (Hphsyn_fw)

SEQ ID NO: 40 PR-11139 (Hphsyn_rev)

SEQ ID NO: 41 PR-11694 (GPAT_up_USER_fw)

SEQ ID NO: 42 PR-11695 (GPAT_down_USER_rev)

SEQ ID NO: 43 PR-13494 (Nat-Tcyc-loxP_fw)

SEQ ID NO: 44 PR-13549 (loxP-PrTefIntron_fw)

SEQ ID NO: 45 PR-14269 (UraYL_fw)
SEQ ID NO: 46 PR-14270 (UraYL rev)
SEQ ID NO: 47 PR-15426 (Δhfd1_up_fw)
SEQ ID NO: 48 PR-15427 (Δhfd1_up_rev)
SEQ ID NO: 49 PR-15428 (Δhfd1_down_fw)
SEQ ID NO: 50 PR-15429 (Δhfd1_down_rev)
SEQ ID NO: 51 PR-15438 (Δhfd4_up_fw)
SEQ ID NO: 52 PR-15439 (Δhfd4_up_rev)
SEQ ID NO: 53 PR-15440 (Δhfd4_down_fw)
SEQ ID NO: 54 PR-15441 (Δhfd4_down_rev)
SEQ ID NO: 55 PR-16463 (Δfao1YL_up_fw)
SEQ ID NO: 56 PR-16464 (Δfao1YL_up_rev)
SEQ ID NO: 57 PR-16465 (Δfao1YL_down_fw)
SEQ ID NO: 58 PR-16466 (Δfao1YL_down_rev)
SEQ ID NO: 59 PR-16696 (GPAT_up_rev)
SEQ ID NO: 60 PR-16698 (GPAT_100bpPr_down_fw)

SEQ ID NO: 61 *Y. lipolytica* codon-optimized nucleotide sequence of alcohol acetyltransferase from *S. cerevisiae* ATF1

SEQ ID NO: 62 *Saccharomyces cerevisiae* ATF1p amino acid sequence

SEQ ID NO: 63 *Y. lipolytica* codon-optimized nucleotide sequence of Δ9 desaturase from *Drosophila melanogaster* Dmd9

SEQ ID NO: 64 *Y. lipolytica* codon-optimized nucleotide sequence of fatty acyl reductase from *H. armigera* Har_FAR SEQ ID NO: 65 *Y. lipolytica* codon-optimized nucleotide sequence of Δ9 desaturase from *Spodoptera litura* Des11

SEQ ID NO: 66 Δ9 desaturase from *Spodoptera litura* Des11

SEQ ID NO: 67 *Y. lipolytica* codon-optimized nucleotide sequence of Δ11 desaturase from *Amyelois transitella*

SEQ ID NO: 68 Amino acid sequence of Δ11 desaturase from *Amyelois transitella*

SEQ ID NO: 69 *Y. lipolytica* codon-optimized nucleotide sequence of fatty acyl reductase from *Helicoverpa armigera*

SEQ ID NO: 70 Amino acid sequence of fatty acyl reductase from *Helicoverpa armigera*

| SEQ ID NO: 71 | PR-10714 |
|---|---|
| SEQ ID NO: 72 | PR-10766 |
| SEQ ID NO: 73 | PR-10767 |
| SEQ ID NO: 74 | PR-11047 |
| SEQ ID NO: 75 | PR-13338 |
| SEQ ID NO: 76 | PR-141 |
| SEQ ID NO: 77 | PR-14148 |
| SEQ ID NO: 78 | PR-14149 |
| SEQ ID NO: 79 | PR-142 |
| SEQ ID NO: 80 | PR-14565 |
| SEQ ID NO: 81 | PR-14566 |
| SEQ ID NO: 82 | PR-14567 |
| SEQ ID NO: 83 | PR-14568 |
| SEQ ID NO: 84 | PR-14589 |
| SEQ ID NO: 85 | PR-14590 |
| SEQ ID NO: 86 | PR-14591 |
| SEQ ID NO: 87 | PR-14592 |
| SEQ ID NO: 88 | PR-15430 |
| SEQ ID NO: 89 | PR-15431 |
| SEQ ID NO: 90 | PR-15432 |
| SEQ ID NO: 91 | PR-15433 |
| SEQ ID NO: 92 | PR-15434 |
| SEQ ID NO: 93 | PR-15435 |
| SEQ ID NO: 94 | PR-15436 |
| SEQ ID NO: 95 | PR-15437 |
| SEQ ID NO: 96 | PR-15930 |
| SEQ ID NO: 97 | PR-16592 |
| SEQ ID NO: 98 | PR-16593 |
| SEQ ID NO: 99 | PR-16594 |
| SEQ ID NO: 100 | PR-16595 |
| SEQ ID NO: 101 | PR-14149 |
| SEQ ID NO: 102 | PR-14279 |

-continued

| SEQ ID NO: 103 | PR-14395 |
|---|---|
| SEQ ID NO: 104 | PR-14396 |
| SEQ ID NO: 105 | PR-14397 |
| SEQ ID NO: 106 | PR-14398 |
| SEQ ID NO: 107 | PR-15521 |
| SEQ ID NO: 108 | PR-15522 |
| SEQ ID NO: 109 | PR-18486 |
| SEQ ID NO: 110 | PR-18487 |
| SEQ ID NO: 111 | PR-18490 |
| SEQ ID NO: 112 | PR-18489 |
| SEQ ID NO: 113 | PR-18499 |
| SEQ ID NO: 114 | PR-18500 |

REFERENCES

Alfaro, Navarro-Llopis, Primo, 2009. Optimization of pheromone dispenser density for managing the rice striped stem borer, *Chilo suppressalis* (Walker), by mating disruption. Crop Protection. 28:567-572.

Angerer, Radermacher, Mankowska, Steger, Zwicker, Heide, Wittig, Brandt, Zickermann, 2014. The LYR protein subunit NB4M/NDUFA6 of mitochondrial complex I anchors an acyl carrier protein and is essential for catalytic activity. PNAS. 111(14)

Bari, 2003. Development of pheromone mating disruption strategies for the suppression of the artichoke plume moth in artichokes grown on the central coast of California. ISHS Acta Horticulturae 660: V International Congress on Artichoke. doi: 10.17660/ActaHortic.2004.660.80

Chen, Beckerich, Gaillardin, 1997. One-step transformation of the dimorphic yeast *Yarrowia lipolytica*. Appl Microbiol Biotechnol. 48(2):232-5

Eizaguirre, Sans, López, Albajes. 2002. Effects of mating disruption against the Mediterranean corn borer, *Sesamia nonagrioides*, on the European corn borer *Ostrinia nubilalis*. Use of pheromones and other semiochemicals in integrated production IOBC wprs Bulletin.

Ferrell, Yao, 1972. Reductive and oxidative synthesis of saturated and unsaturated fatty aldehydes, J Lipid Res. 13(1):23-6.)

Iwama R, Kobayashi S, Ohta A, Horiuchi H, Fukuda R. 2014; 289(48):33275-86. J Biol Chem. Fatty aldehyde dehydrogenase multigene family involved in the assimilation of n-alkanes in *Yarrowia lipolytica*.

Jensen, Strucko, Kildegaard, David, Maury, Mortensen, Forster, Nielsen, Borodina, 2014. EasyClone: method for iterative chromosomal integration of multiple genes in *Saccharomyces cerevisiae*, FEMS Yeast Res. 14(2):238-48

Iwama R, Kobayashi S, Ohta A, Horiuchi H, Fukuda R. FEMS Yeast Res. 2015 May; 15(3). Alcohol dehydrogenases and an alcohol oxidase involved in the assimilation of exogenous fatty alcohols in *Yarrowia lipolytica*.

Kehat, Dunkelblum, 1993. Sex Pheromones: achievements in monitoring and mating disruption of cotton pests in Israel, Achieves of Insect Biochemistry and Physiology. 22:425-431.

Li, Zhang, 2009. An environmentally benign TEMPO-catalyzed efficient alcohol oxidation system with a recyclable hypervalent iodine(III) reagent andilts facile preparation. Synthesis, 1163-1169a.

Meyer, Schreiber, 1994. Acceleration of the Dess-Martin oxidation by water J. Org. Chem., 59, 7549-7552;

Okada, Asawa, Sugiyama, Kirihara, Iwai, Kimura, 2014. Sodium hypochlorite pentahydrate (NaOCl.5H2O) crystals as an extraordinary oxidant for primary and secondary alcohols. Synlett, 25, 596-598.

Steves J. E. and Stahl S. S., 2013. Copper(I)/ABNO-catalyzed aerobic alcohol oxidation: alleviating steric and electronic constraints of Cu/TEMPO catalyst systems. J. Am. Chem. Soc., 135, 15742-15745

Stovicek V, Borja G M, Forster J, Borodina I. EasyClone 2.0: expanded toolkit of integrative vectors for stable gene expression in industrial *Saccharomyces cerevisiae* strains. J Ind Microbiol Biotechnol. 2015 November; 42(11): 1519-31.

Sumita T, Iida T, Hirata A, Horiuchi H, Takagi M, Ohta A. (2002) FEMS Microbiol Lett. 2002 Aug. 27; 214(1):31-8. "Peroxisome deficiency represses the expression of n-alkane-inducible YlALK1 encoding cytochrome P450ALK1 in *Yarrowia lipolytica*." Tamura, Aoyama, Takido, Kodomari, 2012. Novel [4-Hydroxy-TEMPO+NaCl]/SiO2 as a reusable catalyst for aerobic oxidation of alcohols to carbonyls. Synlett, 23, 1397-1407.

Yadav, Reddy, Basak, Narsaiah, 2004. Recyclable 2nd generation ionic liquids as green solvents for the oxidation of alcohols with hypervalent iodine reagents, Tetrahedron, 60, 2131-2135.

Wu, Zhang, Yao, Xu, Wang and Zhang, 2012. Management of diamondback moth, *Plutella xylostella* (Lepidoptera: Plutellidae) by mating disruption. Insect Science 19 (6), 643-648.

Items

1. An oleaginous yeast cell capable of producing a desaturated fatty alcohol, said cell:
   i) expressing at least one heterologous desaturase capable of introducing at least one double bond in a fatty acyl-CoA; and
   ii) expressing at least one heterologous fatty acyl-CoA reductase, capable of converting at least part of said desaturated fatty acyl-CoA to a desaturated fatty alcohol; and
   iii) having reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or having reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

2. The yeast cell according to item 1, wherein the yeast cell has reduced activity of Pex10 (SEQ ID NO: 8) and of at least one of Hfd1 (SEQ ID NO: 4), Hfd4 (SEQ ID NO: 6), Fao1 (SEQ ID NO: 22) and GPAT (SEQ ID NO: 10), or reduced activity of Pex10 (SEQ ID NO: 8) and at least one of Hfd1 (SEQ ID NO: 4), Hfd4 (SEQ ID NO: 6), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8) and at least one of Hfd1 (SEQ ID NO: 4), Hfd4 (SEQ ID NO: 6), Fao1 (SEQ ID NO: 22) and GPAT (SEQ ID NO: 10).

3. The yeast cell according to item 2, wherein the yeast is of the *Yarrowia* species, preferably the yeast is *Yarrowia lipolytica*.

4. The yeast cell according to any one of the preceding items, wherein the at least one heterologous desaturase is selected from the group consisting of a $\Delta 3$ desaturase, a $\Delta 5$ desaturase, a $\Delta 6$ desaturase, a $\Delta 7$ desaturase, a $\Delta 8$ desaturase, a $\Delta 9$ desaturase, a $\Delta 10$ desaturase, a $\Delta 11$ desaturase, a $\Delta 12$ desaturase, a $\Delta 13$ desaturase and a $\Delta 14$ desaturase.

5. The yeast cell according to any one of the preceding items, wherein the reduction in activity of Hfd1, Hfd4, Pex10 and Fao1 or a protein having at least 60% homology thereto is partial or total, and/or wherein the reduction in activity of GPAT or a protein having at least 60% homology thereto is partial.

6. The yeast cell according to any one of the preceding items, wherein the desaturase is derived from an organism of an insect, such as from the Lepidoptera order.

7. The yeast cell according to any one of the preceding items, wherein the desaturase is a $\Delta 11$ desaturase having at least 60% homology to the $\Delta 11$ desaturase from *Amyelois transitella* as set forth in SEQ ID NO: 2.

8. The yeast cell according to any one of the preceding items, wherein the desaturase is a $\Delta 9$ desaturase having at least 60% homology to the $\Delta 9$ desaturase from *Drosophila melanogasteras* set forth in SEQ ID NO: 18.

9. The yeast cell according to any one of the preceding items, wherein the desaturase is a $\Delta 11$ desaturase having at least 60% homology to the $\Delta 11$ desaturase from *Choristoneura rosaceana* as set forth in SEQ ID NO: 19.

10. The yeast cell according to any one of the preceding items, wherein the desaturase is a $\Delta 11$ desaturase having at least 60% homology to the $\Delta 11$ desaturase from *Choristoneura parallela* as set forth in SEQ ID NO: 20.

11. The yeast cell according to any one of the preceding items, wherein the FAR is selected from:
    i) a FAR having at least 80% homology to the FAR from *Helicoverpa armigera* as set forth in SEQ ID NO: 14;
    ii) a FAR having at least 80% homology to the FAR from *Helicoverpa assulta* as set forth in SEQ ID NO: 16;
    iii) a FAR having at least 80% homology to the FAR from *Heliothis subflexa* as set forth in SEQ ID NO: 12; and
    iv) a FAR having at least 80% homology to the FAR from *Bicyclus anynana* as set forth in SEQ ID NO: 24.

12. The yeast cell according to any one of the preceding items, further expressing an acetyltransferase capable of converting at least part of said desaturated fatty alcohol to a desaturated fatty alcohol acetate.
13. The yeast cell according to any one of the preceding items, wherein at least one of the genes encoding a desaturase, a fatty acyl-CoA reductase or an acetyltransferase is present in high copy number.
14. The yeast cell according to any one of the preceding items, wherein at least one of the genes encoding a desaturase, a fatty acyl-CoA reductase or an acetyltransferase is under the control of an inducible promoter.
15. The yeast cell according to any one of the preceding items, wherein at least one of the genes encoding a desaturase, a fatty acyl-CoA reductase or an acetyltransferase is codon-optimised for said yeast cell.
16. The yeast cell according to any one of the preceding items, wherein the genes encoding a desaturase, a fatty acyl-CoA reductase or an acetyltransferase are comprised within the genome of the cell or within a vector comprised within the cell.
17. The yeast cell according to any one of the preceding items, wherein the cell comprises a deletion or a mutation of at least one of HFD1 (SEQ ID NO: 3), HFD4 (SEQ ID NO: 5), PEX10 (SEQ ID NO: 7), FAO1 (SEQ ID NO: 21) and/or a mutation of GPAT (SEQ ID NO: 9), or a deletion or a mutation in at least one nucleic acid sequence having at least 60% homology thereto, such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology thereto, resulting in reduction of activity of at least one of Hfd1, Hfd4, Pex10, Fao1 and GPAT.
18. The yeast cell according to item 17, comprising a mutation of in PEX10 (SEQ ID NO: 7) and at least one of HFD1 (SEQ ID NO: 3), HFD4 (SEQ ID NO: 5), FAO1 (SEQ ID NO: 21) and/or GPAT (SEQ ID NO: 9) or a homologue thereof.
19. The yeast cell according to any one of the preceding items, wherein HFD1 (SEQ ID NO: 3), HFD4 (SEQ ID NO: 5), PEX10 (SEQ ID NO: 7) and/or FAO1 (SEQ ID NO: 21) or a homologue thereof having at least 60% homology thereto is deleted or mutated, resulting in total loss of activity of Hfd1, Hfd4, Pex10 and/or Fao1, and/or wherein GPAT (SEQ ID NO: 9) or a homologue thereof having at least 60% homology thereto is mutated, resulting in reduced activity of GPAT.
20. The yeast cell according to any one of the preceding items, wherein the cell has reduced or total loss of activity of at least two of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).
21. The yeast cell according to any one of the preceding items, wherein the cell has reduced or total loss of activity of at least three of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).
22. The yeast cell according to any one of the preceding items, wherein the cell has reduced or total loss of activity of four of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).
23. The yeast cell according to any one of the preceding items, wherein the cell has reduced or total loss of activity of all of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).
24. The yeast cell according to any one of the preceding items, wherein the fatty acyl-CoA reductase is encoded by a nucleic acid sequence identical to or having at least 90% homology to SEQ ID NO: 11, SEQ ID NO: 13 or SEQ ID NO: 15, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to SEQ ID NO: 11, SEQ ID NO: 13 or SEQ ID NO: 15.
25. The yeast cell according to any one of the preceding items, wherein the cell is capable of producing fatty alcohols with a total titre of at least 1 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L, wherein the total titre is the sum of the titre of desaturated fatty alcohols and the titre of saturated fatty alcohols.
26. The yeast cell according to any one of the preceding items, wherein the desaturated fatty alcohols produced by the cell represent at least 20% of the total fatty alcohols produced by the cell, such as at least 30%, such as at least 40%, such as at least 50%, such as at least 60%, such as at least 70%, such as at least 80%, such as at least 90% of the total fatty alcohols produced by the cell.
27. The yeast cell according to any one of the preceding items, wherein the cell is capable of producing (Z)11-C16:OH with a titre of at least 0.5 mg/L, such as at least 1 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L (Z)11-C16:OH.
28. The yeast cell according to any one of the preceding items, wherein the (Z)11-C16:OH produced by the cell represents at least 20% of the total fatty alcohols produced by the cell, such as at least 30%, such as at least 40%, such as at least 50%, such as at least 60%, such as at least 70%, such as at least 80%, such as at least 90% of the total fatty alcohols produced by the cell.
29. A method of producing a desaturated fatty alcohol and/or a desaturated fatty alcohol acetate in an oleaginous yeast cell, said method comprising the steps of providing a yeast cell and incubating said yeast cell in a medium, wherein the yeast cell:

i) expresses at least one heterologous desaturase capable of introducing at least one double bond in a fatty acyl-CoA, thereby converting at least part of said fatty acyl-CoA to a desaturated fatty acyl-CoA; and ii) expresses at least one heterologous fatty acyl-CoA reductase, capable of converting at least part of said desaturated fatty acyl-CoA to a desaturated fatty alcohol, thereby producing said desaturated fatty alcohol; and iii) has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or reduced activity of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

30. The method according to item 27, wherein the yeast cell has a mutation resulting in reduced activity of Pex10 (SEQ ID NO: 8) and a mutation resulting in reduced activity of at least one of Hfd1 (SEQ ID NO: 4), Hfd4 (SEQ ID NO: 6), Fao1 (SEQ ID NO: 22) and GPAT (SEQ ID NO: 10) or has a mutation resulting in reduced activity of at least one protein having at least 60% homology to Pex10 (SEQ ID NO: 8) and a mutation resulting in reduced activity or at least one of Hfd1 (SEQ ID NO: 4), Hfd4 (SEQ ID NO: 6), Fao1 (SEQ ID NO: 22) and GPAT (SEQ ID NO: 10), such as at least 65% homology, such as at least 70% homology, such as at least 75% homology, such as at least 80% homology, such as at least 81% homology, such as at least 82% homology, such as at least 83% homology, such as at least 84% homology, such as at least 85% homology, such as at least 86% homology, such as at least 87% homology, such as at least 88% homology, such as at least 89% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology to Pex10 (SEQ ID NO: 8) and at least one of Hfd1 (SEQ ID NO: 4), Hfd4 (SEQ ID NO: 6), Fao1 (SEQ ID NO: 22) and GPAT (SEQ ID NO: 10).

31. The method according to any one of items 29 to 30, wherein the yeast cell is as defined in any one of items 1 to 29.

32. The method according to any one of items 29 to 31, further comprising the step of converting the desaturated fatty alcohol of step ii) into a fatty alcohol acetate or a fatty aldehyde.

33. The method according to any one of items 29 to 32, further comprising the step of recovering the desaturated fatty alcohol, the fatty alcohol acetate and/or the aldehyde.

34. The method according to any one of items 29 to 33, further comprising the step of formulating the desaturated fatty alcohol, the fatty alcohol acetate and/or the aldehyde in a pheromone composition.

35. The method according to any one of items 29 to 34, wherein the pheromone composition further comprises one or more additional compounds such as a liquid or solid carrier or substrate.

36. The method according to any one of items 29 to 33, wherein at least part of the desaturated fatty alcohol is Z11-16:OH.

37. A nucleic acid construct for modifying a yeast cell, said construct comprising:

i) a first polynucleotide encoding at least one heterologous desaturase capable of introducing at least one double bond in a fatty acyl-CoA; and ii) a second polynucleotide encoding at least one heterologous fatty acyl-CoA reductase (FAR), capable of converting at least part of said desaturated fatty acyl-CoA to a desaturated fatty alcohol; and iii) optionally, additional polynucleotides for reducing activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10) or of at least one protein having at least 60% homology to one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10), wherein optionally the first polynucleotide and/or the second polynucleotide and/or the additional polynucleotides are under the control of a promoter.

38. The nucleic acid construct according to item 37, further comprising a third polynucleotide encoding at least one acetyltransferase capable of converting at least part of said desaturated fatty alcohol to a desaturated fatty alcohol acetate.

39. A kit of parts comprising:

a) the yeast cell according to any one of items 1 to 28 and instructions for use; and/or b) a nucleic acid construct according to any one of items 37 or 38, wherein said construct is for modifying a yeast cell, and c) optionally the yeast cell to be modified.

40. The kit of parts according to item 39, wherein the yeast cell to be modified has reduced activity of at least one of Hfd1 (SEQ ID NO: 4), Hfd4 (SEQ ID NO: 6), Pex10 (SEQ ID NO: 8), Fao1 (SEQ ID NO: 22) and GPAT (SEQ ID NO: 10).

41. A desaturated fatty alcohol, a desaturated fatty alcohol acetate or a desaturated fatty aldehyde obtainable by the method according to any one of items 29 to 36.

42. Use of a desaturated fatty alcohol, a desaturated fatty alcohol acetate or a desaturated fatty aldehyde obtainable by the method according to any one of items 29 to 36.

The invention claimed is:

1. A *Yarrowia lipolytica* yeast cell capable of producing a desaturated fatty alcohol with a titer of at least 5 mg/L, said cell:
   i) expressing at least one heterologous desaturase capable of introducing at least one double bond in a fatty acyl-CoA; and
   ii) expressing at least one heterologous fatty acyl-CoA reductase (FAR) capable of converting at least part of said desaturated fatty acyl-CoA to a desaturated fatty alcohol; and
   iii) having:
      a mutation resulting in reduced activity of fatty alcohol oxidase Fao1 of *Yarrowia lipolytica*;
      a mutation resulting in reduced activity of storage lipid biosynthesis in *Yarrowia lipolytica*; and
      a mutation resulting in reduced activity of at least one of peroxisome biogenesis factor 10 Pex10 of *Yarrowia lipolytica* or fatty aldehyde dehydrogenase Hfd1 of *Yarrowia lipolytica*.

2. The yeast cell according to claim 1, wherein the at least one heterologous desaturase is selected from the group consisting of a Δ3 desaturase, a Δ5 desaturase, a Δ6 desaturase, a Δ7 desaturase, a Δ8 desaturase, a Δ9 desaturase, a Δ10 desaturase, a Δ11 desaturase, a Δ12 desaturase, a Δ13 desaturase and a Δ14 desaturase.

3. The yeast cell according to claim 1, wherein the at least one heterologous desaturase is an insect desaturase.

4. The yeast cell according to claim 1, wherein the FAR is selected from:
   i) a FAR having at least 80% homology to the FAR from *Helicoverpa armigera* as set forth in SEQ ID NO: 14;

ii) a FAR having at least 80% homology to the FAR from *Helicoverpa assulta* as set forth in SEQ ID NO: 16; or iii) a FAR having at least 80% homology to the FAR from *Heliothis subflexa* as set forth in SEQ ID NO: 12.

5. The yeast cell according to claim 1, further expressing an acetyltransferase capable of converting at least part of said desaturated fatty alcohol to a desaturated fatty alcohol acetate.

6. The yeast cell according to claim 1, wherein the cell is capable of producing (Z)11-C16:OH with a titre of at least 0.5 mg/L.

7. A method of producing a desaturated fatty alcohol or a desaturated fatty alcohol acetate in a *Yarrowia lipolytica* cell, said method comprising the steps of providing a cell according to claim 1 and incubating said cell in a medium.

8. The method according to claim 7, wherein the yeast cell is of the *Yarrowia* genus.

9. The yeast cell according to claim 3, wherein the at least one heterologous desaturase is a Δ11 desaturase having at least 60% homology to the Δ11 desaturase from *Amyelois transitella* as set forth in SEQ ID NO: 2 or a Δ9 desaturase having at least 60% homology to the Δ9 desaturase from *Drosophila melanogaster* as set forth in SEQ ID NO: 18.

10. The method according to claim 8, wherein the yeast cell is a *Yarrowia lipolytica* cell.

11. The method according to claim 8, wherein the cell is capable of producing (Z)11-C16:OH with a titre of at least 0.5 mg/L.

12. The yeast cell according to claim 1, wherein the cell is capable of producing (Z)9-C14:OH with a titre of at least 0.5 mg/L.

13. The yeast cell according to claim 1, wherein Pex10 is as set forth in SEQ ID NO: 8 and Hfd1 is as set forth in SEQ ID NO: 4.

14. The yeast cell according to claim 1, wherein the mutation resulting in reduced storage lipid biosynthesis is a mutation in glycerol-3-phosphate acyltransferase GPAT as set forth in SEQ ID NO: 10.

15. The yeast cell according to claim 2, wherein the at least one heterologous FAR selected from:

i) a FAR having at least 80% homology to the FAR from *Helicoverpa armigera* as set forth in SEQ ID NO: 14;

ii) a FAR having at least 80% homology to the FAR from *Helicoverpa assulta* as set forth in SEQ ID NO: 16; and iii) a FAR having at least 80% homology to the FAR from *Heliothis subflexa* as set forth in SEQ ID NO: 12.

16. The yeast cell according to claim 1, wherein the at least one heterologous desaturase is selected from the group consisting of a Δ9 desaturase and a Δ11 desaturase.

17. The yeast cell according to claim 16, wherein the at least one heterologous FAR selected from:

i) a FAR having at least 80% homology to the FAR from *Helicoverpa armigera* as set forth in SEQ ID NO: 14;

ii) a FAR having at least 80% homology to the FAR from *Helicoverpa assulta* as set forth in SEQ ID NO: 16;

iii) a FAR having at least 80% homology to the FAR from *Heliothis subflexa* as set forth in SEQ ID NO: 12.

\* \* \* \* \*